(12) United States Patent
Appendino et al.

(10) Patent No.: US 8,673,578 B2
(45) Date of Patent: Mar. 18, 2014

(54) METHODS OF IDENTIFYING ANTAGONISTS OF THE HTAS2R46 BITTER TASTE RECEPTOR

(75) Inventors: Giovanni Appendino, Turin (IT); Maik Behrens, Nuthetal (DE); Anne Brockhoff, Potsdam (DE); Wolfgang Meyerhof, Norderstedt (DE)

(73) Assignee: Deutsches Institut für Ernahrungsforschung Potsdam-Rehbrücke, Nuthetal (DE)

( * ) Notice: Subject to any disclaimer, the term of this patent is extended or adjusted under 35 U.S.C. 154(b) by 0 days.

(21) Appl. No.: 13/504,750

(22) PCT Filed: Oct. 27, 2010

(86) PCT No.: PCT/EP2010/006563
§ 371 (c)(1),
(2), (4) Date: Jul. 24, 2012

(87) PCT Pub. No.: WO2011/050955
PCT Pub. Date: May 5, 2011

(65) Prior Publication Data
US 2012/0283324 A1    Nov. 8, 2012

Related U.S. Application Data

(60) Provisional application No. 61/255,207, filed on Oct. 27, 2009.

(51) Int. Cl.
*G01N 33/53* (2006.01)
*G01N 33/567* (2006.01)
*C12Q 1/02* (2006.01)
*C12N 1/20* (2006.01)
*C12N 15/00* (2006.01)
*C12N 5/00* (2006.01)
*C12N 5/02* (2006.01)
*C12N 15/74* (2006.01)
*C07D 307/00* (2006.01)
*C07D 407/00* (2006.01)

(52) U.S. Cl.
USPC ........ 435/7.2; 435/29; 435/252.3; 435/320.1; 435/325; 435/471; 549/302

(58) Field of Classification Search
None
See application file for complete search history.

(56) References Cited

FOREIGN PATENT DOCUMENTS

EP    1 983 342 A1    10/2008
WO    WO 2006/053771 A2    5/2006

OTHER PUBLICATIONS

Brockhoff A, et al. Journal of Agriculture and Food Chemistry, 55(15):6236-6243, Jul. 2007.*
Brockhoff, Anne, et al., "Broad tuning of the human bitter taste receptor hTAS2R46 to various sesquiterpene lactones, clerodane and labdane diterpenoids, strychnine, and denatonium" Journal of Agriculture and Food Chemistry, vol. 55, No. 15:6236-6243, Jul. 2007, p. 6241, col. 1; Fig 6 Abstract.

* cited by examiner

*Primary Examiner* — Robert Landsman
(74) *Attorney, Agent, or Firm* — Faegre Baker Daniels LLP

(57) ABSTRACT

The present invention relates to antagonists and agonists of the human bitter-taste receptors hTAS2R40, hTAS2R43, hTAS2R44, hTAS2R46, and hTAS2R47. The invention also relates to methods for identifying further molecules that suppress or enhance bitter taste transduction or bitter taste response mediated by hTAS2R40, hTAS2R43, hTAS2R44, hTAS2R46, and/or hTAS2R47 and uses thereof.

14 Claims, 5 Drawing Sheets

(I)

(II)

A)

B)

3β hydroxy dihydro costunolide + strychnine (μM)

| 3β hydroxy dihydro costunolide (μM) | strychnine EC$_{50}$ (μM) | maximum signal amplitude (arbitrary light units) |
|---|---|---|
| 0 | 0.39 ± 0.08 | 0.42 ± 0.09 |
| 10 | 2.74 ± 0.29 | 0.40 ± 0.06 |
| 30 | 5.39 ± 1.02 | 0.41 ± 0.06 |
| 100 | 21.72 ± 15.24 * | 0.34 ± 0.07 |

A)

B)

| compound | R₁ | R₂ | effect on hTAS2R46 | EC₅₀ / IC₅₀ (µM) |
|---|---|---|---|---|
| 3βhydroxy dihydro costunolide | -OH | -CH₃ | inhibition | 15.3 ± 5.9 |
| costunolide | -H | =CH₂ | activation | 8.6 ± 0.3 |
| dihydro costunolide | -H | -CH₃ | activation | 8.3 ± 4.8 |
| 3keto dihydro costunolide | =O | -CH₃ | inhibition | 97.8 ± 5.9 |
| 3βhydroxy dihydro costunolide acetate | -OAc | -CH₃ | activation | 1.1 ± 0.5 |

SEQUENCE LISTING

<160> NUMBER OF SEQ ID NOS: 14

<210> SEQ ID NO 1
<211> LENGTH: 897
<212> TYPE: DNA
<213> ORGANISM: Homo sapiens

<400> SEQUENCE: 1

```
atgctagagt ctcacctcat tatctatttt cttcttgcag tgatacaatt tcttcttggg      60
attttcacaa atggcatcat tgtggtggtg aatggcattg acttgatcaa gcacagaaaa     120
atggctccgc tggatctcct tctttcttgt ctggcagttt ctagaatttt tctgcagttg     180
ttcatcttct acgttaatgt gattgttatc ttcttcatag aattcatcat gtgttctgcg     240
aattgtgcaa ttctcttatt tataaatgaa ttggaacttt ggcttgccac atggctcggc     300
gttttctatt gtgccaaggt tgccagcgtc cgtcacccac tcttcatctg gttgaagatg     360
aggatatcca agctggtccc atggatgatc ctggggtctc tgctatatgt atctatgatt     420
tgtgttttcc atagcaaata tgcagggttt atggtcccat acttcctaag gaaattttc     480 tcccaaaatg ccacaattca aaaagaagat acactggcta tacagatttt ctcttttgtt     540
gctgagttct cagtgccatt gcttatcttc ctttttgctg ttttgctctt gatttctctct   600 ctggggaggc acacccggca aatgagaaac acagtggccg gcagcagggt tcctggcagg     660
```

```
ggtgcaccca tcagcgcgtt gctgtctatc ctgtccttcc tgatcctcta cttctcccac    720
tgcatgataa agttttttct ctcttctcta agtttcaca tcagaaggtt catctttctg    780
ttcttcatcc ttgtgattgg tatataccct tctggacact ctctcatctt aattttagga    840
aatcctaaat tgaaacaaaa tgcaaaaaag ttcctcctcc acagtaagtg ctgtcag      897
```

<210> SEQ ID NO 2
<211> LENGTH: 299
<212> TYPE: PRT
<213> ORGANISM: Homo sapiens

<400> SEQUENCE: 2

```
Met Leu Glu Ser His Leu Ile Ile Tyr Phe Leu Leu Ala Val Ile Gln
1               5                   10                  15

Phe Leu Leu Gly Ile Phe Thr Asn Gly Ile Ile Val Val Asn Gly
            20                  25                  30

Ile Asp Leu Ile Lys His Arg Lys Met Ala Pro Leu Asp Leu Leu Leu
        35                  40                  45

Ser Cys Leu Ala Val Ser Arg Ile Phe Leu Gln Leu Phe Ile Phe Tyr
50                  55                  60

Val Asn Val Ile Val Ile Phe Phe Ile Glu Phe Ile Met Cys Ser Ala
65                  70                  75                  80

Asn Cys Ala Ile Leu Leu Phe Ile Asn Glu Leu Glu Leu Trp Leu Ala
                85                  90                  95

Thr Trp Leu Gly Val Phe Tyr Cys Ala Lys Val Ala Ser Val Arg His
            100                 105                 110

Pro Leu Phe Ile Trp Leu Lys Met Arg Ile Ser Lys Leu Val Pro Trp
        115                 120                 125

Met Ile Leu Gly Ser Leu Leu Tyr Val Ser Met Ile Cys Val Phe His
130                 135                 140

Ser Lys Tyr Ala Gly Phe Met Val Pro Tyr Phe Leu Arg Lys Phe Phe
145                 150                 155                 160

Ser Gln Asn Ala Thr Ile Gln Lys Glu Asp Thr Leu Ala Ile Gln Ile
                165                 170                 175

Phe Ser Phe Val Ala Glu Phe Ser Val Pro Leu Leu Ile Phe Leu Phe
            180                 185                 190

Ala Val Leu Leu Leu Ile Phe Ser Leu Gly Arg His Thr Arg Gln Met
        195                 200                 205

Arg Asn Thr Val Ala Gly Ser Arg Val Pro Gly Arg Gly Ala Pro Ile
210                 215                 220

Ser Ala Leu Leu Ser Ile Leu Ser Phe Leu Ile Leu Tyr Phe Ser His
225                 230                 235                 240

Cys Met Ile Lys Val Phe Leu Ser Ser Leu Lys Phe His Ile Arg Arg
                245                 250                 255

Phe Ile Phe Leu Phe Phe Ile Leu Val Ile Gly Ile Tyr Pro Ser Gly
            260                 265                 270

His Ser Leu Ile Leu Ile Leu Gly Asn Pro Lys Leu Lys Gln Asn Ala
        275                 280                 285

Lys Lys Phe Leu Leu His Ser Lys Cys Cys Gln
290                 295
```

<210> SEQ ID NO 3
<211> LENGTH: 897
<212> TYPE: DNA
<213> ORGANISM: Homo sapiens

```
<400> SEQUENCE: 3
atgcttcggt tattctattt ctctgctatt attgcctcag ttattttaaa ttttgtagga      60
atcattatga atctgtttat tacagtggtc aattgcaaaa cttgggtcaa aagccataga     120
atctcctctt ctgataggat tctgttcagc ctgggcatca ccaggtttct tatgctggga     180
ctatttctgg tgaacaccat ctacttcgtc tcttcaaata cggaaaggtc agtctacctg     240 tctgctttt tgtgttgtg tttcatgttt tggactcga gcagtgtctg gtttgtgacc         300
ttgctcaata tcttgtactg tgtgaagatt actaacttcc aacactcagt gtttctcctg     360
ctgaagcgga atatctcccc aaagatcccc aggctgctgc tggcctgtgt gctgatttct     420
gctttcacca cttgcctgta catcacgctt agccaggcat caccttttcc tgaacttgtg     480
actacgagaa ataacacatc atttaatatc agtgagggca tcttgtcttt agtggtttct     540
ttggtcttga gctcatctct ccagttcatc attaatgtga cttctgcttc cttgctaata     600
cactccttga ggagacatat acagaagatg cagaaaaatg ccactggttt ctggaatccc     660
cagacggaag ctcatgtagg tgctatgaag ctgatggtct atttcctcat cctctacatt     720
ccatattcag ttgctaccct ggtccagtat ctccccttt tatgcaggga tggatatgggg     780 accaaatcca tttgtctgat ttttgccacc ctttactctc caggacattc tgttctcatt     840
attatcacac atcctaaact gaaaacaaca gcaagaaga ttctttgttt caaaaaa        897

<210> SEQ ID NO 4
<211> LENGTH: 299
<212> TYPE: PRT
<213> ORGANISM: Homo sapiens

<400> SEQUENCE: 4

Met Leu Arg Leu Phe Tyr Phe Ser Ala Ile Ile Ala Ser Val Ile Leu
1               5                   10                  15

Asn Phe Val Gly Ile Ile Met Asn Leu Phe Ile Thr Val Val Asn Cys
            20                  25                  30

Lys Thr Trp Val Lys Ser His Arg Ile Ser Ser Asp Arg Ile Leu
        35                  40                  45

Phe Ser Leu Gly Ile Thr Arg Phe Leu Met Leu Gly Leu Phe Leu Val
    50                  55                  60

Asn Thr Ile Tyr Phe Val Ser Ser Asn Thr Glu Arg Ser Val Tyr Leu
65                  70                  75                  80

Ser Ala Phe Phe Val Leu Cys Phe Met Phe Leu Asp Ser Ser Ser Val
                85                  90                  95

Trp Phe Val Thr Leu Leu Asn Ile Leu Tyr Cys Val Lys Ile Thr Asn
            100                 105                 110

Phe Gln His Ser Val Phe Leu Leu Lys Arg Asn Ile Ser Pro Lys
        115                 120                 125

Ile Pro Arg Leu Leu Leu Ala Cys Val Leu Ile Ser Ala Phe Thr Thr
    130                 135                 140

Cys Leu Tyr Ile Thr Leu Ser Gln Ala Ser Pro Phe Pro Glu Leu Val
145                 150                 155                 160

Thr Thr Arg Asn Asn Thr Ser Phe Asn Ile Ser Glu Gly Ile Leu Ser
                165                 170                 175

Leu Val Val Ser Leu Val Leu Ser Ser Leu Gln Phe Ile Ile Asn
            180                 185                 190

Val Thr Ser Ala Ser Leu Leu Ile His Ser Leu Arg Arg His Ile Gln
        195                 200                 205

Lys Met Gln Lys Asn Ala Thr Gly Phe Trp Asn Pro Gln Thr Glu Ala
```

```
                210                 215                 220
His Val Gly Ala Met Lys Leu Met Val Tyr Phe Leu Ile Leu Tyr Ile
225                 230                 235                 240

Pro Tyr Ser Val Ala Thr Leu Val Gln Tyr Leu Pro Phe Tyr Ala Gly
                245                 250                 255

Met Asp Met Gly Thr Lys Ser Ile Cys Leu Ile Phe Ala Thr Leu Tyr
                260                 265                 270

Ser Pro Gly His Ser Val Leu Ile Ile Ile Thr His Pro Lys Leu Lys
                275                 280                 285

Thr Thr Ala Lys Lys Ile Leu Cys Phe Lys Lys
                290                 295

<210> SEQ ID NO 5
<211> LENGTH: 927
<212> TYPE: DNA
<213> ORGANISM: Homo sapiens

<400> SEQUENCE: 5
atgataactt ttctacccat catttttcc agtctggtag tggttacatt tgttattgga        60
aattttgcta atggcttcat agcactggta aattccattg agtcgttcaa gagacaaaag     120 atctccttg ctgaccaaat tctcactgct ctggcggtct ccagagttgg tttgctctgg     180
gtattattat taaactggta ttcaactgtg ttgaatccag cttttaatag tgtagaagta     240
agaactactg cttataatat ctgggcagtg atcaaccatt tcagcaactg gcttgctact     300
accctcagca tattttattt gctcaagatt gccaatttct ccaactttat ttttcttcac     360
ttaaagagga gagttaagag tgtcattctg gtgatgttgt tggggccttt gctatttttg     420
gcttgtcatc tttttgtgat aaacatgaat gagattgtgc ggacaaaaga atttgaagga     480
aacatgactt ggaagatcaa attgaagagt gcaatgtact tttcaaatat gactgtaacc     540
atggtagcaa acttagtacc cttcactctg accctactat ctttatgct gttaatctgt     600 tctttgtgta acatctcaa gaagatgcag ctccgtggta aaggatctca agatcccagc     660
acgaaggtcc acataaaagc tttgcaaact gtgatctcct tcctcttgtt atgtgccatt     720
tactttctgt ccataatgat atcagttggg agttttggaa gtctggaaaa caaacctgtc     780
ttcatgttct gcaaagctat tagattcagc tatccttcaa tccacccatt catcctgatt     840
tggggaaaca agaagctaaa gcagactttt ctttcagttt tttggcaaat gaggtactgg     900
gtgaaaggag agaagacttc atctcca                                         927

<210> SEQ ID NO 6
<211> LENGTH: 309
<212> TYPE: PRT
<213> ORGANISM: Homo sapiens

<400> SEQUENCE: 6

Met Ile Thr Phe Leu Pro Ile Ile Phe Ser Ser Leu Val Val Thr
1               5                   10                  15

Phe Val Ile Gly Asn Phe Ala Asn Gly Phe Ile Ala Leu Val Asn Ser
                20                  25                  30

Ile Glu Ser Phe Lys Arg Gln Lys Ile Ser Phe Ala Asp Gln Ile Leu
            35                  40                  45

Thr Ala Leu Ala Val Ser Arg Val Gly Leu Leu Trp Val Leu Leu
        50                  55                  60

Asn Trp Tyr Ser Thr Val Leu Asn Pro Ala Phe Asn Ser Val Glu Val
65                  70                  75                  80
```

Arg Thr Thr Ala Tyr Asn Ile Trp Ala Val Ile Asn His Phe Ser Asn
                85                  90                  95

Trp Leu Ala Thr Thr Leu Ser Ile Phe Tyr Leu Leu Lys Ile Ala Asn
            100                 105                 110

Phe Ser Asn Phe Ile Phe Leu His Leu Lys Arg Arg Val Lys Ser Val
        115                 120                 125

Ile Leu Val Met Leu Leu Gly Pro Leu Leu Phe Leu Ala Cys His Leu
    130                 135                 140

Phe Val Ile Asn Met Asn Glu Ile Val Arg Thr Lys Glu Phe Glu Gly
145                 150                 155                 160

Asn Met Thr Trp Lys Ile Lys Leu Lys Ser Ala Met Tyr Phe Ser Asn
                165                 170                 175

Met Thr Val Thr Met Val Ala Asn Leu Val Pro Phe Thr Leu Thr Leu
            180                 185                 190

Leu Ser Phe Met Leu Leu Ile Cys Ser Leu Cys Lys His Leu Lys Lys
        195                 200                 205

Met Gln Leu Arg Gly Lys Gly Ser Gln Asp Pro Ser Thr Lys Val His
    210                 215                 220

Ile Lys Ala Leu Gln Thr Val Ile Ser Phe Leu Leu Leu Cys Ala Ile
225                 230                 235                 240

Tyr Phe Leu Ser Ile Met Ile Ser Val Trp Ser Phe Gly Ser Leu Glu
                245                 250                 255

Asn Lys Pro Val Phe Met Phe Cys Lys Ala Ile Arg Phe Ser Tyr Pro
            260                 265                 270

Ser Ile His Pro Phe Ile Leu Ile Trp Gly Asn Lys Lys Leu Lys Gln
        275                 280                 285

Thr Phe Leu Ser Val Phe Trp Gln Met Arg Tyr Trp Val Lys Gly Glu
    290                 295                 300

Lys Thr Ser Ser Pro
305

<210> SEQ ID NO 7
<211> LENGTH: 927
<212> TYPE: DNA
<213> ORGANISM: Homo sapiens

<400> SEQUENCE: 7
atgacaactt ttatacccat catttttttcc agtgtggtag tggttctatt tgttattgga      60
aattttgcta atggcttcat agcattggta aattccattg agcgggtcaa gagacaaaag     120
atctcttttg ctgaccagat tctcactgct ctggcggtct ccagagttgg tttgctctgg     180
gtattattat taaattggta ttcaactgtg tttaatccag cttttttatag tgtagaagta     240 agaactactg cttataatgt ctgggcagta accggccatt tcagcaactg gcttgctact     300
agcctcagca tatttttattt gctcaagatt gccaatttct ccaaccttat ttttcttcac     360
ttaaagagga gagttaagag tgtcattctg gtgatgctgt ggggcctttt actattttttg     420 gcttgtcaac ttttttgtgat aaacatgaaa gagattgtac ggacaaaaga atatgaagga     480 acatgactt ggaagatcaa attgaggagt gcagtgtacc tttcagatgc gactgtaacc     540
acgctaggaa acttagtgcc cttcactctg accctgctat gttttttgct gttaatctgt     600
tctctgtgta aacatctcaa gaagatgcag ctccatggta aaggatctca agatcccagc     660
accaaggtcc acataaaagc tttgcaaact gtgatctttt tcctcttgtt atgtgccgtt     720
tactttctgt ccataatgat atcagttggg agttttggga gtctggaaaa caaacctgtc     780
ttcatgttct gcaaagctat tagattcagc tatccttcaa tccacccatt catcctgatt     840

```
tggggaaaca agaagctaaa gcagactttt ctttcagttt tgcggcaagt gaggtactgg      900
gtgaaaggag agaagccttc atctcca                                          927
```

<210> SEQ ID NO 8
<211> LENGTH: 309
<212> TYPE: PRT
<213> ORGANISM: Homo sapiens

<400> SEQUENCE: 8

```
Met Thr Thr Phe Ile Pro Ile Ile Phe Ser Ser Val Val Val Leu
1               5                  10                  15

Phe Val Ile Gly Asn Phe Ala Asn Gly Phe Ile Ala Leu Val Asn Ser
            20                  25                  30

Ile Glu Arg Val Lys Arg Gln Lys Ile Ser Phe Ala Asp Gln Ile Leu
        35                  40                  45

Thr Ala Leu Ala Val Ser Arg Val Gly Leu Leu Trp Val Leu Leu Leu
    50                  55                  60

Asn Trp Tyr Ser Thr Val Phe Asn Pro Ala Phe Tyr Ser Val Glu Val
65                  70                  75                  80

Arg Thr Thr Ala Tyr Asn Val Trp Ala Val Thr Gly His Phe Ser Asn
                85                  90                  95

Trp Leu Ala Thr Ser Leu Ser Ile Phe Tyr Leu Leu Lys Ile Ala Asn
            100                 105                 110

Phe Ser Asn Leu Ile Phe Leu His Leu Lys Arg Arg Val Lys Ser Val
        115                 120                 125

Ile Leu Val Met Leu Leu Gly Pro Leu Leu Phe Leu Ala Cys Gln Leu
    130                 135                 140

Phe Val Ile Asn Met Lys Glu Ile Val Arg Thr Lys Glu Tyr Glu Gly
145                 150                 155                 160

Asn Met Thr Trp Lys Ile Lys Leu Arg Ser Ala Val Tyr Leu Ser Asp
                165                 170                 175

Ala Thr Val Thr Thr Leu Gly Asn Leu Val Pro Phe Thr Leu Thr Leu
            180                 185                 190

Leu Cys Phe Leu Leu Leu Ile Cys Ser Leu Cys Lys His Leu Lys Lys
        195                 200                 205

Met Gln Leu His Gly Lys Gly Ser Gln Asp Pro Ser Thr Lys Val His
    210                 215                 220

Ile Lys Ala Leu Gln Thr Val Ile Phe Phe Leu Leu Leu Cys Ala Val
225                 230                 235                 240

Tyr Phe Leu Ser Ile Met Ile Ser Val Trp Ser Phe Gly Ser Leu Glu
                245                 250                 255

Asn Lys Pro Val Phe Met Phe Cys Lys Ala Ile Arg Phe Ser Tyr Pro
            260                 265                 270

Ser Ile His Pro Phe Ile Leu Ile Trp Gly Asn Lys Lys Leu Lys Gln
        275                 280                 285

Thr Phe Leu Ser Val Leu Arg Gln Val Arg Tyr Trp Val Lys Gly Glu
    290                 295                 300

Lys Pro Ser Ser Pro
305
```

<210> SEQ ID NO 9
<211> LENGTH: 927
<212> TYPE: DNA
<213> ORGANISM: Homo sapiens

<400> SEQUENCE: 9

```
atgataactt tcctgcccat cattttttcc attctaatag tggttacatt tgtgattgga    60
aattttgcta atggcttcat agcattggta aattccattg agtggtttaa gagacaaaag   120
atctcttttg ctgaccaaat tctcactgct ctggcagtct ccagagttgg tttactctgg   180
gtattagtat taaattggta tgcaactgag ttgaatccag cttttaacag tatagaagta   240
agaattactg cttacaatgt ctgggcagta atcaaccatt tcagcaactg gcttgctact   300
agcctcagca tattttattt gctcaagatt gccaatttct ccaaccttat ttttcttcac   360
ttaaagagga gagttaagag tgttgttctg gtgatactat ggggcctttt gctattttg    420
gtttgtcatc ttttttgtgat aaacatgaat cagattatat ggacaaaaga atatgaagga   480
aacatgactt ggaagatcaa actgaggagt gcaatgtacc tttcaaatac aacggtaacc   540
atcctagcaa acttagttcc cttcactctg accctgatat cttttctgct gttaatctgt   600
tctctgtgta acatctcaaa aagatgcag ctccatggca aaggatctca agatcccagc    660
atgaaggtcc acataaaagc tttgcaaact gtgacctcct tcctcttgtt atgtgccatt   720
tactttctgt ccataatcat gtcagtttgg agttttgaga gtctggaaaa caaacctgtc   780
ttcatgttct gcgaagctat tgcattcagc tatccttcaa cccacccatt catcctgatt   840
tggggaaaca agaagctaaa gcagactttt cttcagtttt gtggcatgt gaggtactgg   900
gtgaaaggag agaagccttc atcttca                                       927

<210> SEQ ID NO 10
<211> LENGTH: 309
<212> TYPE: PRT
<213> ORGANISM: Homo sapiens

<400> SEQUENCE: 10

Met Ile Thr Phe Leu Pro Ile Ile Phe Ser Ile Leu Ile Val Val Thr
1               5                   10                  15

Phe Val Ile Gly Asn Phe Ala Asn Gly Phe Ile Ala Leu Val Asn Ser
            20                  25                  30

Ile Glu Trp Phe Lys Arg Gln Lys Ile Ser Phe Ala Asp Gln Ile Leu
        35                  40                  45

Thr Ala Leu Ala Val Ser Arg Val Gly Leu Leu Trp Val Leu Val Leu
    50                  55                  60

Asn Trp Tyr Ala Thr Glu Leu Asn Pro Ala Phe Asn Ser Ile Glu Val
65                  70                  75                  80

Arg Ile Thr Ala Tyr Asn Val Trp Ala Val Ile Asn His Phe Ser Asn
                85                  90                  95

Trp Leu Ala Thr Ser Leu Ser Ile Phe Tyr Leu Leu Lys Ile Ala Asn
            100                 105                 110

Phe Ser Asn Leu Ile Phe Leu His Leu Lys Arg Arg Val Lys Ser Val
        115                 120                 125

Val Leu Val Ile Leu Leu Gly Pro Leu Leu Phe Leu Val Cys His Leu
    130                 135                 140

Phe Val Ile Asn Met Asn Gln Ile Ile Trp Thr Lys Glu Tyr Glu Gly
145                 150                 155                 160

Asn Met Thr Trp Lys Ile Lys Leu Arg Ser Ala Met Tyr Leu Ser Asn
                165                 170                 175

Thr Thr Val Thr Ile Leu Ala Asn Leu Val Pro Phe Thr Leu Thr Leu
            180                 185                 190

Ile Ser Phe Leu Leu Leu Ile Cys Ser Leu Cys Lys His Leu Lys Lys
        195                 200                 205
```

-continued

```
Met Gln Leu His Gly Lys Gly Ser Gln Asp Pro Ser Met Lys Val His
            210                 215                 220

Ile Lys Ala Leu Gln Thr Val Thr Ser Phe Leu Leu Cys Ala Ile
225                 230                 235                 240

Tyr Phe Leu Ser Ile Ile Met Ser Val Trp Ser Phe Glu Ser Leu Glu
                245                 250                 255

Asn Lys Pro Val Phe Met Phe Cys Glu Ala Ile Ala Phe Ser Tyr Pro
            260                 265                 270

Ser Thr His Pro Phe Ile Leu Ile Trp Gly Asn Lys Lys Leu Lys Gln
        275                 280                 285

Thr Phe Leu Ser Val Leu Trp His Val Arg Tyr Trp Val Lys Gly Glu
    290                 295                 300

Lys Pro Ser Ser Ser
305
```

<210> SEQ ID NO 11
<211> LENGTH: 960
<212> TYPE: DNA
<213> ORGANISM: Homo sapiens

<400> SEQUENCE: 11

```
atgataactt ttctgcccat cattttttcc attctaatag tggttatatt tgttattgga      60
aattttgcta atggcttcat agcattggta aattccattg agtgggtcaa gagacaaaag     120
atctcctttg ttgaccaaat tctcactgct ctggcggtct ccagagttgg tttgctctgg     180
gtgttattac tacattggta tgcaactcag ttgaatccag ctttttatag tgtagaagta     240
agaattactg cttataatgt ctgggcagta accaaccatt tcagcagctg gcttgctact     300
agcctcagca tgtttttattt gctcaggatt gccaatttct ccaaccttat ttttcttcgc     360
ataaagagga gagttaagag tgttgttctg gtgatactgt ggggcctttt gctattttg      420
gtttgtcatc tttttgtgat aaacatggat gagactgtat ggacaaaaga atatgaagga     480
aacgtgactt ggaagatcaa attgaggagt gcaatgtacc attcaaatat gactctaacc     540
atgctagcaa actttgtacc cctcactctg accctgatat cttttctgct gttaatctgt     600
tctctgtgta acatctcaa gaagatgcag ctccatggca aaggatctca agatcccagc      660
accaaggtcc acataaaagc tttgcaaact gtgacctcct tcttctgtt atgtgccatt       720
tactttctgt ccatgatcat atcagtttgt aattttggga ggctggaaaa gcaacctgtc     780
ttcatgttct gccaagctat tatattcagc tatccttcaa cccacccatt catcctgatt     840
tgggaaaaca agaagctaaa gcagattttt ctttcagttt tgcggcatgt gaggtactgg    900
gtgaaagaca gaagccttcg tctccataga ttcacaagag ggcattgtg tgtcttctag     960
```

<210> SEQ ID NO 12
<211> LENGTH: 319
<212> TYPE: PRT
<213> ORGANISM: Homo sapiens

<400> SEQUENCE: 12

```
Met Ile Thr Phe Leu Pro Ile Ile Phe Ser Ile Leu Ile Val Val Ile
1               5                   10                  15

Phe Val Ile Gly Asn Phe Ala Asn Gly Phe Ile Ala Leu Val Asn Ser
            20                  25                  30

Ile Glu Trp Val Lys Arg Gln Lys Ile Ser Phe Val Asp Gln Ile Leu
        35                  40                  45

Thr Ala Leu Ala Val Ser Arg Val Gly Leu Leu Trp Val Leu Leu Leu
    50                  55                  60
```

| | | | | | | | | | | | | | | | |
|---|---|---|---|---|---|---|---|---|---|---|---|---|---|---|---|
|His|Trp|Tyr|Ala|Thr|Gln|Leu|Asn|Pro|Ala|Phe|Tyr|Ser|Val|Glu|Val|
|65| | | |70| | | |75| | | |80| | | |

Arg Ile Thr Ala Tyr Asn Val Trp Ala Val Thr Asn His Phe Ser Ser
                85                  90                  95

Trp Leu Ala Thr Ser Leu Ser Met Phe Tyr Leu Leu Arg Ile Ala Asn
            100                 105                 110

Phe Ser Asn Leu Ile Phe Leu Arg Ile Lys Arg Val Lys Ser Val
        115                 120                 125

Val Leu Val Ile Leu Leu Gly Pro Leu Leu Phe Leu Val Cys His Leu
130                 135                 140

Phe Val Ile Asn Met Asp Glu Thr Val Trp Thr Lys Glu Tyr Glu Gly
145                 150                 155                 160

Asn Val Thr Trp Lys Ile Lys Leu Arg Ser Ala Met Tyr His Ser Asn
                165                 170                 175

Met Thr Leu Thr Met Leu Ala Asn Phe Val Pro Leu Thr Leu Thr Leu
            180                 185                 190

Ile Ser Phe Leu Leu Leu Ile Cys Ser Leu Cys Lys His Leu Lys Lys
        195                 200                 205

Met Gln Leu His Gly Lys Gly Ser Gln Asp Pro Ser Thr Lys Val His
    210                 215                 220

Ile Lys Ala Leu Gln Thr Val Thr Ser Phe Leu Leu Cys Ala Ile
225                 230                 235                 240

Tyr Phe Leu Ser Met Ile Ile Ser Val Cys Asn Pro Gly Arg Leu Glu
                245                 250                 255

Lys Gln Pro Val Phe Met Phe Cys Gln Ala Ile Ile Phe Ser Tyr Pro
            260                 265                 270

Ser Thr His Pro Phe Ile Leu Ile Leu Gly Asn Lys Lys Leu Lys Gln
        275                 280                 285

Ile Phe Leu Ser Val Leu Arg His Val Arg Tyr Trp Val Lys Asp Arg
    290                 295                 300

Ser Leu Arg Leu His Arg Phe Thr Arg Gly Ala Leu Cys Val Phe
305                 310                 315

<210> SEQ ID NO 13
<211> LENGTH: 969
<212> TYPE: DNA
<213> ORGANISM: Homo sapiens

<400> SEQUENCE: 13

```
atggcaacgg tgaacacaga tgccacagat aaagacatat ccaagttcaa ggtcaccttc    60
actttggtgg tctccggaat agagtgcatc actggcatcc ttgggagtgg cttcatcacg   120
gccatctatg gggctgagtg ggccaggggc aaaacactcc ccactggtga ccgcattatg   180
ttgatgctga gcttttccag gctcttgcta cagatttgga tgatgctgga gaacattttc   240
agtctgctat tccgaattgt ttataaccaa aactcagtgt atatcctctt caaagtcatc   300
actgtctttc tgaaccattc caatctctgg tttgctgcct ggctcaaagt cttctattgt   360
cttagaattg caaacttcaa tcatcctttg ttcttcctga tgaagaggaa aatcatagtg   420
ctgatgcctt ggcttctcag gctgtcagtg ttggtttcct taagcttcag ctttcctctc   480
tcgagagatg tcttcaatgt gtatgtgaat agctccattc ctatcccctc ctccaactcc   540
acggagaaga agtacttctc tgagaccaat atggtcaacc tggtattttt ctataacatg   600
gggatcttcg ttcctctgat catgttcatc ctggcagcca cctgctgat cctctctctc   660 aagagacaca ccctacacat gggaagcaat gccacaggt ccagggaccc cagcatgaag   720
```

```
gctcacatag gggccatcaa agccaccagc tactttctca tcctctacat tttcaatgca    780
attgctctat ttctttccac gtccaacatc tttgacactt acagttcctg gaatattttg    840
tgcaagatca tcatggctgc ctaccctgcc ggccactcag tacaactgat cttgggcaac    900
cctgggctga agagcctg gaagcggttt cagcaccaag ttcctcttta cctaaaaggg    960
cagactctg                                                             969
```

<210> SEQ ID NO 14
<211> LENGTH: 323
<212> TYPE: PRT
<213> ORGANISM: Homo sapiens

<400> SEQUENCE: 14

```
Met Ala Thr Val Asn Thr Asp Ala Thr Lys Asp Ile Ser Lys Phe
1               5                   10                  15

Lys Val Thr Phe Thr Leu Val Val Ser Gly Ile Glu Cys Ile Thr Gly
            20                  25                  30

Ile Leu Gly Ser Gly Phe Ile Thr Ala Ile Tyr Gly Ala Glu Trp Ala
        35                  40                  45

Arg Gly Lys Thr Leu Pro Thr Gly Asp Arg Ile Met Leu Met Leu Ser
    50                  55                  60

Phe Ser Arg Leu Leu Leu Gln Ile Trp Met Met Leu Glu Asn Ile Phe
65                  70                  75                  80

Ser Leu Leu Phe Arg Ile Val Tyr Asn Gln Asn Ser Val Tyr Ile Leu
                85                  90                  95

Phe Lys Val Ile Thr Val Phe Leu Asn His Ser Asn Leu Trp Phe Ala
            100                 105                 110

Ala Trp Leu Lys Val Phe Tyr Cys Leu Arg Ile Ala Asn Phe Asn His
        115                 120                 125

Pro Leu Phe Phe Leu Met Lys Arg Lys Ile Ile Val Leu Met Pro Trp
    130                 135                 140

Leu Leu Arg Leu Ser Val Leu Val Ser Leu Ser Phe Ser Phe Pro Leu
145                 150                 155                 160

Ser Arg Asp Val Phe Asn Val Tyr Val Asn Ser Ile Pro Ile Pro
                165                 170                 175

Ser Ser Asn Ser Thr Glu Lys Lys Tyr Phe Ser Glu Thr Asn Met Val
            180                 185                 190

Asn Leu Val Phe Phe Tyr Asn Met Gly Ile Phe Val Pro Leu Ile Met
        195                 200                 205

Phe Ile Leu Ala Ala Thr Leu Leu Ile Leu Ser Leu Lys Arg His Thr
    210                 215                 220

Leu His Met Gly Ser Asn Ala Thr Gly Ser Arg Asp Pro Ser Met Lys
225                 230                 235                 240

Ala His Ile Gly Ala Ile Lys Ala Thr Ser Tyr Phe Leu Ile Leu Tyr
                245                 250                 255

Ile Phe Asn Ala Ile Ala Leu Phe Leu Ser Thr Ser Asn Ile Phe Asp
            260                 265                 270

Thr Tyr Ser Ser Trp Asn Ile Leu Cys Lys Ile Ile Met Ala Ala Tyr
        275                 280                 285
```

```
Pro Ala Gly His Ser Val Gln Leu Ile Leu Gly Asn Pro Gly Leu Arg
    290                 295                 300

Arg Ala Trp Lys Arg Phe Gln His Gln Val Pro Leu Tyr Leu Lys Gly
305                 310                 315                 320

Gln Thr Leu
```

METHODS OF IDENTIFYING ANTAGONISTS OF THE HTAS2R46 BITTER TASTE RECEPTOR

CROSS REFERENCE TO RELATED APPLICATIONS

This application is a 371 national stage application of International Application No. PCT/EP2010/006563, with an International Filing Date of Oct. 27, 2010, which claims priority to U.S. Application No. 61/255,207, filed on Oct. 27, 2009, both of which are incorporated herein by reference in their entirety.

The present invention relates to antagonists and agonists of the human bitter-taste receptors hTAS2R40, hTAS2R43, hTAS2R44, hTAS2R46, and hTAS2R47. The invention also relates to methods for identifying further molecules that suppress or enhance bitter taste transduction or bitter taste response mediated by hTAS2R40, hTAS2R43, hTAS2R44, hTAS2R46, and/or hTAS2R47 and uses thereof.

BACKGROUND OF THE INVENTION

Investigators have recently turned their attention to understanding the biological mechanisms of taste, and in particular bitter taste. For a review of the literature see, for example, Caicedo A. and Roper S D. (2001) Science 291: 1557-1560; Dulac C. (2000) Cell 100: 607-610; Kinnamon S. C. (2000) Neuron 25: 507-510; Lindemann B. (2001) Nature 413: 219-225.; and Margolskee R F. (2001) J. Biol. Chem. 277: 1-4.

Bitter taste is aversive, and as such provides humans with a mechanism of protection against poisonous substances, which are generally bitter-tasting compounds. More subtly, bitter-tastants also affect the palatability of food, beverages, thereby influencing human nutritional habits as is more fully discussed by Drewnowski in "The Science and Complexity of Bitter Taste", (2001) Nutr. Rev. 59: 163-169. They also affect the palatability of other ingestibles such as orally administered pharmaceuticals and nutraceuticals. Understanding the mechanism of bitter taste transduction has implications for the food and pharmaceutical industries. If the bitter taste transduction pathway can be manipulated, it may be possible to suppress or eliminate bitter taste to render foods more palatable and increase patient compliance with oral pharmaceutics.

Taste transduction involves the interaction of molecules, i.e. tastants with taste receptor-expressing cells which reside in the taste buds located in the papillae of the tongue. Taste buds relay information to the brain on the nutrient content of food and the presence of poisons. Recent advances in biochemical and physiological studies have enabled researchers to conclude that bitter taste transduction is mediated by so-called G-protein coupled receptors (GPCRs). GPCRs are 7 transmembrane domain cell surface proteins that amplify signals generated at a cell surface when the receptor interacts with a ligand (a tastant) whereupon they activate heterotrimeric G-proteins. The G-proteins are protein complexes that are composed of alpha and beta-gamma sub-units. They are usually referred to by their alpha subunits and classified generally into 4 groups: G alpha s, i, q and 12. The G alpha q type couple with GPCRs to activate phospholipase C which leads to an increase in cellular $Ca^{2+}$. There are many Gq-type G-proteins that are promiscuous and can couple to GPCRs, including taste receptors, and these so-called "promiscuous" G-proteins are well known in the art. These G-proteins dissociate into alpha and beta-gamma subunits upon activation, resulting in a complex cascade of cellular events that result in the cell producing second messengers, such as calcium ions, that enable the cells to send a signal to the brain indicating a bitter response.

There is also anatomical evidence that GPCRs mediate bitter taste transduction: clusters of these receptors are found in mammalian taste cells containing gustducin. Gustducin is a G-protein subunit that is implicated in the perception of bitter taste in mammals see, for example, Chandrashekar, J. et al. (2000) Cell 100: 703-711; Matsunami H. et al. (2000) Nature 404: 601-604; or Adler E. et al. (2000) Cell 100: 693-702. cDNAs encoding such GPCRs have been identified, isolated, and used as templates to compare with DNA libraries using in-silico data-mining techniques to identify other related receptors. In this manner it has been possible to identify a family of related receptors, the so-called T2R or TAS2R family of receptors, which have been putatively assigned as bitter taste receptors.

Humans are able to detect with a limited genetic repertoire of about 30 receptor genes thousands of different bitter compounds. Since their discovery in the year 2000 (Adler E. et al. (2000) supra; Chandrashekar J. et al. (2000) supra; Matsunami H. et al (2000) supra) only few mammalian TAS2R5 have been deorphanised, i.e. ligands, in particular agonists have been identified. The murine mTAS2R5 (Chandrashekar J. et al (2000) supra) and the rat rTAS2R9 (Bufe B. et al. (2002) Nature Genetics 32:397-401) respond to the toxic bitter substance cycloheximide, the mouse mTAS2R8 and the human hTAS2R4 respond to high doses of denatonium and, to a lesser extent, to 6-n-propyl-2-thiouracil (Chandrashekar J. et al. (2000) supra), the human hTAS2R10 and hTAS2R16 respond selectively to strychnine and bitter glucopyranosides, respectively (Bufe B. et al (2002) supra). Human hTAS2R46 was characterized as a bitter receptor broadly tuned to sesquiterpene lactones and to clerodane and labdane diterpenoids as well as to the unrelated bitter substances strychnine and denatonium (Brockhoff A. et al., (2007) J. Agric. Food Chem. 55(15): 6236-6243). Although for some TAS2Rs a limited promiscuity (mTAS2R8, hTAS2R4) or specificity for a group of chemically related compounds (hTAS2R16) was reported, the relative selectivity of ligand recognition by the receptors published to date does by far not explain the enormous number of bitter tastants recognised by the mammalian gustatory system. Also very little is known about substances that can act as antagonists of bitter taste receptors and thereby reduce or suppress a bitter taste sensation.

The knowledge about compounds that act as bitter receptor antagonists is prerequisite to the implementation of a method to isolate structurally related antagonists which may be at least as potent in suppressing the bitter taste receptor activity as the original antagonist and which may feature additional advantages such as lower toxicity, better solubility, improved stability and so forth. A bitter taste receptor antagonist isolated by such method can also be isolated and modified or combined with other bitter taste receptor antagonists in such a way that it is capable of targeting a broader range of known bitter taste receptors with high affinity to achieve a more effective suppression of bitter taste.

The present invention provides compounds which act as antagonists for the function of human bitter taste receptors hTAS2R40, hTAS2R43, hTAS2R44, hTAS2R46, and hTAS2R47. The disclosure of the present patent application allows the implementation of a method to isolate additional structurally related antagonists or agonists for these six bitter taste receptors to suppress or to enhance, respectively, bitter taste. Furthermore, the use of such antagonists and agonists is disclosed.

SUMMARY OF THE INVENTION

In a first aspect the present invention relates to a method for identifying an antagonist of hTAS2R40 bitter taste receptor activity, hTAS2R43 bitter taste receptor activity, hTAS2R44 bitter taste receptor activity, hTAS2R46 bitter taste receptor activity, or hTAS2R47 bitter taste receptor activity, wherein the bitter taste receptor is encoded by a polynucleotide selected from the group consisting of:

(a) polynucleotide encoding at least the mature form of the polypeptide having the amino acid sequence as shown in SEQ ID NO: 14, SEQ ID NO: 6, SEQ ID NO: 8, SEQ ID NO: 10, or SEQ ID NO: 12;

(b) polynucleotide having the coding nucleotide sequence as shown in SEQ ID NO: 13, SEQ ID NO: 5, SEQ ID NO: 7, SEQ ID NO: 9, or SEQ ID NO: 11 encoding at least the mature form of the polypeptide;

(c) polynucleotide encoding a fragment or variant of a polypeptide encoded by a polynucleotide of any one of (a) to (b), wherein in said variant one or more amino acid residues are conservatively substituted compared to said polypeptide, and said fragment or derivative has hTAS2R40 bitter taste receptor activity, hTAS2R43 bitter taste receptor activity, hTAS2R44 bitter taste receptor activity, hTAS2R46 bitter taste receptor activity, or hTAS2R47 bitter taste receptor activity;

(d) polynucleotide which is an ortholog of the polynucleotide sequences shown in SEQ ID NO: 13, SEQ ID NO: 5, SEQ ID NO: 7, SEQ ID NO: 9, or SEQ ID NO: 11 encoding at least the mature form of the corresponding bitter taste receptor;

(e) polynucleotide which encodes a polypeptide having hTAS2R40 bitter taste receptor activity, hTAS2R43 bitter taste receptor activity, hTAS2R44 bitter taste receptor activity, hTAS2R46 bitter taste receptor activity, or hTAS2R47 bitter taste receptor activity, and where said polypeptide is at least 80% identical to a polypeptide as shown in SEQ ID NO: 14, SEQ ID NO: 6, SEQ ID NO: 8, SEQ ID NO: 10, or SEQ ID NO: 12; and (f) polynucleotide the complementary strand of which hybridizes under stringent conditions to a polynucleotide as defined in any one of (a) to (e) and which codes for a polypeptide having hTAS2R40 bitter taste receptor activity, hTAS2R43 bitter taste receptor activity, hTAS2R44 bitter taste receptor activity, hTAS2R46 bitter taste receptor activity, or hTAS2R47 bitter taste receptor activity;

comprising the steps:

(1) contacting a bitter taste receptor encoded by said polynucleotide or a host cell genetically engineered with said polynucleotide or with a vector containing said polynucleotide to express said bitter taste receptor with a potential antagonist or with a pharmaceutically acceptable salt thereof, said potential antagonist having a structure according to formula (IV):

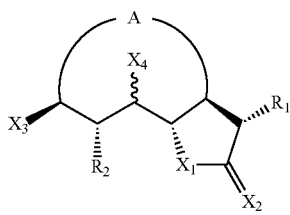

(IV)

wherein $X_1$ is —O—, —S—, or —NH—, preferably —O— or —S—, most preferably —O—;

$X_2$ is =O, =S, or =NH, preferably =O or =S, most preferably =O;

$X_3$ is —OH, —SH, —NH$_2$, —NO$_2$, —CN, —COOH, =O, =S, =NH, —O—CH$_3$, —S—CH$_3$, or —NH—CH$_3$, preferably —OH, —SH, —NH$_2$, —NO$_2$, —CN, —COOH, =O, =S, or =NH, more preferably —OH, —SH, =O, or =S, even more preferably —OH or —SH, most preferably —OH;

$X_4$ is selected from the group consisting of hydrogen, $C_1$ to $C_4$ alkyl, $C_1$ to $C_4$ alkenyl, $C_2$ to $C_4$ alkynyl, $C_1$ to $C_3$ alkoxy, $C_1$ to $C_3$ heteroalkyl, $C_1$ to $C_3$ heteroalkenyl, and $C_2$ to $C_3$ heteroalkynyl; or $X_4$ forms a single bond to A; preferably $X_4$ is hydrogen or —CH$_3$ or forms a single bond to A; more preferably $X_4$ is hydrogen;

A is selected from the group consisting of straight or branched $C_4$ to $C_7$ alkyl, straight or branched $C_4$ to $C_7$ alkenyl, straight or branched $C_4$ to $C_7$ alkynyl, straight or branched $C_3$ to $C_6$ heteroalkyl, straight or branched $C_3$ to $C_6$ heteroalkenyl, and straight or branched $C_3$ to $C_6$ heteroalkynyl, wherein said alkyl, alkenyl, alkynyl, heteroalkyl, heteroalkenyl, and heteroalkynyl are optionally substituted 1, 2, 3, 4, or 5 times, preferably 1, 2, or 3 times, and more preferably once or twice;

$R_1$ is selected from the group consisting of hydrogen, $C_1$ to $C_4$ alkyl, $C_1$ to $C_4$ alkenyl, $C_2$ to $C_4$ alkynyl, $C_1$ to $C_3$ alkoxy, $C_1$ to $C_3$ heteroalkyl, $C_1$ to $C_3$ heteroalkenyl, and $C_2$ to $C_3$ heteroalkynyl, wherein said alkyl, alkenyl, alkynyl, alkoxy, heteroalkyl, heteroalkenyl, and heteroalkynyl are optionally substituted once or twice; preferably $R_1$ is —CH$_3$ or =CH$_2$ or hydrogen, more preferably —CH$_3$ or =CH$_2$;

$R_2$ is selected from the group consisting of hydrogen, $C_1$ to $C_4$ alkyl, $C_1$ to $C_4$ alkenyl, $C_2$ to $C_4$ alkynyl, $C_1$ to $C_3$ alkoxy, $C_1$ to $C_3$ heteroalkyl, $C_1$ to $C_3$ heteroalkenyl, and $C_2$ to $C_3$ heteroalkynyl, wherein said alkyl, alkenyl, alkynyl, alkoxy, heteroalkyl, heteroalkenyl, and heteroalkynyl are optionally substituted once or twice; preferably $R_2$ is —CH$_3$ or hydrogen, more preferably —CH$_3$;

and (2) determining whether the potential antagonist inhibits the bitter taste receptor activity;

wherein prior to, concomitantly with and/or after step (1) said bitter taste receptor or said host cell is contacted with an agonist of bitter taste receptor hTAS2R40, bitter taste receptor hTAS2R43, bitter taste receptor hTAS2R44, bitter taste receptor hTAS2R46, or bitter taste receptor hTAS2R47.

In a second aspect the present invention relates to a method for identifying an antagonist of hTAS2R40 bitter taste receptor activity, hTAS2R43 bitter taste receptor activity, hTAS2R46 bitter taste receptor activity, or hTAS2R47 bitter taste receptor activity, wherein the bitter taste receptor is encoded by a polynucleotide selected from the group consisting of:

(a) polynucleotide encoding at least the mature form of the polypeptide having the amino acid sequence as shown in SEQ ID NO: 14, SEQ ID NO: 6, SEQ ID NO: 10, or SEQ ID NO: 12;

(b) polynucleotide having the coding nucleotide sequence as shown in SEQ ID NO: 13, SEQ ID NO: 5, SEQ ID NO: 9, or SEQ ID NO: 11 encoding at least the mature form of the polypeptide;

(c) polynucleotide encoding a fragment or variant of a polypeptide encoded by a polynucleotide of any one of (a) to (b), wherein in said variant one or more amino acid residues are conservatively substituted compared to said polypeptide, and said fragment or derivative has hTAS2R40 bitter taste receptor activity, hTAS2R43 bitter taste receptor activity, hTAS2R46 bitter taste receptor activity, or hTAS2R47 bitter taste receptor activity;

(d) polynucleotide which is an ortholog of the polynucleotide sequences shown in SEQ ID NO: 13, SEQ ID NO: 5, SEQ ID NO: 9, or SEQ ID NO: 11 encoding at least the mature form of the corresponding bitter taste receptor;

(e) polynucleotide which encodes a polypeptide having hTAS2R40 bitter taste receptor activity, hTAS2R43 bitter taste receptor activity, hTAS2R46 bitter taste receptor activity, or hTAS2R47 bitter taste receptor activity, and where said polypeptide is at least 80% identical to a polypeptide as shown in SEQ ID NO: 6, SEQ ID NO: 10, or SEQ ID NO: 12; and (f) polynucleotide the complementary strand of which hybridizes under stringent conditions to a polynucleotide as defined in any one of (a) to (e) and which codes for a polypeptide having hTAS2R40 bitter taste receptor activity, hTAS2R43 bitter taste receptor activity, hTAS2R46 bitter taste receptor activity, or hTAS2R47 bitter taste receptor activity;

comprising the steps:

(1) contacting a bitter taste receptor encoded by said polynucleotide or a host cell genetically engineered with said polynucleotide or with a vector containing said polynucleotide to express said bitter taste receptor with a potential antagonist or with a pharmaceutically acceptable salt thereof, said potential antagonist having a structure according to formula (III):

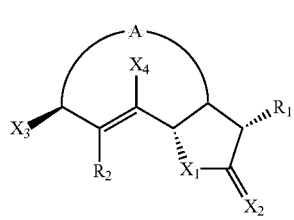

(III)

wherein
$X_1$ is —O—, —S—, or —NH—, preferably —O— or —S—, most preferably —O—;
$X_2$ is =O, =S, or =NH, preferably =O or =S, most preferably =O;
$X_3$ is —OH, —SH, —NH$_2$, —NO$_2$, —CN, —COOH, =O, =S, =NH, —O—CH$_3$, —S—CH$_3$, or —NH—CH$_3$; preferably —OH, —SH, —NH$_2$, —NO$_2$, —CN, —COOH, =O, =S, or =NH, more preferably —OH, —SH, =O, or even more preferably —OH or —SH, most preferably —OH;
$X_4$ is selected from the group consisting of hydrogen, $C_1$ to $C_4$ alkyl, $C_2$ to $C_4$ alkenyl, $C_2$ to $C_4$ alkynyl, $C_1$ to $C_3$ alkoxy, $C_1$ to $C_3$ heteroalkyl, $C_2$ to $C_3$ heteroalkenyl, and $C_2$ to $C_3$ heteroalkynyl; or $X_4$ forms a single bond to A; preferably $X_4$ is hydrogen or —CH$_3$ or forms a single bond to A; more preferably $X_4$ is hydrogen;
A is selected from the group consisting of $C_4$ to $C_7$ alkyl, $C_4$ to $C_7$ alkenyl, $C_4$ to $C_7$ alkynyl, $C_3$ to $C_6$ heteroalkyl, $C_3$ to $C_6$ heteroalkenyl, and $C_3$ to $C_6$ heteroalkynyl, wherein said alkyl, alkenyl, alkynyl, heteroalkyl, heteroalkenyl, and heteroalkynyl are optionally substituted 1, 2, 3, 4, or 5 times, preferably 1, 2, or 3 times, and more preferably once or twice;

$R_1$ is selected from the group consisting of hydrogen, $C_1$ to $C_4$ alkyl, $C_1$ to $C_4$ alkenyl, $C_2$ to $C_4$ alkynyl, $C_1$ to $C_3$ alkoxy, $C_1$ to $C_3$ heteroalkyl, $C_1$ to $C_3$ heteroalkenyl, and $C_2$ to $C_3$ heteroalkynyl, wherein said alkyl, alkenyl, alkynyl, alkoxy, heteroalkyl, heteroalkenyl, and heteroalkynyl are optionally substituted once or twice; preferably $R_1$ is —CH$_3$ or =CH$_2$ or H, more preferably —CH$_3$ or =CH$_2$;
$R_2$ is selected from the group consisting of hydrogen, $C_1$ to $C_4$ alkyl, $C_2$ to $C_4$ alkenyl, $C_2$ to $C_4$ alkynyl, $C_1$ to $C_3$ alkoxy, $C_1$ to $C_3$ heteroalkyl, $C_2$ to $C_3$ heteroalkenyl, and $C_2$ to $C_3$ heteroalkynyl, wherein said alkyl, alkenyl, alkynyl, alkoxy, heteroalkyl, heteroalkenyl, and heteroalkynyl are optionally substituted once or twice; preferably $R_2$ is —CH$_3$ or hydrogen, more preferably —CH$_3$;
and (2) determining whether the potential antagonist inhibits the bitter taste receptor activity;

wherein prior to, concomitantly with and/or after step (1) said bitter taste receptor or said host cell is contacted with an agonist of bitter taste receptor hTAS2R40, bitter taste receptor hTAS2R43, bitter taste receptor hTAS2R46, or bitter taste receptor hTAS2R47.

In a third aspect the present invention relates to a method of isolating an antagonist of hTAS2R40 bitter taste receptor activity, hTAS2R43 bitter taste receptor activity, hTAS2R44 bitter taste receptor activity, hTAS2R46 bitter taste receptor activity, or hTAS2R47 bitter taste receptor activity, the method comprising carrying out the method according to the first or the second aspect and further comprising the step:

(3) isolating a potential antagonist that reduces the activity of hTAS2R40, hTAS2R43, hTAS2R44, hTAS2R46, or hTAS2R47 stimulated by an agonist of hTAS2R40, hTAS2R43, hTAS2R44, hTAS2R46, or hTAS2R47, respectively.

In a fourth aspect the present invention relates to a method for the production of a modified antagonist of hTAS2R40, hTAS2R43, hTAS2R44, hTAS2R46, or hTAS2R47, wherein an antagonist identified in a method according to the first or the second aspect, an antagonist isolated by the method according to the third aspect, 3β hydroxy dihydro costunolide (formula I in FIG. 1), or 3β hydroxy pelenolide (formula II in FIG. 1) is modified by the addition and/or exchange of at least one substituent.

In a fifth aspect the present invention relates to a method for the production of food, a food precursor material or additive employed in the production of foodstuff comprising the step of admixing an antagonist identified by the method according to the first or the second aspect, an antagonist isolated by the method according to the third aspect, the modified antagonist produced according to the method according to the fourth aspect, 3β hydroxy dihydro costunolide (formula I in FIG. 1), 3β hydroxy pelenolide (formula II in FIG. 1) or an antagonist structurally related thereto with foodstuff, a food precursor material or additive employed in the production of foodstuff.

In a sixth aspect the present invention relates to a method for the production of a nutraceutical or pharmaceutical composition comprising the step of admixing the antagonist identified by the method according to the first or the second aspect, an antagonist isolated by the method according to the third aspect, the modified antagonist produced according to the method according to the fourth aspect, 3β hydroxy dihydro costunolide (formula I in FIG. 1), 3β hydroxy pelenolide (formula II in FIG. 1) or an antagonist structurally related thereto with an active agent and optionally with a pharmaceutically acceptable carrier and/or adjuvants.

In a seventh aspect the present invention relates to a foodstuff, any foodstuff precursor material or additive employed in the production of foodstuff producible according to the fifth aspect.

In an eighth aspect the present invention relates to a nutraceutical or pharmaceutical composition producible according to the sixth aspect, comprising at least one nutraceutically or pharmaceutically active agent, and optionally one or more pharmaceutically acceptable carriers and/or adjuvants.

In a ninth aspect the present invention relates to a use of a bitter taste receptor antagonist identified by the method according to the first or the second aspect, a bitter taste receptor antagonist isolated by the method according to the third aspect, a modified bitter taste receptor antagonist producible according to the method according to the fourth aspect, 3β hydroxy dihydro costunolide (formula I in FIG. 1), 3β hydroxy pelenolide (formula II in FIG. 1) or an antagonist structurally related thereto to suppress bitter taste.

This summary of the invention does not necessarily describe all features of the invention.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

In the following definitions of the terms: alkyl, heteroalkyl, cycloalkyl, heterocycloalkyl, alicyclic system, aryl, aralkyl, heteroaryl, heteroaralkyl, alkenyl and alkynyl are provided. In each instance of their use in the remainder of the specification, these terms will have the respectively defined meaning and preferred meanings. The term "alkyl" refers to a saturated straight or branched carbon chain. Preferably, the chain comprises from 1 to 10 carbon atoms, i.e. 1, 2, 3, 4, 5, 6, 7, 8, 9, or 10, e.g. methyl, ethyl, propyl (n-propyl or iso-propyl), butyl (n-butyl, iso-butyl, sec-butyl, or tert-butyl), pentyl, hexyl, heptyl, octyl, nonyl, or decyl. Alkyl groups are optionally substituted.

The term "heteroalkyl" refers to a saturated straight or branched carbon chain. Preferably, the chain comprises from 1 to 9 carbon atoms, i.e. 1, 2, 3, 4, 5, 6, 7, 8, or 9, e.g. methyl, ethyl, propyl (n-propyl or iso-propyl), butyl (n-butyl, iso-butyl, sec-butyl, or tert-butyl), pentyl, hexyl, heptyl, octyl, nonyl, which is interrupted one or more times, e.g. 1, 2, 3, 4, or 5 times, with the same or different heteroatoms. Preferably the heteroatoms are selected from O, S, and N, e.g. —O—$CH_3$, —S—$CH_3$, —NH—$CH_3$, —$CH_2$—O—$CH_3$, —$CH_2$—O—$C_2H_5$, —$CH_2$—S—$CH_3$, —$CH_2$—S—$C_2H_5$, —$CH_2$—NH—$CH_3$, —$CH_2$—NH—$C_2H_5$, —$C_2H_4$—O—$CH_3$, —$C_2H_4$—O—$C_2H_5$, —$C_2H_4$—S—$CH_3$, —$C_2H_4$—S—$C_2H_5$, —$C_2H_4$—NH—$CH_3$, —$C_2H_4$—NH—$C_2H_5$, etc. Heteroalkyl groups are optionally substituted.

The terms "cycloalkyl" and "heterocycloalkyl", by themselves or in combination with other terms, represent, unless otherwise stated, cyclic versions of "alkyl" and "heteroalkyl", respectively, with preferably 3, 4, 5, 6, 7, 8, 9 or 10 atoms forming a ring, e.g. cyclopropyl, cyclobutyl, cyclopentyl, cyclohexyl, cycloheptyl, cyclooctyl, cyclononyl, cyclodecyl. The terms "cycloalkyl" and "heterocycloalkyl" are also meant to include bicyclic, tricyclic and polycyclic versions thereof. If more than one cyclic ring is present such as in bicyclic, tricyclic and polycyclic versions, then these rings may also comprise one or more aryl- or heteroaryl ring. The term "heterocycloalkyl" preferably refers to a saturated ring having five members of which at least one member is a N, O, or S atom and which optionally contains one additional O or one additional N; a saturated ring having six members of which at least one member is a N, O or S atom and which optionally contains one additional O or one additional N or two additional N atoms; or a saturated bicyclic ring having nine or ten members of which at least one member is a N, O or S atom and which optionally contains one or two additional O or one, two, or three additional N atoms. "Cycloalkyl" and "heterocycloalkyl" groups are optionally substituted. Additionally, for heterocycloalkyl, a heteroatom can occupy the position at which the heterocycle is attached to the remainder of the molecule. Preferred examples of cycloalkyl include $C_3$-$C_{10}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, Spiro[3,4]octyl, spiro[4,3]octyl, spiro[3,5]nonyl, Spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantyl, or decahydro-naphthalenyl. Preferred examples of heterocycloalkyl include $C_3$-$C_{10}$-heterocycloalkyl, in particular 1-(1,2,5,6-tetrahydropyridyl), 1-piperidinyl, 2-piperidinyl, 3-piperidinyl, 4-morpholinyl, 3-morpholinyl, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuran-3-yl, tetrahydrothien-2-yl, tetrahydrothien-3-yl, 1-piperazinyl, or 2-piperazinyl.

The term "alicyclic system" refers to mono, bicyclic, tricyclic or polycyclic versions of a cycloalkyl or heterocycloalkyl comprising at least one double and/or triple bond. However, an alicyclic system is not aromatic or heteroaromatic, i.e. does not have a system of conjugated double bonds/free electron pairs. Thus, the number of double and/or triple bonds maximally allowed in an alicyclic system is determined by the number of ring atoms, e.g. in a ring system with up to 5 ring atoms an alicyclic system comprises up to one double bond, in a ring system with 6 ring atoms the alicyclic system comprises up to two double bonds. Accordingly, the "cycloalkenyl" as defined below is a preferred embodiment of an alicyclic ring system. Alicyclic systems are optionally substituted.

The term "alkoxy" refers to an —O-alkyl group, i.e. to an oxygen atom substituted by a saturated straight or branched carbon chain. Preferably, the chain comprises from 1 to 10 carbon atoms, i.e. 1, 2, 3, 4, 5, 6, 7, 8, 9, or 10. Thus, preferred alkoxy groups are methoxy, ethoxy, propoxy (n-propoxy or iso-propoxy), butoxy (n-butoxy, sec-butoxy, iso-butoxy, or tert-butoxy), pentoxy, hexoxy, heptoxy, octoxy, nonoxy, or decoxy. Alkoxy groups are optionally substituted.

The term "aryl" preferably refers to an aromatic monocyclic ring containing 6 carbon atoms, an aromatic bicyclic ring system containing 10 carbon atoms or an aromatic tricyclic ring system containing 14 carbon atoms. Examples are phenyl, naphthyl, anthracenyl, or phenanthrenyl. The aryl group is optionally substituted.

The term "aralkyl" refers to an alkyl moiety, which is substituted by one or more (e.g. 1, 2, 3) aryl, wherein alkyl and aryl have the meaning as outlined above. An example is the benzyl radical. Preferably, in this context the alkyl chain comprises from 1 to 8 carbon atoms, i.e. 1, 2, 3, 4, 5, 6, 7, or 8, e.g. methyl, ethyl, propyl (n-propyl or iso-propyl), butyl (n-butyl, iso-butyl, sec-butyl, or tert-butyl), pentyl, hexyl, heptyl, octyl. Preferably, in this context the alkyl chain is substituted by one or more (e.g. 1, 2, 3) phenyl groups, by one or more (e.g. 1, 2, 3) naphthyl groups, by one or more (e.g. 1, 2, 3) anthracenyl groups, or by one or more (e.g. 1, 2, 3) phenanthrenyl groups. The aralkyl group is optionally substituted at the alkyl and/or aryl part of the group.

The term "heteroaryl" preferably refers to a five or six-membered aromatic monocyclic ring wherein at least one of the carbon atoms are replaced by 1, 2, 3, or 4 (for the five membered ring) or 1, 2, 3, 4, or 5 (for the six-membered ring) of the same or different heteroatoms, preferably selected from O, N and S; an aromatic bicyclic ring system wherein 1, 2, 3, 4, 5, or 6 carbon atoms of the 8, 9, 10, 11 or 12 carbon atoms have been replaced with the same or different heteroatoms, preferably selected from O, N and S; or an aromatic tricyclic ring system wherein 1, 2, 3, 4, 5, or 6 carbon atoms of the 13, 14, 15, or 16 carbon atoms have been replaced with the same or different heteroatoms, preferably selected from O, N and S. Examples are oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, 1-benzothiophenyl, 2-benzothiophenyl, 1H-indazolyl, benzimidazolyl, benzoxazolyl, indoxazinyl, 2,1-benzisoxazoyl, benzothiazolyl, 1,2-benzisothiazolyl, 2,1-benzisothiazolyl, benzotriazolyl, quinolinyl, isoquinolinyl, quinoxalinyl, quinazolinyl, 1,2,3-benzotriazinyl, or 1,2,4-benzotriazinyl.

The term "heteroaralkyl" refers to an alkyl moiety, which is substituted by one or more (e.g. 1, 2, 3) heteroaryl, wherein alkyl and heteroaryl have the meaning as outlined above. An example is the 2-alkylpyridinyl, 3-alkylpyridinyl, or 2-methylpyridinyl. Preferably, in this context the alkyl chain comprises from 1 to 8 carbon atoms, i.e. 1, 2, 3, 4, 5, 6, 7, or 8, e.g. methyl, ethyl, propyl (n-propyl or iso-propyl), butyl (n-butyl, iso-butyl, sec-butyl, or tert-butyl), pentyl, hexyl, heptyl, octyl. The heteroaralkyl group is optionally substituted at the alkyl and/or heteroaryl part of the group.

The terms "alkenyl" and "cycloalkenyl" refer to branched or straight carbon chains containing olefinic unsaturated carbon atoms and to rings with one or more double bonds, respectively. Examples are propenyl and cyclohexenyl. Preferably, the alkenyl chain comprises from 2 to 8 carbon atoms, i.e. 2, 3, 4, 5, 6, 7, or 8, e.g. ethenyl, 1-propenyl, 2-propenyl, iso-propenyl, 1-butenyl, 2-butenyl, 3-butenyl, iso-butenyl, sec-butenyl, tert-butenyl, 1-pentenyl, 2-pentenyl, 3-pentenyl, 4-pentenyl, hexenyl, heptenyl, octenyl. The term "alkenyl" also comprises $=CH_2$, i.e. methenyl, or other alkylidene groups, if the substituent is directly bonded via the double bond. Preferably the cycloalkenyl ring comprises from 3 to 14 carbon atoms, i.e. 3, 4, 5, 6, 7, 8, 9, 10, 11, 12, 13 or 14, e.g. cyclopropenyl, cyclobutenyl, cyclopentenyl, cyclohexenyl, cycloheptenyl, cyclooctenyl, cyclononenyl, cyclodecenyl, spiro[3,3]heptenyl, spiro[3,4]octenyl, spiro[4,3]octenyl, spiro[3,5]nonenyl, spiro[5,3]nonenyl, spiro[3,6]decenyl, spiro[6,3]decenyl, spiro[4,5]decenyl, spiro[5,4]decenyl, bicyclo[4.1.0]heptenyl, bicyclo[3.2.0]heptenyl, bicyclo[2.2.1]heptenyl, bicyclo[2.2.2]octenyl, bicyclo[5.1.0]octenyl, bicyclo[4.2.0]octenyl, hexahydro-pentalenyl, hexahydro-indenyl, octahydro-azulenyl, or octahydro-naphthalenyl.

The term "alkynyl" and "cycloalkynyl" refers to branched or straight carbon chains or rings containing unsaturated carbon atoms with one or more triple bonds. An example is the propargyl radical. Preferably, the alkynyl chain comprises from 2 to 8 carbon atoms, i.e. 2, 3, 4, 5, 6, 7, or 8, e.g. ethynyl, 1-propynyl, 2-propynyl, 1-butynyl, 2-butynyl, 3-butynyl, 1-pentynyl, 2-pentynyl, 3-pentynyl, 4-pentynyl, hexynyl, heptynyl, octynyl.

The term "optionally substituted" in each instance if not further specified refers to halogen (in particular F, Cl, Br, or I), —NO$_2$, —CN, —OR''', —NR'R'', —COOR''', —CONR'R'', —NR'COR'', —NR''COR''', —NR'CONR'R'', —NR'SO$_2$A, —COR'''; —SO$_2$NR'R'', —OOCR''', —CR'''R''''OH, —R'''OH, and -E;

R' and R'' is each independently selected from the group consisting of hydrogen, alkyl, alkenyl, alkynyl, cycloalkyl, heterocycloalkyl, aryl, aralkyl, and heteroaryl or together form a heteroaryl, or heterocycloalkyl;

R''' and R'''' is each independently selected from the group consisting of hydrogen, alkyl, alkenyl, alkynyl, cycloalkyl, heterocycloalkyl, alkoxy, aryl, aralkyl, heteroaryl, and —NR'R'';

E is selected from the group consisting of alkyl, alkenyl, alkynyl, cycloalkyl, alkoxy, alkoxyalkyl, heterocycloalkyl, an alicyclic system, aryl and heteroaryl; optionally substituted.

The terms "polypeptide" and "protein" are used interchangeably herein and mean any peptide-linked chain of amino acids, regardless of length or post-translational modification.

As used herein, the term protein "variant" is to be understood as a polypeptide which differs in comparison to the polypeptide from which it is derived by one or more changes in the amino acid sequence. The polypeptide from which a variant is derived is also known as the parent polypeptide. Typically a variant is constructed artificially, preferably by gene-technological means. Typically, the polypeptide from which the variant is derived is a wild-type protein or wild-type protein domain. However, the variants usable in the present invention may also be derived from homologs, orthologs, or paralogs of the parent polypeptide or from artificially constructed variants, provided that the variant exhibits at least one biological activity of the parent polypeptide. The changes in the amino acid sequence may be amino acid exchanges, insertions, deletions, N-terminal truncations, or C-terminal truncations, or any combination of these changes, which may occur at one or several sites. In preferred embodiments, a variant usable in the present invention exhibits a total number of up to 200 (up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200) changes in the amino acid sequence (i.e. exchanges, insertions, deletions, N-terminal truncations, and/or C-terminal truncations). The amino acid exchanges may be conservative and/or non-conservative. In preferred embodiments, a variant usable in the present invention differs from the protein or domain from which it is derived by up to 1, 2, 3, 4, 5, 6, 7, 8, 9, 10, 15, 20, 25, 30, 35, 40, 45, 50, 55, 60, 65, 70, 75, 80, 85, 90, 95, or 100 amino acid exchanges, preferably conservative amino acid changes. Variants may additionally or alternatively comprise deletions of amino acids, which may be N-terminal truncations, C-terminal truncations or internal deletions or any combination of these. Such variants comprising N-terminal truncations, C-terminal truncations and/or internal deletions are referred to as "deletion variants" or "fragments" in the context of the present application. The terms "deletion variant" and "fragment" are used interchangeably herein. A deletion variant may be naturally occurring (e.g. splice variants) or it may be constructed artificially, preferably by gene-technological means. Typically, the protein or protein domain from which the deletion variant is derived is a wild-type protein. However, the deletion variants of the present invention may also be derived from homologs, orthologs, or paralogs of the parent polypeptide or from artificially constructed variants, provided that the deletion variants exhibit at least one biological activity of the parent polypeptide. Preferably, a deletion variant (or fragment) has a deletion of up to 1, 2, 3, 4, 5, 6, 7, 8, 9, 10, 15, 20, 25, 30, 35, 40, 45, 50, 55, 60, 65, 70, 75, 80, 85, 90, 95, or 100 amino acids at its N-terminus and/or at its C-terminus and/or internally as compared to the parent polypeptide.

A "variant" as used herein, can alternatively or additionally be characterised by a certain degree of sequence identity to the parent polypeptide from which it is derived. More precisely, a variant in the context of the present invention exhibits "at least 80% sequence identity" to its parent polypeptide. Preferably, the sequence identity is over a continuous stretch of 20, 30, 40, 45, 50, 60, 70, 80, 90, 100 or more amino acids.

The expression "at least 80% sequence identity" is used throughout the specification with regard to polypeptide and polynucleotide sequence comparisons. This expression preferably refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide. Preferably, the polypeptide in question and the reference polypeptide exhibit the indicated sequence identity over a continuous stretch of 20, 30, 40, 45, 50, 60, 70, 80, 90, 100 or more amino acids. Preferably, the polynucleotide in question and the reference polynucleotide exhibit the indicated sequence identity over a continuous stretch of 60, 90, 120, 135, 150, 180, 210, 240, 270, 300 or more nucleotides. In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence indicated by SEQ ID, if not specifically indicated otherwise. For example, a peptide sequence consisting of 30 amino acids compared to the amino acids of full length hTAS2R1 according to SEQ ID NO: 2 may exhibit a maximum sequence identity percentage of 10.03% (30/299) while a sequence with a length of 150 amino acids may exhibit a maximum sequence identity percentage of 50.17% (150/299).

The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) *Proc. Natl. Acad. Sci. USA* 90: 5873-5877), with hmmalign (HMMER package, http://hmmer.wustl.edu/) or with the CLUSTAL algorithm (Thompson, J. D., Higgins, D. G. & Gibson, T. J. (1994) *Nucleic Acids Res.* 22, 4673-80) available e.g. on http://www.ebi.ac.uk/Tools/clustalw/ or on http://www.ebi.ac.uk/Tools/clustalw2/index.html or on http://npsa-pbil.ibcp.fr/cgi-bin/npsa_automat.pl?page=/NPSA/npsa_clustalw.html. Preferred parameters used are the default parameters as they are set on http://www.ebi.ac.uk/Tools/clustalw/ or http://www.ebi.ac.uk/Tools/clustalw2/index.html. The grade of sequence identity (sequence matching) may be calculated using e.g. BLAST, BLAT or BlastZ (or BlastX). A similar algorithm is incorporated into the BLASTN and BLASTP programs of Altschul et al. (1990) J. Mol. Biol. 215: 403-410. BLAST polynucleotide searches are performed with the BLASTN program, score=100, word length=12, to obtain polynucleotide sequences that are homologous to those nucleic acids which encode hTAS2R40, hTAS2R43, hTAS2R44, hTAS2R46, or hTAS2R47. BLAST protein searches are performed with the BLASTP program, score=50, word length=3, to obtain amino acid sequences homologous to the hTAS2R40 polypeptide, hTAS2R43 polypeptide, hTAS2R44 polypeptide, hTAS2R46 polypeptide, or hTAS2R47 polypeptide. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:I54-I62) or Markov random fields. When percentages of sequence identity are referred to in the present application, these percentages are calculated in relation to the full length of the longer sequence, if not specifically indicated otherwise.

"Hybridization" can also be used as a measure of sequence identity or homology between two nucleic acid sequences. A nucleic acid sequence encoding hTAS2R40, hTAS2R43, hTAS2R44, hTAS2R46, hTAS2R47, or a portion of any of these can be used as a hybridization probe according to standard hybridization techniques. The hybridization of an hTAS2R40 probe, hTAS2R43 probe, hTAS2R44 probe, hTAS2R46 probe, or hTAS2R47 probe to DNA or RNA from a test source (e.g. a mammalian cell) is an indication of the presence of the hTAS2R40 DNA or RNA, hTAS2R43 DNA or RNA, hTAS2R44 DNA or RNA, hTAS2R46 DNA or RNA, or hTAS2R47 DNA or RNA, respectively, in the test source. Hybridization conditions are known to those skilled in the art and can be found, for example, in Current Protocols in Molecular Biology, John Wiley & Sons, N.Y., 6.3.1-6.3.6, 1991. "Moderate hybridization conditions" are defined as equivalent to hybridization in 2× sodium chloride/sodium citrate (SSC) at 30° C., followed by a wash in 1×SSC, 0.1% SDS at 50° C. "Highly stringent conditions" are defined as equivalent to hybridization in 6× sodium chloride/sodium citrate (SSC) at 45° C., followed by a wash in 0.2×SSC, 0.1% SDS at 65° C.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups:

(1) hydrophobic: Met, Ala, Val, Leu, Ile;
(2) neutral hydrophilic: Cys, Ser, Thr; Asn, Gln;
(3) acidic: Asp, Glu;
(4) basic: His, Lys, Arg;
(5) residues that influence chain orientation: Gly, Pro; and
(6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices. Some preferred conservative substitutions within the above six groups are exchanges within the following sub-groups: (i) Ala, Val, Leu and Ile; (ii) Ser and Thr; (ii) Asn and Gln; (iv) Lys and Arg; and (v) Tyr and Phe. Given the known genetic code, and recombinant and synthetic DNA techniques, the skilled scientist readily can construct DNAs encoding the conservative amino acid variants.

As used herein, "non-conservative substitutions" or "non-conservative amino acid exchanges" are defined as exchanges of an amino acid by another amino acid listed in a different group of the six standard amino acid groups (1) to (6) shown above.

As used herein, the term "derivative" of a polypeptide refers to a polypeptide that has been chemically modified so that it comprises other chemical groups than the 20 naturally occurring amino acids. Examples of such other chemical groups include without limitation glycosylated amino acids and phosphorylated amino acids. The polypeptide from which the derivative derives is also known as the parent polypeptide. This parent polypeptide can be a naturally occurring protein but can also be a protein variant as defined above. Chemical modifications of a polypeptide may provide advantageous properties as compared to the parent polypeptide, e.g. one or more of enhanced stability, increased biological half-life, or increased water solubility. Chemical modifications applicable to the derivatives usable in the present invention include without limitation: PEGylation, glycosylation of non-glycosylated parent polypeptides, or the modification of the glycosylation pattern present in the parent polypeptide.

A "biological activity" as used herein, refers to any activity a polypeptide may exhibit, including without limitation: enzymatic activity; binding activity to another compound (e.g. binding to another polypeptide, in particular binding to a receptor, or binding to a nucleic acid); inhibitory activity (e.g. enzyme inhibitory activity); activating activity (e.g. enzyme-activating activity); or toxic effects. It is not required that the variant or derivative exhibits such an activity to the same extent as the parent polypeptide. A variant is regarded as a variant within the context of the present application, if it exhibits the relevant activity to a degree of at least 10% of the activity of the parent polypeptide. Likewise, a derivative is regarded as a derivative within the context of the present application, if it exhibits the relevant biological activity to a degree of at least 10% of the activity of the parent polypeptide. The relevant "biological activity" in the context of the present invention is "bitter taste receptor activity", i.e. the ability of the receptors described herein (hTAS2R40, hTAS2R43, hTAS2R44, hTAS2R46, and hTAS2R47) to be stimulated by bitter substances, such as the bitter receptor agonists recited herein (e.g. humulone, cohumulone, adhumulone for hTAS2R40; saccharin, aloin, amarogentin for hTAS2R43; aristolochic acids, parthenolide, quinine for hTAS2R44; picrotoxinin, strychnine, absinthin for hTAS2R46; brucine, absinthin, amarogentin for hTAS2R47). Further agonists of hTAS2R40, hTAS2R43, hTAS2R44, hTAS2R46, and hTAS2R47 are listed below in Table 1. Assays for determining "bitter taste receptor activity" of the hTAS2R40 polypeptide, hTAS2R43 polypeptide, hTAS2R44 polypeptide, hTAS2R46 polypeptide, and hTAS2R47 polypeptide are described immediately below and in several other passages of this specification.

One way of detecting "hTAS2R40 bitter taste receptor activity", "hTAS2R43 bitter taste receptor activity", "hTAS2R44 bitter taste receptor activity", "hTAS2R46 bitter taste receptor activity", and/or "hTAS2R47 bitter taste receptor activity" is measuring a change in concentration of an intracellular messenger, e.g. $Ca^{2+}$, $IP_3$, or cAMP. One preferred way of measuring the "bitter taste receptor activity" of any of these receptors, is the ability to release intracellular calcium in a heterologous cell expression system like, for example, (HEK293T/G16gust44) cells that stably expresses a chimeric G-protein consisting of Gα16 and 44 carboxy-terminal amino acids of α-gustducin, in response to bitter tastants, which is dependent on the expression of polypeptides encoded by the polynucleotides of the present invention. The amount of intracellular calcium released can be monitored by, for example, the in vitro FLIPR assay described herein but also by the measurement of one of a variety of other parameters including, for example, $IP_3$ or cAMP level. Additional ways of measuring G-protein coupled receptor activity are known in the art and comprise without limitation electrophysiological methods, transcription assays, which measure, e.g. activation or repression of reporter genes which are coupled to regulatory sequences regulated via the respective G-protein coupled signalling pathway, such reporter proteins comprise, e.g., CAT or LUC; assays measuring internalization of the receptor; or assays in frog melanophore systems, in which pigment movement in melanophores is used as a readout for the activity of adenylate cyclase or phospholipase C (PLC), which in turn are coupled via G-proteins to exogenously expressed receptors (see, for example, McClintock T. S. et al. (1993) Anal. Biochem. 209: 298-305; McClintock T. S. and Lerner M. R. (1997) Brain Res. Brain, Res. Protoc. 2: 59-68, Potenza M N (1992) Pigment Cell Res. 5: 372-328, and Potenza M. N. (1992) Anal. Biochem. 206: 315-322).

As used herein, the terms "modulator of hTAS2R bitter taste receptor activity", includes both agonists and antagonists of hTAS2R bitter taste receptor activity. In the context of the present application, the expression "hTAS2R bitter taste receptor" includes the hTAS2R40 bitter taste receptor, the hTAS2R43 bitter taste receptor, the hTAS2R44 bitter taste receptor, the hTAS2R46 bitter taste receptor, and the hTAS2R47 bitter taste receptor.

As used herein, the term "3β hydroxy dihydro costunolide" refers to the compound according to formula I:

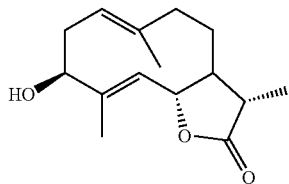

(I)

as well as to pharmaceutically acceptable salts thereof.

As used herein, the term "3β hydroxy pelenolide" refers to the compound according to formula II:

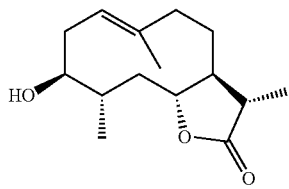

(II)

as well as to pharmaceutically acceptable salts thereof.

As used herein, the term "structurally related" refers to a compound which is derived from its corresponding parent compound by 1, 2, 3, 4, 5 or 6 steps of chemical modification. Thus, an antagonist or agonist structurally related to 3β hydroxy dihydro costunolide is derived from 3β hydroxy dihydro costunolide by 1, 2, 3, 4, 5 or 6 steps of chemical modification. Likewise, an antagonist or agonist structurally related to 3β hydroxy pelenolide is derived from 3β hydroxy pelenolide by 1, 2, 3, 4, 5 or 6 steps of chemical modification. Such chemical modifications include the introduction and/or exchange of one or more substituents.

Such structurally related antagonists are further defined in functional terms in that they inhibit the bitter taste receptor activity of a receptor described herein (hTAS2R40, hTAS2R43, hTAS2R44, hTAS2R46, and/or hTAS2R47). In particular, an antagonist structurally related to 3β hydroxy dihydro costunolide or 3β hydroxy pelenolide lowers the bitter taste receptor activity of a particular receptor compared to the activity determined in the presence of an agonist of said particular receptor by at least 10% (e.g. at least 10%, 15%, 20%, 30%, 40%, 50%, 60%, 70%, 80%, 90%, 95%, 98%, 99%, 99.5% or 100%). Agonists suitable for this purpose are listed below in Table 1. Preferably, the structurally related antagonist exerts this action, when it is contacted prior, concomitantly or after, preferably concomitantly, to the contacting of the bitter taste receptor polypeptide, the host cell expressing the bitter taste receptor polypeptide, or the vector comprising the bitter taste receptor polynucleotide, with a corresponding bitter taste receptor agonist. As indicated above, the terms "bitter taste receptor polypeptide", "bitter taste receptor polynucleotide", and "bitter taste receptor agonist" refer to polypeptides, polynucleotides, and agonists, respectively, of the bitter taste receptors described herein, i.e. hTAS2R40, hTAS2R43, hTAS2R44, hTAS2R46, and/or hTAS2R47.

Structurally related agonists are further defined in functional terms in that they enhance the bitter taste receptor activity of a receptor described herein (hTAS2R40, hTAS2R43, hTAS2R44, hTAS2R46, and/or hTAS2R47). In particular, an agonist structurally related to 3β hydroxy dihydro costunolide (formula (I) in FIG. 1) or 3β hydroxy pelenolide (formula (II) in FIG. 1) stimulates the activity of the receptor in question to at least 50% (e.g. at least 60%, 70%, 80%, 90%, 95%, 100%, 110%, 120%, 130%, 140%, 150%, 200%, 250% 300%, 400%, 500%, 1000%) of the activity elicited by one of the agonists of hTAS2R40, hTAS2R43, hTAS2R44, hTAS2R46, and/or hTAS2R47 listed in Table 1 below at the same molar concentration.

Agonists of hTAS2R40, hTAS2R43, hTAS2R44, hTAS2R46, and/or hTAS2R47 suitable for practicing the present invention are listed in the following table:

TABLE 1

Agonists of bitter taste receptors hTAS2R40, hTAS2R43, hTAS2R44, hTAS2R46, and hTAS2R47

| Bitter Taste Receptor | Agonists |
|---|---|
| hTAS2R40 | cohumulone, humulone, adhumulone, colupulone, isoxanthohumol, xanthohumol, quinine, chlorpheniramine, dapsone, diphenhydramine, diphenidol |
| hTAS2R43 | saccharin, aloin, amarogentin, arborescin, arglabin, aristolochic acid, caffeine, falcarindiol, grossheimin, helicon, quinine, acesulfame K, chloramphenicol, cromolyn, denatonium benzoate, diphenidol |
| hTAS2R44 | aristolochic acids, parthenolide, quinine, acesulfame K, diphenidole, famotidine, saccharin |
| hTAS2R46 | picrotoxinin, strychnine, absinthin, amarogentin, andrographolide, arborescin, arglabin, artemorin, brucine, caffeine, cascarillin, cnicin, colchicine, crispolide, grossheimin, parthenolide, quassin, quinine, tatridin B, yohimbin, azathioprine, carisoprodol, chloramphenicol, chlorpheniramine, denatonium benzoate, diphenidole, hydrocortisone, orphenadrine |
| hTAS2R47 | brucine, absinthin, amarogentin, artemorin, campher, cascarillin, picrotoxinin, quassin, denatonium benzoate, diphenidole |

The term "contacting" in the context of the present invention means any interaction between the antagonist and/or agonist with the polypeptide or the host cell, whereby any of the at least two components can be independently of each other in a liquid phase, for example in solution, or in suspension or can be bound to a solid phase, for example, in the form of an essentially planar surface or in the form of particles, beads or the like. In a preferred embodiment a multitude of different compounds are immobilized on a solid surface like, for example, on a compound library chip and the protein of the present invention is subsequently contacted with such a chip. In another preferred embodiment the host cells are genetically engineered with a polynucleotide encoding a bitter taste receptor described herein (hTAS2R40, hTAS2R43, hTAS2R44, hTAS2R46, or hTAS2R47), or with a vector containing such a polynucleotide, express said bitter taste receptor at the cell surface and are contacted separately in small containers, e.g., micro-titre plates, with various compounds.

As used herein, the term "isolating an antagonist" refers to the process of selecting, identifying, isolating or evolving an antagonist out of a group of at least two different potential antagonists whereby the said selected, identified, isolated or evolved antagonist exhibits preferred features compared with the other antagonists such as, for example, stronger and/or longer or shorter inhibition of receptor activation. Similarly, the term "isolating an agonist" refers to the process of selecting, identifying, isolating or evolving an agonist out of a group of at least two different potential agonists whereby the said selected, identified, isolated or evolved agonist exhibits preferred features compared with the other agonists such as, for example, stronger and/or longer or shorter receptor activation.

As used herein, "operatively linked" means incorporated into a genetic construct so that expression control sequences effectively control expression of a coding sequence of interest.

As used herein, "genetically engineered" means that the host cell is transgenic for the polynucleotide or vector containing the polynucleotide.

As used herein, the term "vector" refers to a protein or a polynucleotide or a mixture thereof which is capable of being introduced or of introducing the proteins and/or nucleic acid comprised therein into a cell. In the context of the present invention it is preferred that the proteins encoded by the introduced polynucleotide are expressed within the cell upon introduction of the vector.

A polynucleotide encoding a "mature form" of a protein or polypeptide means that said protein or polypeptide contains all polypeptide elements that allow it to undergo some or all potential post- or cotranslational processes such as proteolytic processing, phosphorylation, lipidation and the like comprised in the state of the art such that said polypeptide or protein can correctly fold and carry out part or all of its wild-type function once it reaches its "mature form".

"Pharmaceutically acceptable" means approved by a regulatory agency of the Federal or a state government or listed in the U.S. Pharmacopeia or other generally recognized pharmacopeia for use in animals, and more particularly in humans.

Embodiments of the Invention

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The present inventors have identified two antagonists, namely 3β hydroxy dihydro costunolide (formula (I) in FIG. 1) and 3β hydroxy pelenolide (formula (II) in FIG. 1), which specifically inhibit the function of human bitter taste receptors hTAS2R40, hTAS2R43, hTAS2R44, hTAS2R46, and hTAS2R47—an important finding for the food and pharmaceutical industries. DNA sequences of these five receptors are shown in the sequence listing as SEQ ID NO: 13, 5, 7, 9, and 11, respectively, and amino acid sequences of these five receptors are shown as SEQ ID NO: 14, 6, 8, 10, and 12, respectively. To be more specific, 3β hydroxy dihydro costunolide inhibits the function of hTAS2R40, hTAS2R43, hTAS2R46, and hTAS2R47. 3β hydroxy pelenolide inhibits the function of hTAS2R40, hTAS2R43, hTAS2R44, hTAS2R46, and hTAS2R47.

The DNA sequences of hTAS2R1 and hTAS2R4 are included in the sequence listing for comparative purposes as SEQ ID NO: 1 and 3, respectively. The amino acid sequences of hTAS2R1 and hTAS2R4 are included in the sequence listing for comparative purposes as SEQ ID NO: 2 and 4, respectively.

The antagonists provided by the present inventors provide the skilled person with a tool to design compound libraries to screen for structurally related antagonists to suppress the bitter response of the human bitter taste receptor described herein (hTAS2R40, hTAS2R43, hTAS2R44, hTAS2R46, and hTAS2R47), which in turn enables the development of compounds and compositions to suppress or eliminate bitter tasting components of foods, in particular animal foods, nutrients and dietary supplements and pharmaceutical or homeopathic preparations containing such phytochemicals.

The antagonists provided by the present inventors additionally provide the skilled person with a tool to design compound libraries to screen for structurally related agonists to enhance the bitter response of the human bitter taste receptor described herein (hTAS2R40, hTAS2R43, hTAS2R44, hTAS2R46, and hTAS2R47), which in turn enables the development of compounds and compositions to enhance bitter tasting components of foods, in particular animal foods, nutrients and dietary supplements and pharmaceutical or homeopathic preparations containing such phytochemicals.

Thus, in a first aspect the present invention is directed to a method for identifying an antagonist of hTAS2R40 bitter taste receptor activity, hTAS2R43 bitter taste receptor activity, hTAS2R44 bitter taste receptor activity, hTAS2R46 bitter taste receptor activity, or hTAS2R47 bitter taste receptor activity, wherein the bitter taste receptor is encoded by a polynucleotide selected from the group consisting of:

(a) polynucleotide encoding at least the mature form of the polypeptide having the amino acid sequence as shown in SEQ ID NO: 14, SEQ ID NO: 6, SEQ ID NO: 8, SEQ ID NO: 10, or SEQ ID NO: 12;

(b) polynucleotide having the coding nucleotide sequence as shown in SEQ ID NO: 13, SEQ ID NO: 5, SEQ ID NO: 7, SEQ ID NO: 9, or SEQ ID NO: 11 encoding at least the mature form of the polypeptide;

(c) polynucleotide encoding a fragment or variant of a polypeptide encoded by a polynucleotide of any one of (a) to (b), wherein in said variant one or more amino acid residues are conservatively substituted compared to said polypeptide, and said fragment or derivative has hTAS2R40 bitter taste receptor activity, hTAS2R43 bitter taste receptor activity, hTAS2R44 bitter taste receptor activity, hTAS2R46 bitter taste receptor activity, or hTAS2R47 bitter taste receptor activity;

(d) polynucleotide which is an ortholog of the polynucleotide sequences shown in SEQ ID NO: 13, SEQ ID NO: 5, SEQ ID NO: 7, SEQ ID NO: 9, or SEQ ID NO: 11 encoding at least the mature form of the corresponding bitter taste receptor;

(e) polynucleotide which encodes a polypeptide having hTAS2R40 bitter taste receptor activity, hTAS2R43 bitter taste receptor activity, hTAS2R44 bitter taste receptor activity, hTAS2R46 bitter taste receptor activity, or hTAS2R47 bitter taste receptor activity, and where said polypeptide is at least 80% identical to a polypeptide as shown in SEQ ID NO: 14, SEQ ID NO: 6, SEQ ID NO: 8, SEQ ID NO: 10, or SEQ ID NO: 12; and (f) polynucleotide the complementary strand of which hybridizes under stringent conditions to a polynucleotide as defined in any one of (a) to (e) and which codes for a polypeptide having hTAS2R40 bitter taste receptor activity, hTAS2R43 bitter taste receptor activity, hTAS2R44 bitter taste receptor activity, hTAS2R46 bitter taste receptor activity, or hTAS2R47 bitter taste receptor activity;

comprising the steps:

(1) contacting a bitter taste receptor encoded by said polynucleotide or a host cell genetically engineered with said polynucleotide or with a vector containing said polynucleotide to express said bitter taste receptor with a potential antagonist or with a pharmaceutically acceptable salt thereof, said potential antagonist having a structure according to formula (IV):

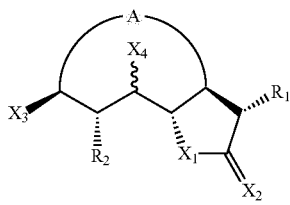

(IV)

wherein $X_1$ is —O—, —S—, or —NH—, preferably —O— or —S—, most preferably —O—;

$X_2$ is =O, =S, or =NH, preferably =O or =S, most preferably =O;

$X_3$ is —OH, —SH, —NH$_2$, —NO$_2$, —CN, —COOH, =O, =S, =NH, —O—CH$_3$, —S—CH$_3$, or —NH—CH$_3$, preferably —OH, —SH, —NH$_2$, —NO$_2$, —CN, —COOH, =O, =S, or =NH, more preferably —OH, —SH, =O, or =S, even more preferably —OH or —SH, most preferably —OH;

$X_4$ is selected from the group consisting of hydrogen, $C_1$ to $C_4$ alkyl, e.g. $C_1$, $C_2$, $C_3$, or $C_4$ alkyl, preferably, methyl, ethyl, propyl (i.e. n-propyl or iso-propyl), butyl (i.e. n-butyl, sec-butyl, iso-butyl, or tert-butyl); $C_1$ to $C_4$ alkenyl, e.g. $C_1$, $C_2$, $C_3$, or $C_4$ alkenyl, preferably methenyl, ethenyl, 1-propenyl, 2-propenyl, 1-iso-propenyl, 2-iso-propenyl, 1-butenyl, 2-butenyl, 3-butenyl; $C_2$ to $C_4$ alkynyl, e.g. $C_2$, $C_3$, or $C_4$, alkynyl; $C_1$ to $C_3$ alkoxy, e.g. $C_1$, $C_2$, or $C_3$ alkoxy, preferably methoxy, ethoxy, propoxy, (i.e. n-propoxy, iso-propoxy); $C_1$ to $C_3$ heteroalkyl, e.g. $C_1$, $C_2$, or $C_3$ heteroalkyl; $C_1$ to $C_3$ heteroalkenyl, e.g. $C_1$, $C_2$, or $C_3$ heteroalkenyl; and $C_2$ to $C_3$ heteroalkynyl; or $X_4$ forms a single bond to A; preferably $X_4$ is hydrogen or —CH$_3$ or forms a single bond to A; more preferably $X_4$ is hydrogen;

A is selected from the group consisting of straight or branched $C_4$ to $C_7$ alkyl (i.e. $C_4$, $C_5$, $C_6$, or $C_7$ alkyl), straight or branched $C_4$ to $C_7$ alkenyl (i.e. $C_4$, $C_5$, $C_6$, or $C_7$ alkenyl), straight or branched $C_4$ to $C_7$ alkynyl (i.e. $C_4$, $C_5$, $C_6$, or $C_7$ alkynyl), straight or branched $C_3$ to $C_6$ heteroalkyl (i.e. $C_3$, $C_4$, $C_5$, or $C_6$ heteroalkyl), straight or branched $C_3$ to $C_6$ heteroalkenyl (i.e. $C_3$, $C_4$, $C_5$, or $C_6$ heteroalkenyl), and straight or branched $C_3$ to $C_6$ heteroalkynyl (i.e. $C_3$, $C_4$, $C_5$, or $C_6$ heteroalkynyl), wherein said alkyl, alkenyl, alkynyl, heteroalkyl, heteroalkenyl, and heteroalkynyl are optionally substituted 1, 2, 3, 4, or 5 times, preferably 1, 2, or 3 times, and more preferably once or twice;

$R_1$ is selected from the group consisting of hydrogen, $C_1$ to $C_4$ alkyl, e.g. $C_1$, $C_2$, $C_3$, or $C_4$ alkyl, preferably, methyl, ethyl, propyl (i.e. n-propyl or iso-propyl), butyl (i.e. n-butyl, sec-butyl, iso-butyl, or tert-butyl); $C_1$ to $C_4$ alkenyl, e.g. $C_1$, $C_2$, $C_3$, or $C_4$ alkenyl, preferably methenyl, ethenyl, 1-propenyl, 2-propenyl, 1-iso-propenyl, 2-iso-propenyl, 1-butenyl, 2-butenyl, 3-butenyl; $C_2$ to $C_4$ alkynyl, e.g. $C_2$, $C_3$, or $C_4$, alkynyl; $C_1$ to $C_3$ alkoxy, e.g. $C_1$, $C_2$, or $C_3$ alkoxy, preferably methoxy, ethoxy, propoxy, (i.e. n-propoxy, iso-propoxy); $C_1$ to $C_3$ heteroalkyl, e.g. $C_1$, $C_2$, or $C_3$ heteroalkyl; $C_1$ to $C_3$ heteroalkenyl, e.g. $C_1$, $C_2$, or $C_3$ heteroalkenyl; and $C_2$ to $C_3$ heteroalkynyl; wherein said alkyl, alkenyl, alkynyl, alkoxy, heteroalkyl, heteroalkenyl, and heteroalkynyl are optionally substituted once or twice; preferably $R_1$ is —CH$_3$ or =CH$_2$ or hydrogen, more preferably —CH$_3$ or =CH$_2$;

$R_2$ is selected from the group consisting of hydrogen, $C_1$ to $C_4$ alkyl, e.g. $C_1$, $C_2$, $C_3$, or $C_4$ alkyl, preferably, methyl, ethyl, propyl (i.e. n-propyl or iso-propyl), butyl (i.e. n-butyl, sec-butyl, iso-butyl, or tert-butyl); $C_1$ to $C_4$ alkenyl, e.g. $C_1$, $C_2$, $C_3$, or $C_4$ alkenyl, preferably methenyl, ethenyl, 1-propenyl, 2-propenyl, 1-iso-propenyl, 2-iso-propenyl, 1-butenyl, 2-butenyl, 3-butenyl; $C_2$ to $C_4$ alkynyl, e.g. $C_2$, $C_3$, or $C_4$, alkynyl; $C_1$ to $C_3$ alkoxy, e.g. $C_1$, $C_2$, or $C_3$ alkoxy, preferably methoxy, ethoxy, propoxy, (i.e. n-propoxy, iso-propoxy); $C_1$ to $C_3$ heteroalkyl, e.g. $C_1$, $C_2$, or $C_3$ heteroalkyl; $C_1$ to $C_3$ heteroalkenyl, e.g. $C_1$, $C_2$, or $C_3$ heteroalkenyl; and $C_2$ to $C_3$ heteroalkynyl; wherein said alkyl, alkenyl, alkynyl, alkoxy, heteroalkyl, heteroalkenyl, and heteroalkynyl are optionally substituted once or twice; preferably $R_2$ is —CH$_3$ or hydrogen, more preferably —CH$_3$;

and (2) determining whether the potential antagonist inhibits the bitter taste receptor activity;

wherein prior to, concomitantly with and/or after step (1) said bitter taste receptor or said host cell is contacted with an agonist of bitter taste receptor hTAS2R40, bitter taste receptor hTAS2R43, bitter taste receptor hTAS2R44, bitter taste receptor hTAS2R46, or bitter taste receptor hTAS2R47.

In a preferred embodiment of the first aspect, A is selected from the group consisting of straight $C_4$ to $C_7$ alkyl (i.e. $C_4$, $C_5$, $C_6$, or $C_7$ alkyl), straight $C_4$ to $C_7$ alkenyl (i.e. $C_4$, $C_5$, $C_6$, or $C_7$ alkenyl), straight $C_4$ to $C_7$ alkynyl (i.e. $C_4$, $C_5$, $C_6$, or $C_7$ alkynyl), straight $C_3$ to $C_6$ heteroalkyl (i.e. $C_3$, $C_4$, $C_5$, or $C_6$ heteroalkyl), straight $C_3$ to $C_6$ heteroalkenyl (i.e. $C_3$, $C_4$, $C_5$, or $C_6$ heteroalkenyl), and straight $C_3$ to $C_6$ heteroalkynyl (i.e. $C_3$, $C_4$, $C_5$, or $C_6$ heteroalkynyl); preferably straight $C_4$ to $C_7$ alkyl (i.e. $C_4$, $C_5$, $C_6$, or $C_7$ alkyl) and straight $C_4$ to $C_7$ alkenyl (i.e. $C_4$, $C_5$, $C_6$, or $C_7$ alkenyl); wherein said alkyl, alkenyl, alkynyl, heteroalkyl, heteroalkenyl, and heteroalkynyl are optionally substituted 1, 2, 3, 4, or 5 times, preferably 1, 2, or 3 times, and more preferably once or twice.

In a more preferred embodiment of the first aspect, A is selected from the group consisting of straight $C_5$ to $C_6$ alkyl, straight $C_5$ to $C_6$ alkenyl, straight $C_5$ to $C_6$ alkynyl, straight $C_4$ to $C_5$ heteroalkyl, straight $C_4$ to $C_5$ heteroalkenyl, and straight $C_4$ to $C_5$ heteroalkynyl; preferably straight $C_5$ to $C_6$ alkyl and straight $C_5$ to $C_6$ alkenyl; wherein said alkyl, alkenyl, alkynyl, heteroalkyl, heteroalkenyl, and heteroalkynyl are optionally substituted 1, 2, 3, 4, or 5 times, preferably 1, 2, or 3 times, and more preferably once or twice.

In an even more preferred embodiment of the first aspect, A is selected from the group consisting of straight $C_5$ alkyl, straight $C_5$ alkenyl, straight $C_5$ alkynyl, straight $C_4$ heteroalkyl, straight $C_4$ heteroalkenyl, and straight $C_4$ heteroalkynyl; preferably straight $C_5$ alkyl and straight $C_5$ alkenyl; wherein said alkyl, alkenyl, alkynyl, heteroalkyl, heteroalkenyl, and heteroalkynyl are optionally substituted 1, 2, 3, 4, or 5 times, preferably 1, 2, or 3 times, and more preferably once or twice.

In a preferred embodiment of the first aspect, the optional substituents of A are in each instance independently selected from the group consisting of halogen (i.e. F, Cl, Br, or I), —OH, —SH, —NH$_2$, —NO$_2$, —CN, —COOH, =O, =S, =NH; $C_1$ to $C_4$ alkyl, e.g. $C_1$, $C_2$, $C_3$, or $C_4$ alkyl, preferably, methyl, ethyl, propyl (i.e. n-propyl or iso-propyl), butyl (i.e. n-butyl, sec-butyl, iso-butyl, or tert-butyl); $C_1$ to $C_4$ alkenyl, e.g. $C_1$, $C_2$, $C_3$, or $C_4$ alkenyl, preferably methenyl, ethenyl, 1-propenyl, 2-propenyl, 1-iso-propenyl, 2-iso-propenyl, 1-butenyl, 2-butenyl, 3-butenyl; $C_2$ to $C_4$ alkynyl, e.g. $C_2$, $C_3$, or $C_4$, alkynyl; $C_1$ to $C_3$ alkoxy e.g. $C_1$, $C_2$, or $C_3$ alkoxy, preferably methoxy, ethoxy, propoxy, (i.e. n-propoxy, iso-propoxy); $C_1$ to $C_3$ heteroalkyl, e.g. $C_1$, $C_2$, or $C_3$ heteroalkyl; $C_1$ to $C_3$ heteroalkenyl, e.g. $C_1$, $C_2$, or $C_3$ heteroalkenyl; and $C_2$ to $C_3$ heteroalkynyl. In a more preferred embodiment of the first aspect, the optional substituents of A are in each instance independently selected from the group consisting of —OH, —O—C(O)—CH$_3$, —CH$_3$, and =CH$_2$.

In a preferred embodiment of the first aspect, said potential antagonist has a structure according to formula (VI):

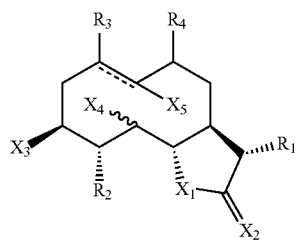

(VI)

wherein

X$_1$, X$_2$, X$_3$, R$_1$ and R$_2$ are defined as above;

X$_4$ is selected from the group consisting of hydrogen, C$_1$ to C$_4$ alkyl, e.g. C$_1$, C$_2$, C$_3$, or C$_4$ alkyl, preferably, methyl, ethyl, propyl (i.e. n-propyl or iso-propyl), butyl (i.e. n-butyl, sec-butyl, iso-butyl, or tert-butyl); C$_1$ to C$_4$ alkenyl, e.g. C$_1$, C$_2$, C$_3$, or C$_4$ alkenyl, preferably methenyl, ethenyl, 1-propenyl, 2-propenyl, 1-iso-propenyl, 2-iso-propenyl, 1-butenyl, 2-butenyl, 3-butenyl; C$_2$ to C$_4$ alkynyl, e.g. C$_2$, C$_3$, or C$_4$, alkynyl; C$_1$ to C$_3$ alkoxy, e.g. C$_1$, C$_2$, or C$_3$ alkoxy, preferably methoxy, ethoxy, propoxy, (i.e. n-propoxy, iso-propoxy); C$_1$ to C$_3$ heteroalkyl, e.g. C$_1$, C$_2$, or C$_3$ heteroalkyl; C$_1$ to C$_3$ heteroalkenyl, e.g. C$_1$, C$_2$, or C$_3$ heteroalkenyl; and C$_2$ to C$_3$ heteroalkynyl; or X$_4$ forms a single bond to the carbon atom carrying X$_5$; preferably X$_4$ is hydrogen or —CH$_3$ or forms a single bond to the carbon atom carrying X$_5$; more preferably X$_4$ is hydrogen;

X$_5$ is selected from the group consisting of hydrogen, C$_1$ to C$_4$ alkyl, e.g. C$_1$, C$_2$, C$_3$, or C$_4$ alkyl, preferably, methyl, ethyl, propyl (i.e. n-propyl or iso-propyl), butyl (i.e. n-butyl, sec-butyl, iso-butyl, or tert-butyl); C$_1$ to C$_4$ alkenyl, e.g. C$_1$, C$_2$, C$_3$, or C$_4$ alkenyl, preferably methenyl, ethenyl, 1-propenyl, 2-propenyl, 1-iso-propenyl, 2-iso-propenyl, 1-butenyl, 2-butenyl, 3-butenyl; C$_2$ to C$_4$ alkynyl, e.g. C$_2$, C$_3$, or C$_4$, alkynyl; C$_1$ to C$_3$ alkoxy, e.g. C$_1$, C$_2$, or C$_3$ alkoxy, preferably methoxy, ethoxy, propoxy, (i.e. n-propoxy, iso-propoxy); C$_1$ to C$_3$ heteroalkyl, e.g. C$_1$, C$_2$, or C$_3$ heteroalkyl; C$_1$ to C$_3$ heteroalkenyl, e.g. C$_1$, C$_2$, or C$_3$ heteroalkenyl; and C$_2$ to C$_3$ heteroalkynyl; preferably X$_5$ is hydrogen, —CH$_3$, or =CH$_2$; more preferably X$_5$ is —CH$_3$ or =CH$_2$;

R$_3$ is selected from the group consisting of hydrogen, halogen (i.e. F, Cl, Br, or I), —OH, —SH, —NH$_2$, —NO$_2$, —CN, —COOH, =O, =S, =NH, C$_1$ to C$_4$ alkyl, e.g. C$_1$, C$_2$, C$_3$, or C$_4$ alkyl, preferably, methyl, ethyl, propyl (i.e. n-propyl or iso-propyl), butyl (i.e. n-butyl, sec-butyl, iso-butyl, or tert-butyl); C$_1$ to C$_4$ alkenyl, e.g. C$_1$, C$_2$, C$_3$, or C$_4$ alkenyl, preferably methenyl, ethenyl, 1-propenyl, 2-propenyl, 1-iso-propenyl, 2-iso-propenyl, 1-butenyl, 2-butenyl, 3-butenyl; C$_2$ to C$_4$ alkynyl, e.g. C$_2$, C$_3$, or C$_4$, alkynyl; C$_1$ to C$_3$ alkoxy, e.g. C$_1$, C$_2$, or C$_3$ alkoxy, preferably methoxy, ethoxy, propoxy, (i.e. n-propoxy, iso-propoxy); C$_1$ to C$_3$ heteroalkyl, e.g. C$_1$, C$_2$, or C$_3$ heteroalkyl; C$_1$ to C$_3$ heteroalkenyl, e.g. C$_1$, C$_2$, or C$_3$ heteroalkenyl; and C$_2$ to C$_3$ heteroalkynyl; preferably —OH, —O—C(O)—CH$_3$, —CH$_3$, and =CH$_2$;

R$_4$ is selected from the group consisting of hydrogen, halogen (i.e. F, Cl, Br, or I), —OH, —SH, —NH$_2$, —NO$_2$, —CN, —COOH, =O, =S, =NH, C$_1$ to C$_4$ alkyl, e.g. C$_1$, C$_2$, C$_3$, or C$_4$ alkyl, preferably, methyl, ethyl, propyl (i.e. n-propyl or iso-propyl), butyl (i.e. n-butyl, sec-butyl, iso-butyl, or tert-butyl); C$_1$ to C$_4$ alkenyl, e.g. C$_1$, C$_2$, C$_3$, or C$_4$ alkenyl, preferably methenyl, ethenyl, 1-propenyl, 2-propenyl, 1-iso-propenyl, 2-iso-propenyl, 1-butenyl, 2-butenyl, 3-butenyl; C$_2$ to C$_4$ alkynyl, e.g. C$_2$, C$_3$, or C$_4$, alkynyl; C$_1$ to C$_3$ alkoxy, e.g. C$_1$, C$_2$, or C$_3$ alkoxy, preferably methoxy, ethoxy, propoxy, (i.e. n-propoxy, iso-propoxy); C$_1$ to C$_3$ heteroalkyl, e.g. C$_1$, C$_2$, or C$_3$ heteroalkyl; C$_1$ to C$_3$ heteroalkenyl, e.g. C$_1$, C$_2$, or C$_3$ heteroalkenyl; and C$_2$ to C$_3$ heteroalkynyl; preferably —OH, —O—C(O)—CH$_3$, —CH$_3$, and =CH$_2$; and the dotted line between the carbon atom carrying R$_3$ and the carbon atom carrying X$_5$ designates an optional bond, i.e. said two carbon atoms may be linked via a single bond or a double bond.

In a second aspect the present invention is directed to a method for identifying an antagonist of hTAS2R40 bitter taste receptor activity, hTAS2R43 bitter taste receptor activity, hTAS2R46 bitter taste receptor activity, or hTAS2R47 bitter taste receptor activity, wherein the bitter taste receptor is encoded by a polynucleotide selected from the group consisting of:

(a) polynucleotide encoding at least the mature form of the polypeptide having the amino acid sequence as shown in SEQ ID NO: 14, SEQ ID NO: 6, SEQ ID NO: 10, or SEQ ID NO: 12;

(b) polynucleotide having the coding nucleotide sequence as shown in SEQ ID NO: 13, SEQ ID NO: 5, SEQ ID NO: 9, or SEQ ID NO: 11 encoding at least the mature form of the polypeptide;

(c) polynucleotide encoding a fragment or variant of a polypeptide encoded by a polynucleotide of any one of (a) to (b), wherein in said variant one or more amino acid residues are conservatively substituted compared to said polypeptide, and said fragment or derivative has hTAS2R40 bitter taste receptor activity, hTAS2R43 bitter taste receptor activity, hTAS2R46 bitter taste receptor activity, or hTAS2R47 bitter taste receptor activity;

(d) polynucleotide which is an ortholog of the polynucleotide sequences shown in SEQ ID NO: 13, SEQ ID NO: 5, SEQ ID NO: 9, or SEQ ID NO: 11 encoding at least the mature form of the corresponding bitter taste receptor;

(e) polynucleotide which encodes a polypeptide having hTAS2R40 bitter taste receptor activity, hTAS2R43 bitter taste receptor activity, hTAS2R46 bitter taste receptor activity, or hTAS2R47 bitter taste receptor activity, and where said polypeptide is at least 80% identical to a polypeptide as shown in SEQ ID NO: 14, SEQ ID NO: 6, SEQ ID NO: 10, or SEQ ID NO: 12; and (f) polynucleotide the complementary strand of which hybridizes under stringent conditions to a polynucleotide as defined in any one of (a) to (e) and which codes for a polypeptide having hTAS2R40 bitter taste receptor activity, hTAS2R43 bitter taste receptor activity, hTAS2R46 bitter taste receptor activity, or hTAS2R47 bitter taste receptor activity;

comprising the steps:

(1) contacting a bitter taste receptor encoded by said polynucleotide or a host cell genetically engineered with said polynucleotide or with a vector containing said polynucleotide to express said bitter taste receptor with a potential antagonist or with a pharmaceutically acceptable salt thereof, said potential antagonist having a structure according to formula (III):

(III)

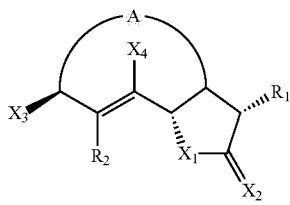

wherein $X_1$ is —O—, —S—, or —NH—, preferably —O— or —S—, most preferably —O—;

$X_2$ is =O, =S, or =NH, preferably =O or =S, most preferably =O;

$X_3$ is —OH, —SH, —NH$_2$, —NO$_2$, —CN, —COOH, =O, =S, =NH, —O—CH$_3$, —S—CH$_3$, or —NH—CH$_3$, preferably —OH, —SH, —NH$_2$, —NO$_2$, —CN, —COOH, =O, =S, or =NH, more preferably —OH, —SH, =O, or =S, even more preferably —OH or —SH, most preferably —OH;

$X_4$ is selected from the group consisting of hydrogen, $C_1$ to $C_4$ alkyl, e.g. $C_1$, $C_2$, $C_3$, or $C_4$ alkyl, preferably, methyl, ethyl, propyl (i.e. n-propyl or iso-propyl), butyl (i.e. n-butyl, sec-butyl, iso-butyl, or tert-butyl); $C_2$ to $C_4$ alkenyl, e.g. $C_2$, $C_3$, or $C_4$ alkenyl, preferably ethenyl, 1-propenyl, 2-propenyl, 1-iso-propenyl, 2-iso-propenyl, 1-butenyl, 2-butenyl, 3-butenyl; $C_2$ to $C_4$ alkynyl, e.g. $C_2$, $C_3$, or $C_4$, alkynyl; $C_1$ to $C_3$ alkoxy, e.g. $C_1$, $C_2$, or $C_3$ alkoxy, preferably methoxy, ethoxy, propoxy, (i.e. n-propoxy, iso-propoxy); $C_1$ to $C_3$ heteroalkyl, e.g. $C_1$, $C_2$, or $C_3$ heteroalkyl; $C_2$ to $C_3$ heteroalkenyl; and $C_2$ to $C_3$ heteroalkynyl; or $X_4$ forms a single bond to A; preferably $X_4$ is hydrogen or —CH$_3$ or forms a single bond to A; more preferably $X_4$ is hydrogen;

A is selected from the group consisting of straight or branched $C_4$ to $C_7$ alkyl (i.e. $C_4$, $C_5$, $C_6$, or $C_7$ alkyl), straight or branched $C_4$ to $C_7$ alkenyl (i.e. $C_4$, $C_5$, $C_6$, or $C_7$ alkenyl), straight or branched $C_4$ to $C_7$ alkynyl (i.e. $C_4$, $C_5$, $C_6$, or $C_7$ alkynyl), straight or branched $C_3$ to $C_6$ heteroalkyl (i.e. $C_3$, $C_4$, $C_5$, or $C_6$ heteroalkyl), straight or branched $C_3$ to $C_6$ heteroalkenyl (i.e. $C_3$, $C_4$, $C_5$, or $C_6$ heteroalkenyl), and straight or branched $C_3$ to $C_6$ heteroalkynyl (i.e. $C_3$, $C_4$, $C_5$, or $C_6$ heteroalkynyl), wherein said alkyl, alkenyl, alkynyl, heteroalkyl, heteroalkenyl, and heteroalkynyl are optionally substituted 1, 2, 3, 4, or 5 times, preferably 1, 2, or 3 times, and more preferably once or twice;

$R_1$ is selected from the group consisting of hydrogen, $C_1$ to $C_4$ alkyl, e.g. $C_1$, $C_2$, $C_3$, or $C_4$ alkyl, preferably, methyl, ethyl, propyl (i.e. n-propyl or iso-propyl), butyl (i.e. n-butyl, sec-butyl, iso-butyl, or tert-butyl); $C_1$ to $C_4$ alkenyl, e.g. $C_1$, $C_2$, $C_3$, or $C_4$ alkenyl, preferably methenyl, ethenyl, 1-propenyl, 2-propenyl, 1-iso-propenyl, 2-iso-propenyl, 1-butenyl, 2-butenyl, 3-butenyl; $C_2$ to $C_4$ alkynyl, e.g. $C_2$, $C_3$, or $C_4$, alkynyl; $C_1$ to $C_3$ alkoxy, e.g. $C_1$, $C_2$, or $C_3$ alkoxy, preferably methoxy, ethoxy, propoxy, (i.e. n-propoxy, iso-propoxy); $C_1$ to $C_3$ heteroalkyl, e.g. $C_1$, $C_2$, or $C_3$ heteroalkyl; $C_1$ to $C_3$ heteroalkenyl, e.g. $C_1$, $C_2$, or $C_3$ heteroalkenyl; and $C_2$ to $C_3$ heteroalkynyl; wherein said alkyl, alkenyl, alkynyl, alkoxy, heteroalkyl, heteroalkenyl, and heteroalkynyl are optionally substituted once or twice; preferably $R_1$ is —CH$_3$ or =CH$_2$ or hydrogen, more preferably —CH$_3$ or =CH$_2$;

$R_2$ is selected from the group consisting of hydrogen, $C_1$ to $C_4$ alkyl, e.g. $C_1$, $C_2$, $C_3$, or $C_4$ alkyl, preferably, methyl, ethyl, propyl (i.e. n-propyl or iso-propyl), butyl (i.e. n-butyl, sec-butyl, iso-butyl, or tert-butyl); $C_2$ to $C_4$ alkenyl, e.g. $C_2$, $C_3$, or $C_4$ alkenyl, preferably ethenyl, 1-propenyl, 2-propenyl, 1-iso-propenyl, 2-iso-propenyl, 1-butenyl, 2-butenyl, 3-butenyl; $C_2$ to $C_4$ alkynyl, e.g. $C_2$, $C_3$, or $C_4$, alkynyl; $C_1$ to $C_3$ alkoxy, e.g. $C_1$, $C_2$, or $C_3$ alkoxy, preferably methoxy, ethoxy, propoxy, (i.e. n-propoxy, iso-propoxy); $C_1$ to $C_3$ heteroalkyl, e.g. $C_1$, $C_2$, or $C_3$ heteroalkyl; $C_2$ to $C_3$ heteroalkenyl; and $C_2$ to $C_3$ heteroalkynyl; wherein said alkyl, alkenyl, alkynyl, alkoxy, heteroalkyl, heteroalkenyl, and heteroalkynyl are optionally substituted once or twice; preferably $R_2$ is —CH$_3$ or hydrogen, more preferably —CH$_3$;

and (2) determining whether the potential antagonist inhibits the bitter taste receptor activity;

wherein prior to, concomitantly with and/or after step (1) said bitter taste receptor or said host cell is contacted with an agonist of bitter taste receptor hTAS2R40, bitter taste receptor hTAS2R43, bitter taste receptor hTAS2R46, or bitter taste receptor hTAS2R47.

In a preferred embodiment of the second aspect, A is selected from the group consisting of straight $C_4$ to $C_7$ alkyl (i.e. $C_4$, $C_5$, $C_6$, or $C_7$ alkyl), straight $C_4$ to $C_7$ alkenyl (i.e. $C_4$, $C_5$, $C_6$, or $C_7$ alkenyl), straight $C_4$ to $C_7$ alkynyl (i.e. $C_4$, $C_5$, $C_6$, or $C_7$ alkynyl), straight $C_3$ to $C_6$ heteroalkyl (i.e. $C_3$, $C_4$, $C_5$, or $C_6$ heteroalkyl), straight $C_3$ to $C_6$ heteroalkenyl (i.e. $C_3$, $C_4$, $C_5$, or $C_6$ heteroalkenyl), and straight $C_3$ to $C_6$ heteroalkynyl (i.e. $C_3$, $C_4$, $C_5$, or $C_6$ heteroalkynyl); preferably straight $C_4$ to $C_7$ alkyl (i.e. $C_4$, $C_5$, $C_6$, or $C_7$ alkyl) and straight $C_4$ to $C_7$ alkenyl (i.e. $C_4$, $C_5$, $C_6$, or $C_7$ alkenyl); wherein said alkyl, alkenyl, alkynyl, heteroalkyl, heteroalkenyl, and heteroalkynyl are optionally substituted 1, 2, 3, 4, or 5 times, preferably 1, 2, or 3 times, and more preferably once or twice.

In a more preferred embodiment of the second aspect, A is selected from the group consisting of straight $C_5$ to $C_6$ alkyl, straight $C_5$ to $C_6$ alkenyl, straight $C_5$ to $C_6$ alkynyl, straight $C_4$ to $C_5$ heteroalkyl, straight $C_4$ to $C_5$ heteroalkenyl, and straight $C_4$ to $C_5$ heteroalkynyl; preferably straight $C_5$ to $C_6$ alkyl and straight $C_5$ to $C_6$ alkenyl; wherein said alkyl, alkenyl, alkynyl, heteroalkyl, heteroalkenyl, and heteroalkynyl are optionally substituted 1, 2, 3, 4, or 5 times, preferably 1, 2, or 3 times, and more preferably once or twice.

In an even more preferred embodiment of the second aspect, A is selected from the group consisting of straight $C_5$ alkyl, straight $C_5$ alkenyl, straight $C_5$ alkynyl, straight $C_4$ heteroalkyl, straight $C_4$ heteroalkenyl, and straight $C_4$ heteroalkynyl; preferably straight $C_5$ alkyl and straight $C_5$ alkenyl; wherein said alkyl, alkenyl, alkynyl, heteroalkyl, heteroalkenyl, and heteroalkynyl are optionally substituted 1, 2, 3, 4, or 5 times, preferably 1, 2, or 3 times, and more preferably once or twice.

In a preferred embodiment of the second aspect, the optional substituents of A are in each instance independently selected from the group consisting of halogen (i.e. F, Cl, Br, or I), —OH, —SH, —NH$_2$, —NO$_2$, —CN, —COOH, =O, =S, =NH; $C_1$ to $C_4$ alkyl, e.g. $C_1$, $C_2$, $C_3$, or $C_4$ alkyl, preferably, methyl, ethyl, propyl (i.e. n-propyl or iso-propyl), butyl (i.e. n-butyl, sec-butyl, iso-butyl, or tert-butyl); $C_1$ to $C_4$ alkenyl, e.g. $C_1$, $C_2$, $C_3$, or $C_4$ alkenyl, preferably methenyl, ethenyl, 1-propenyl, 2-propenyl, 1-iso-propenyl, 2-iso-propenyl, 1-butenyl, 2-butenyl, 3-butenyl; $C_2$ to $C_4$ alkynyl, e.g. $C_2$, $C_3$, or $C_4$, alkynyl; $C_1$ to $C_3$ alkoxy e.g. $C_1$, $C_2$, or $C_3$ alkoxy, preferably methoxy, ethoxy, propoxy, (i.e. n-propoxy, iso-propoxy); $C_1$ to $C_3$ heteroalkyl, e.g. $C_1$, $C_2$, or $C_3$ heteroalkyl; $C_1$ to $C_3$ heteroalkenyl, e.g. $C_1$, $C_2$, or $C_3$ heteroalkenyl; and $C_2$ to $C_3$ heteroalkynyl. In a more preferred embodiment of the first aspect, the optional substituents of A are in each instance independently selected from the group consisting of —OH, —O—C(O)—CH$_3$, —CH$_3$, and =CH$_2$.

In a preferred embodiment of the second aspect, said potential antagonist has a structure according to formula (V):

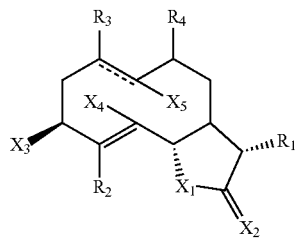

wherein $X_1$, $X_2$, $X_3$, $R_1$ and $R_2$ are defined as above;

$X_4$ is selected from the group consisting of hydrogen, $C_1$ to $C_4$ alkyl, e.g. $C_1$, $C_2$, $C_3$, or $C_4$ alkyl, preferably, methyl, ethyl, propyl (i.e. n-propyl or iso-propyl), butyl (i.e. n-butyl, sec-butyl, iso-butyl, or tert-butyl); $C_2$ to $C_4$ alkenyl, e.g. $C_2$, $C_3$, or $C_4$ alkenyl, preferably ethenyl, 1-propenyl, 2-propenyl, 1-iso-propenyl, 2-iso-propenyl, 1-butenyl, 2-butenyl, 3-butenyl; $C_2$ to $C_4$ alkynyl, e.g. $C_2$, $C_3$, or $C_4$, alkynyl; $C_1$ to $C_3$ alkoxy, e.g. $C_1$, $C_2$, or $C_3$ alkoxy, preferably methoxy, ethoxy, propoxy, (i.e. n-propoxy, iso-propoxy); $C_1$ to $C_3$ heteroalkyl, e.g. $C_1$, $C_2$, or $C_3$ heteroalkyl; $C_2$ to $C_3$ heteroalkenyl; and $C_2$ to $C_3$ heteroalkynyl; or $X_4$ forms a single bond to the carbon atom carrying $X_5$; preferably $X_4$ is hydrogen or —$CH_3$ or forms a single bond to the carbon atom carrying $X_5$; more preferably $X_4$ is hydrogen;

$X_5$ is selected from the group consisting of hydrogen, $C_1$ to $C_4$ alkyl, e.g. $C_1$, $C_2$, $C_3$, or $C_4$ alkyl, preferably, methyl, ethyl, propyl (i.e. n-propyl or iso-propyl), butyl (i.e. n-butyl, sec-butyl, iso-butyl, or tert-butyl); $C_1$ to $C_4$ alkenyl, e.g. $C_1$, $C_2$, $C_3$, or $C_4$ alkenyl, preferably methenyl, ethenyl, 1-propenyl, 2-propenyl, 1-iso-propenyl, 2-iso-propenyl, 1-butenyl, 2-butenyl, 3-butenyl; $C_2$ to $C_4$ alkynyl, e.g. $C_2$, $C_3$, or $C_4$, alkynyl; $C_1$ to $C_3$ alkoxy, e.g. $C_1$, $C_2$, or $C_3$ alkoxy, preferably methoxy, ethoxy, propoxy, (i.e. n-propoxy, iso-propoxy); $C_1$ to $C_3$ heteroalkyl, e.g. $C_1$, $C_2$, or $C_3$ heteroalkyl; $C_1$ to $C_3$ heteroalkenyl, e.g. $C_1$, $C_2$, or $C_3$ heteroalkenyl; and $C_2$ to $C_3$ heteroalkynyl; preferably $X_5$ is hydrogen, —$CH_3$, or =$CH_2$; more preferably $X_5$ is —$CH_3$ or =$CH_2$;

$R_3$ is selected from the group consisting of hydrogen, halogen (i.e. F, Cl, Br, or I), —OH, —SH, —$NH_2$, —$NO_2$, —CN, —COOH, =O, =S, =NH, $C_1$ to $C_4$ alkyl, e.g. $C_1$, $C_2$, $C_3$, or $C_4$ alkyl, preferably, methyl, ethyl, propyl (i.e. n-propyl or iso-propyl), butyl (i.e. n-butyl, sec-butyl, iso-butyl, or tert-butyl); $C_1$ to $C_4$ alkenyl, e.g. $C_1$, $C_2$, $C_3$, or $C_4$ alkenyl, preferably methenyl, ethenyl, 1-propenyl, 2-propenyl, 1-iso-propenyl, 2-iso-propenyl, 1-butenyl, 2-butenyl, 3-butenyl; $C_2$ to $C_4$ alkynyl, e.g. $C_2$, $C_3$, or $C_4$, alkynyl; $C_1$ to $C_3$ alkoxy, e.g. $C_1$, $C_2$, or $C_3$ alkoxy, preferably methoxy, ethoxy, propoxy, (i.e. n-propoxy, iso-propoxy); $C_1$ to $C_3$ heteroalkyl, e.g. $C_1$, $C_2$, or $C_3$ heteroalkyl; $C_1$ to $C_3$ heteroalkenyl, e.g. $C_1$, $C_2$, or $C_3$ heteroalkenyl; and $C_2$ to $C_3$ heteroalkynyl; preferably —OH, —O—C(O)—$CH_3$, —$CH_3$, and =$CH_2$;

$R_4$ is selected from the group consisting of hydrogen, halogen (i.e. F, Cl, Br, or I), —OH, —SH, —$NH_2$, —$NO_2$, —CN, —COOH, =O, =S, =NH, $C_1$ to $C_4$ alkyl, e.g. $C_1$, $C_2$, $C_3$, or $C_4$ alkyl, preferably, methyl, ethyl, propyl (i.e. n-propyl or iso-propyl), butyl (i.e. n-butyl, sec-butyl, iso-butyl, or tert-butyl); $C_1$ to $C_4$ alkenyl, e.g. $C_1$, $C_2$, $C_3$, or $C_4$ alkenyl, preferably methenyl, ethenyl, 1-propenyl, 2-propenyl, 1-iso-propenyl, 2-iso-propenyl, 1-butenyl, 2-butenyl, 3-butenyl; $C_2$ to $C_4$ alkynyl, e.g. $C_2$, $C_3$, or $C_4$, alkynyl; $C_1$ to $C_3$ alkoxy, e.g. $C_1$, $C_2$, or $C_3$ alkoxy, preferably methoxy, ethoxy, propoxy, (i.e. n-propoxy, iso-propoxy); $C_1$ to $C_3$ heteroalkyl, e.g. $C_1$, $C_2$, or $C_3$ heteroalkyl; $C_1$ to $C_3$ heteroalkenyl, e.g. $C_1$, $C_2$, or $C_3$ heteroalkenyl; and $C_2$ to $C_3$ heteroalkynyl; preferably —OH, —O—C(O)—$CH_3$, —$CH_3$, and =$CH_2$; and the dotted line between the carbon atom carrying $R_3$ and the carbon atom carrying $X_5$ designates an optional bond, i.e. said two carbon atoms may be linked via a single bond or a double bond.

In preferred embodiments of the first and the second aspect, $X_3$ is —OH.

In preferred embodiments of the first and the second aspect, $X_1$ is —OH.

In preferred embodiments of the first and the second aspect, $X_2$ is =O.

In preferred embodiments of the first and the second aspect, $X_1$ is —OH and $X_2$ is =O.

In preferred embodiments of the first and the second aspect, $X_3$ is —OH, $X_1$ is —OH and $X_2$ is =O.

In preferred embodiments of the first and the second aspect, the agonist of bitter taste receptor hTAS2R40 is selected from the group consisting of cohumulone, humulone, adhumulone, colupulone, isoxanthohumol, xanthohumol, quinine, chlorpheniramine, dapsone, diphenhydramine, and diphenidol.

In preferred embodiments of the first and the second aspect, the agonist of bitter taste receptor hTAS2R43 is selected from the group consisting of saccharin, aloin, amarogentin, arborescin, arglabin, aristolochic acid, caffeine, falcarindiol, grossheimin, helicon, quinine, acesulfame K, chloramphenicol, cromolyn, denatonium benzoate, and diphenidol.

In preferred embodiments of the first aspect, the agonist of bitter taste receptor hTAS2R44 is selected from the group consisting of aristolochic acids, parthenolide, quinine, acesulfame K, diphenidole, famotidine, and saccharin.

In preferred embodiments of the first and the second aspect, the agonist of bitter taste receptor hTAS2R46 is selected from the group consisting of picrotoxinin, strychnine, absinthin, amarogentin, andrographolide, arborescin, arglabin, artemorin, brucine, caffeine, cascarillin, cnicin, colchicine, crispolide, grossheimin, parthenolide, quassin, quinine, tatridin B, yohimbin, azathioprine, carisoprodol, chloramphenicol, chlorpheniramine, denatonium benzoate, diphenidole, hydrocortisone, and orphenadrine.

In preferred embodiments of the first and the second aspect, the agonist of bitter taste receptor hTAS2R47 is selected from the group consisting of brucine, absinthin, amarogentin, artemorin, campher, cascarillin, picrotoxinin, quassin, denatonium benzoate, and diphenidole.

In preferred embodiments of the first and the second aspect, the identified potential antagonist reduces the activity of hTAS2R40, hTAS2R43, hTAS2R44, hTAS2R46, or hTAS2R47 stimulated by a corresponding agonist of said receptor at least by 10% (e.g. at least 10%, 15%, 20%, 30%, 40%, 50%, 60%, 70%, 80%, 90%, 95%, 98%, 99%, 99.5% or 100%) at the same molar concentration. Suitable agonists are listed in Table 1.

The methods according to the first and the aspect may also be modified into methods for identifying agonists of bitter taste receptors hTAS2R40, hTAS2R43, hTAS2R44, hTAS2R46, or hTAS2R47.

Such modified methods of the first or the second aspect comprise the steps of (1) contacting a bitter taste receptor encoded by a polynucleotide as defined above for the first or the second aspect or a host cell genetically engineered with said polynucleotide or with a vector containing said polynucleotide to express said bitter taste receptor with a potential agonist that is structurally related to 3P hydroxy dihydro costunolide or 3β hydroxy pelenolide; and (2) determining whether the potential agonist induces bitter taste receptor activity.

In preferred embodiments of these methods for identifying agonists of bitter taste receptors, an identified potential agonist stimulates the activity of hTAS2R40, hTAS2R43, hTAS2R44, hTAS2R46, or hTAS2R47 to at least 50% (e.g. at least 50%, 60%, 70%, 80%, 90%, 95%, 100%, 110%, 120%, 130%, 140%, 150%, 200%, 250% 300%, 400%, 500%, 1000%) of the activity elicited by an agonist listed in Table 1 at the same molar concentration.

The activity of the receptors described herein can be assessed using a variety of in vitro and in vivo assays to determine functional, chemical, and physical effects, e.g., measuring ligand binding, secondary messengers (e.g., cAMP, cGMP, $IP_3$, DAG, or $Ca^{2+}$) ion flux, phosphorylation levels, transcription levels of reporter constructs, neurotransmitter levels, and the like. Such assays are used in the method of the present invention to test for the activity of the receptors.

The effects of the test compounds on the function of the receptors can be measured by examining any of the parameters described above. Any suitable physiological change that affects receptor activity can be used to assess the influence of a test compound on the receptors usable in the methods of this invention. When the functional consequences are determined using intact cells or animals, these consequences can be measured by any means known to those skilled in the art, e.g. patch clamping, voltage-sensitive dyes, whole cell currents, radioisotope efflux, inducible markers, oocyte bitter taste receptor gene expression; tissue culture cell bitter taste receptor expression; transcriptional activation of bitter taste receptor genes; ligand binding assays; voltage, membrane potential and conductance changes; ion, preferably sodium or calcium ion flux assays, for example measuring calcium levels using calcium sensitive dyes such as Fluo-3, Fluo-4 or Fura-2; changes in intracellular second messengers such as cAMP, cGMP, and inositol triphosphate ($IP_3$); changes in intracellular calcium levels; neurotransmitter release, and the like. These assays may be performed on intact cells expressing a bitter taste receptor polypeptide, on permeabilized cells, or on membrane fractions produced by standard methods.

Preferred assays for G-protein coupled receptors include cells that are loaded with ion sensitive dyes to report receptor activity. In assays for identifying modulatory compounds, changes in the level of ions in the cytoplasm or membrane voltage will be monitored using an ion sensitive or membrane voltage fluorescent indicator, respectively. For G-protein coupled receptors, promiscuous G-proteins such as Gα15 and Gα16 and chimeric G-proteins can be used in the assay of choice (see, for example, Wilkie et al. (1991) Proc. Nat. Acad. Sci. USA 88: 10049-10053). Such promiscuous G-proteins allow coupling of a wide range of receptors to G-protein dependent signal pathways.

Receptor activation typically initiates subsequent intracellular events, e.g. increases in second messengers such as $IP_3$, which releases intracellular stores of calcium ions. Activation of some G-protein coupled receptors stimulates the formation of inositol trisphosphate through phospholipase C-mediated hydrolysis of phosphatidylinositol bisphosphate (Berridge & Irvine (1984) Nature 312: 315-21). $IP_3$ in turn stimulates the release of intracellular calcium ion stores. Thus, a change in cytoplasmic calcium ion levels, or a change in second messenger levels such as $IP_3$ can be used to assess G-protein coupled receptor function. Cells expressing such G-protein coupled receptors may exhibit increased cytoplasmic calcium levels as a result of contribution from both intracellular stores and via activation of ion channels, in which case it may be desirable, although not necessary, to conduct such assays in calcium-free buffer, optionally supplemented with a chelating agent such as EGTA, to distinguish fluorescence response resulting from calcium release from internal stores.

Thus, in preferred embodiments of the first aspect, hTAS2R40 bitter taste receptor activity, hTAS2R43 bitter taste receptor activity, hTAS2R44 bitter taste receptor activity, hTAS2R46 bitter taste receptor activity, or hTAS2R47 bitter taste receptor activity is determined by measuring a change in concentration of an intracellular messenger. Preferably, the intracellular messenger is selected from the group consisting of $Ca^{2+}$, $IP_3$, and cAMP.

In preferred embodiments of the second aspect, hTAS2R40 bitter taste receptor activity, hTAS2R43 bitter taste receptor activity, hTAS2R46 bitter taste receptor activity, or hTAS2R47 bitter taste receptor activity is determined by measuring a change in concentration of an intracellular messenger. Preferably, the intracellular messenger is selected from the group consisting of $Ca^{2+}$, $IP_3$, and cAMP.

In a preferred embodiment, receptor activity is measured by expressing a bitter taste receptor described herein (hTAS2R40, hTAS2R43, hTAS2R44, hTAS2R46, or hTAS2R47) in a heterologous cell with a G-protein, such as Gα15, Gα16, transducin, gustducin, or a chimeric G-protein that links the receptor to a phospholipase C signal transduction pathway.

In another aspect of the invention, only the extracellular domain of the respective bitter taste receptor is expressed as a chimeric transmembrane fusion protein. A preferred cell line is HEK-293, although other mammalian cell lines are also preferred such as CHO and COS cells. Modulation of taste transduction is assayed by measuring changes in intracellular $Ca^{2+}$ levels, which change in response to modulation of the receptor signal transduction pathway via administration of a molecule that associates with the receptor. Changes in $Ca^{2+}$ levels are optionally measured using fluorescent $Ca^{2+}$ indicator dyes and fluorometric imaging. The activity of the signalling molecule and the increase or decrease of that activity in response to the potential antagonist can be determined as outlined above with respect to the identification of bitter taste receptor taste activity. The respectively indicated percental decreases of the activity, which are required to qualify as antagonist, do apply mutatis mutandis. Additionally, the term "contacting" has the meaning as outlined above. Preferably the signalling molecule and/or the promiscuous G-protein have been introduced into the cell. The preferred types of cell lines are those indicated below.

In yet another embodiment, the ligand-binding domains of the receptors can be employed in vitro in soluble or solid-state reactions to assay for ligand binding. Ligand binding to a bitter taste receptor, or a domain of a bitter taste receptor, such as e.g. the extracellular domain, can be tested in solution, in a bilayer membrane attached to a solid phase, in a lipid monolayer or vesicles. Thereby, the binding of a modulator to the receptor, or domain, can be observed using changes in spectroscopic characteristics, e.g. fluorescence, fluorescence polarization, plasmon resonance, absorbance or refractive index; or hydrodynamic (e.g. shape), chromatographic, or solubility properties, as is generally known in the art.

The polynucleotide employed in the first and the second aspect of the present invention encodes a polypeptide that still exhibits essentially the same activity as the mature hTAS2R40, hTAS2R43, hTAS2R44, hTAS2R46, or hTAS2R47 bitter taste receptor, respectively, i.e. has "bitter taste receptor activity". Preferably the polypeptide has at least 10% (e.g., at least: 10%, 20%; 30%; 40%; 50%; 60%; 70%; 80%; 90%; 95%; 98%; 99%; 99.5%; or 100% or even more) of the activity of the full-length mature hTAS2R40, hTAS2R43, hTAS2R44, hTAS2R46, or hTAS2R47. The amino acid sequences of full length full length hTAS2R40, full length hTAS2R43, full length hTAS2R44, full length hTAS2R46, or full length hTAS2R47 are shown in SEQ ID NO: 14, SEQ ID NO: 6, SEQ ID NO: 8, SEQ ID NO: 10, SEQ ID NO: 12, respectively.

The hTAS2R40 polynucleotide, hTAS2R43 polynucleotide, hTAS2R44 polynucleotide, hTAS2R46 polynucleotide, or hTAS2R47 polynucleotide molecules usable in the first or second aspect of the present invention can be DNA, cDNA, genomic DNA, synthetic DNA, or RNA, and can be double-stranded or single-stranded, the sense strand and/or an antisense strand. Segments of these molecules are also considered within the scope of the invention, and can be produced by, for example, the polymerase chain reaction (PCR) or generated by treatment with one or more restriction endonucleases. A ribonucleic acid (RNA) molecule can be produced by in vitro transcription.

The polynucleotide molecules usable in the first or second aspect of the present invention can contain naturally occurring sequences, or sequences that differ from those that occur naturally, but, due to the degeneracy of the genetic code, encode the same polypeptide (for example, the polypeptide as shown in SEQ ID NO: 14, 6, 8, 10, or 12). In addition, these nucleic acid molecules are not limited to coding sequences, e.g., they can include some or all of the non-coding sequences that lie upstream or downstream from a coding sequence.

The polynucleotide molecules of the invention can be synthesized in vitro (for example, by phosphoramidite-based synthesis) or obtained from a cell, such as the cell of a bacterium or a mammal. The nucleic acids can be those of a human but also include orthologous polynucleotides derived from a non-human primate, mouse, rat, guinea pig, cow, sheep, horse, pig, rabbit, dog, or cat as long as they fulfil the criteria set out above. Combinations or modifications of the polynucleotides within these types of nucleic acids are also encompassed. Means to identify orthologous polynucleotide molecules of the invention are available to a person of skill in the art and comprise the use of BLAST searches (see above) and database mining of databases such as the EMBL, NCBI and other databases comprising polynucleotides and amino acid sequences.

In addition, the polynucleotides usable in the first or second aspect of the present invention can encompass segments that are not found as such in the natural state. Thus, the invention encompasses recombinant nucleic acid molecules incorporated into a vector (for example, a plasmid or viral vector) or into the genome of a heterologous cell (or the genome of a homologous cell, at a position other than the natural chromosomal location). Recombinant nucleic acid molecules and uses therefore are discussed further below.

In certain preferred embodiments, the method according to the first or the second aspect of the present invention uses isolated nucleic acid molecules which are at least 50% (or 55%, 60%, 65%, 70%, 75%, 80%, 85%, 90%, 95%, or 98%) identical to: (a) a nucleic acid molecule that encodes the polypeptide of SEQ ID NO: 14, 6, 8, 10, or 12; (b) the polynucleotide sequence of SEQ ID NO: 13, 5, 7, 9, or 11 and (c) a nucleic acid molecule which includes a segment of at least 30 (e.g., at least 30, 40, 50, 60, 80, 100, 125, 150, 175, 200, 250, 300, 400, 500, 600, 700, 800, 850, and 900) contiguous nucleotides of SEQ ID NO: 13, 5, 7, 9, or 11, in as long as these nucleic acid molecules encode a polypeptide having hTAS2R40 bitter taste receptor activity, hTAS2R43 bitter taste receptor activity, hTAS2R44 bitter taste receptor activity, hTAS2R46 bitter taste receptor activity, or hTAS2R47 bitter taste receptor activity.

The polynucleotides or proteins useable in the first or the second aspect of the present invention can be comprised in a vector containing the polynucleotide(s) or a protein encoded by above-mentioned polynucleotide.

In a preferred embodiment a vector useable in the methods of the present invention comprises plasmids, phagemids, phages, cosmids, artificial mammalian chromosomes, knockout or knock-in constructs, viruses, in particular adenoviruses, vaccinia viruses, attenuated vaccinia viruses, canary pox viruses, lentivirus (Chang, L J. and Gay, E. E. (2001) Curr. Gene Therap. 1: 237-251), herpes viruses, in particular Herpes simplex virus (HSV-I, Carlezon, W. A. et al. (2000) Crit. Rev. Neurobiol. 14: 47-67), baculovirus, retrovirus, adeno-associated-virus (AAV, Carter, P J. and Samulski, R J. (2000) J. Mol. Med. 6:17-27), rhinovirus, human immune deficiency virus (HIV), filovirus and engineered versions thereof (see, for example, Cobinger G. P. et al. (2001) Nat. Biotechnol. 19:225-30), virosomes, "naked" DNA liposomes, and nucleic acid coated particles, in particular gold spheres. Particularly preferred are viral vectors like adenoviral vectors or retroviral vectors (Lindemann et al. (1997) Mol. Med. 3: 466-76 and Springer et al. (1998) Mol. Cell. 2: 549-58). Liposomes are usually small unilamellar or multilamellar vesicles made of cationic, neutral and/or anionic lipids, for example, by ultrasound treatment of liposomal suspensions. The DNA can, for example, be ionically bound to the surface of the liposomes or internally enclosed in the liposome. Suitable lipid mixtures are known in the art and comprise, for example, DOTMA (1,2-Dioleoyloxypropyl-3-trimethylammoniumbromide) and DOPE (Dioleoyl-phosphatidyl-ethanolamin) which both have been used on a variety of cell lines.

Nucleic acid coated particles are another means for the introduction of nucleic acids into cells using so called "gene guns", which allow the mechanical introduction of particles into cells. Preferably the particles itself are inert, and therefore, are in a preferred embodiment made out of gold spheres.

In a further embodiment polynucleotides usable in the first or second aspect of the present invention are operatively linked to expression control sequences allowing expression in prokaryotic and/or eukaryotic host cells. The transcriptional/translational regulatory elements referred to above include but are not limited to inducible and non-inducible, constitutive, cell cycle regulated, metabolically regulated promoters, enhancers, operators, silencers, repressors and other elements that are known to those skilled in the art and that drive or otherwise regulate gene expression. Such regulatory elements include but are not limited to regulatory elements directing constitutive expression like, for example, promoters transcribed by RNA polymerase III like, e.g. promoters for the snRNA U6 or scRNA 7SK gene, the cytomegalovirus hCMV immediate early gene, the early or late promoters of SV40 adenovirus, viral promoter and activator sequences derived from, e.g. NBV, HCV, HSV, HPV, EBV, HTLV, MMTV or HIV; which allow inducible expression like, for example, CUP-I promoter, the tet-repressor as employed, for example, in the tet-on or tet-off systems, the lac system, the trp system; regulatory elements directing tissue specific expression, preferably taste bud specific expression, e.g. PLCβ2 promoter or gustducin promoter, regulatory elements directing cell cycle specific expression like, for example, cdc2, cdc25C or cyclin A; or the TAC system, the TRC system, the major operator and promoter regions of phage A, the control regions of fd coat protein, the promoter for 3-phosphoglycerate kinase, the promoters of acid phosphatase, and the promoters of the yeast α- or α-mating factors.

Similarly, the polynucleotides usable in the first and the second aspect of the present invention can form part of a hybrid gene encoding additional polypeptide sequences, for example, a sequence that functions as a marker or reporter. Examples of marker and reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyl-transferase (XGPRT). As with many of the standard procedures associated with the practice of the method of the invention, skilled artisans will be aware of additional useful reagents, for example, additional sequences that can serve the function of a marker or reporter.

The methods according to the first and the second aspect of the present invention may also use hybrid polypeptides or polynucleotides encoding them. In general a hybrid polypeptide will include a first portion and a second portion; the first portion being one or more polypeptides selected from hTAS2R40, hTAS2R43, hTAS2R44, hTAS2R46, and hTAS2R47 polypeptides and the second portion being, for example, the reporter(s) described above or an Ig constant region or part of an Ig constant region, e.g. the CH2 and CH3 domains of IgG2a heavy chain. Other hybrids could include an antigenic tag or His tag to facilitate purification and/or detection. Recombinant nucleic acid molecules can also contain a polynucleotide sequence encoding the hTAS2R40 polypeptide, hTAS2R43 polypeptide, hTAS2R44 polypeptide, hTAS2R46 polypeptide, or hTAS2R47 polypeptide operatively linked to a heterologous signal sequence. Such signal sequences can direct the protein to different compartments within the cell and are well known to someone of skill in the art. A preferred signal sequence is a sequence that facilitates secretion of the resulting protein.

In order to express cDNAs encoding the receptors, one typically subclones receptor cDNA into an expression vector that contains a strong promoter to direct transcription, a transcription/translation terminator, and a ribosome-binding site for translational initiation. Suitable bacterial promoters are well known in the art, e.g., *E. coli*, *Bacillus* sp., and *Salmonella*, and kits for such expression systems are commercially available. Similarly eukaryotic expression systems for mammalian cells, yeast, and insect cells are well known in the art and are also commercially available. The eukaryotic expression vector may be, for example an adenoviral vector, an adeno-associated vector, or a retroviral vector.

In addition to the promoter, the expression vector typically contains a transcription unit or expression cassette that contains all the additional elements required for the expression of the receptor-encoding nucleic acid in host cells. A typical expression cassette thus contains a promoter operatively linked to the nucleic acid sequence encoding the receptor and signals required for efficient polyadenylation of the transcript, ribosome binding sites, and translation termination. The nucleic acid sequence encoding the receptor may typically be linked to a membrane-targeting signal such as the N-terminal 45 amino acids of the rat somatostatin receptor 3 sequence to promote efficient cell-surface expression of the recombinant receptor. Additional elements of the cassette may include, for example enhancers. An expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ, but there are many more known in the art to the skilled person that can be usefully employed.

Expression vectors containing regulatory elements from eukaryotic viruses are typically used in eukaryotic expression vectors, e.g. SV40 vectors, papilloma virus vectors, and vectors derived from Epstein-Barr virus. Other exemplary eukaryotic vectors include pMSG, pAV009/A.sup.+, pMTO10/A.sup.+, pMAMneo-5, baculovirus pDSVE, pcDNA3.1, pIRES and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable.

The elements that are typically included in expression vectors also include a replicon that functions in *E. coli*, a gene encoding drug resistance to permit selection of bacteria that harbour recombinant plasmids, and unique restriction sites in nonessential regions of the plasmid to allow insertion of eukaryotic sequences. The particular drug resistance gene chosen is not critical; any of the many drug resistance genes known in the art are suitable. The prokaryotic sequences are optionally chosen such that they do not interfere with the replication of the DNA in eukaryotic cells, if necessary.

Standard transfection methods can be used to produce bacterial, mammalian, yeast or insect cell lines that express large quantities of the receptor, which are then purified using standard techniques. Any of the well-known procedures for introducing foreign polynucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell. It is only necessary that the particular genetic engineering procedure used be capable of successfully introducing at least one gene into the host cell capable of expressing the receptor.

After the expression vector is introduced into the cells, the transfected cells may be cultured under conditions favoring expression of the receptor, which is recovered from the culture using standard techniques. For example the cells may be burst open either mechanically or by osmotic shock before being subject to precipitation and chromatography steps, the nature and sequence of which will depend on the particular recombinant material to be recovered. Alternatively, the recombinant protein may be recovered from the culture medium in which the recombinant cells had been cultured.

In preferred embodiments of the present invention, a host cell genetically engineered with a polynucleotide or a vector as outlined above is used. The host cells that may be used in the methods of the present invention include but are not limited to prokaryotic cells such as bacteria (for example, *E.*

*coli* and *B. subtilis*), which can be transformed with, for example, recombinant bacteriophage DNA, plasmid DNA, or cosmid DNA expression vectors containing the polynucleotide molecules of the invention; simple eukaryotic cells like yeast (for example, *Saccharomyces* and *Pichia*), which can be transformed with, for example, recombinant yeast expression vectors containing the polynucleotide molecule of the invention; insect cell systems like, for example, Sf9 or Hi5 cells, which can be infected with, for example, recombinant virus expression vectors (for example, baculovirus) containing the polynucleotide molecules; amphibian cells, e.g. *Xenopus oocytes*, which can be injected with, for example, plasmids; plant cell systems, which can be infected with, for example, recombinant virus expression vectors (for example, cauliflower mosaic virus (CaMV) or tobacco mosaic virus (TMV)) or transformed with recombinant plasmid expression vectors (for example, Ti plasmid) containing a hTAS2R40 polynucleotide sequence, hTAS2R43 polynucleotide sequence, hTAS2R44 polynucleotide sequence, hTAS2R46 polynucleotide sequence, or hTAS2R47 polynucleotide sequence; or mammalian cell systems (for example, COS, CHO, BHK, HEK293, VERO, HeLa, MDCK, Wi38, and NIH 3T3 cells), which can be transformed with recombinant expression constructs containing, for example, promoters derived, for example, from the genome of mammalian cells (for example, the metallothionein promoter) from mammalian viruses (for example, the adenovirus late promoter and the vaccinia virus 7.5K promoter) or from bacterial cells (for example, the tet-repressor binding is employed in the tet-on and tet-off systems). Also useful as host cells are primary or secondary cells obtained directly from a mammal and transfected with a plasmid vector or infected with a viral vector. Depending on the host cell and the respective vector used to introduce the polynucleotide of the invention the polynucleotide can integrate, for example, into the chromosome or the mitochondrial DNA or can be maintained extrachromosomally like, for example, episomally or can be only transiently comprised in the cells.

In a preferred embodiment, a bitter taste receptor usable in the present invention (hTAS2R40, hTAS2R43, hTAS2R44, hTAS2R46, or hTAS2R47), expressed by such cells is functional and has bitter taste receptor activity, i.e. upon binding to one or more bitter molecules it triggers an activation pathway in the cell. The cells are preferably mammalian (e.g., human, non-human primate, horse, bovine, sheep, pig, dog, cat, goat, rabbit, mouse, rat, guinea pig, hamster, or gerbil) cells, insect cells, bacterial cells, or fungal (including yeast) cells. The polypeptides usable in the methods of the invention include all those disclosed herein and functional fragments of these polypeptides. As used herein, a functional fragment of the bitter taste receptor hTAS2R40, hTAS2R43, hTAS2R44, hTAS2R46, or hTAS2R47 is a fragment of the respective bitter taste receptor that is shorter than the corresponding full-length bitter taste receptor polypeptide, but that has at least 10% (e.g. at least: 10%, 20%, 30%, 40%, 50%, 60%, 70%, 80%, 90%, 95%, 98%, 99%, 99.5%, 100%, 150%, 200%, 500%, 1000%, 10000% or even more) of the ability of the full-length hTAS2R40, hTAS2R43, hTAS2R44, hTAS2R46, or hTAS2R47, respetively, as shown in SEQ ID NO: 40, SEQ ID NO: 6, SEQ ID NO: 8, SEQ ID NO: 10, or SEQ ID NO: 12, respectively, to be stimulated by bitter substances such as the bitter receptor agonists described herein (e.g. the agonists listed above in Table 1). Binding assays and bitter substances for bitter taste receptors hTAS2R40, hTAS2R43, hTAS2R44, hTAS2R46, and hTAS2R47 are described above and below. The polypeptides can also include fusion proteins that contain either a full-length hTAS2R40 polypeptide, hTAS2R43 polypeptide, hTAS2R44 polypeptide, hTAS2R46 polypeptide, or hTAS2R47 polypeptide or a functional fragment thereof fused to an unrelated amino acid sequence. The unrelated sequences can add further functional domains or signal peptides.

The polypeptides can be any of those described above but with not more than 50 (e.g., not more than: 50, 45, 40, 35, 30, 25, 20, 15, 14, 13, 12, 11, 10, nine, eight, seven, six, five, four, three, two, or one) conservative substitutions as defined above. All that is required of a polypeptide having one or more conservative substitutions is that it has at least 10% (e.g., at least: 10%, 20%; 30%; 40%; 50%; 60%; 70%; 80%; 90%; 95%; 98%; 99%; 99.5%; 100%, 150%, 200%, 500%, 1000%, 10000% or even more) of the ability of the full-length hTAS2R40, full-length hTAS2R43, full-length hTAS2R44, full-length hTAS2R46, or full-length hTAS2R47 to be stimulated by an agonist of hTAS2R40, hTAS2R43, hTAS2R44, hTAS2R46, or hTAS2R47, respectively, e.g. an agonist listed in Table 1.

Polypeptides and fragments of the polypeptides usable in the method of the present invention can be modified, for example, for in vivo use by the addition of blocking agents, at the amino- and/or carboxyl-terminal ends, to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

The compounds tested as modulators, i.e. potential antagonists and agonists, of the receptors can be any small chemical compound, or a biological entity, such as a protein, sugar, nucleic acid or lipid. Typically, test compounds will be small chemical molecules. Typically, a "small molecule" has a molar mass of 1000 g/mol or less, preferably 500 g/mol or less. Essentially any chemical compound can be used as a potential modulator or ligand in the assays of the invention, although knowledge of the ligand specificity of an individual receptor would enable the skilled person to make an intelligent selection of interesting compounds. The assays may be designed to screen large chemical libraries by automating the assay steps and providing compounds from any convenient source to assays, which are typically run in parallel (e.g., in microtiter formats on microtiter plates in robotic assays). The skilled person will understand that there are many suppliers of libraries of chemical compounds.

Assays may be run in high throughput screening methods that involve providing a combinatorial chemical or peptide library containing a large number of potential therapeutic or tastant compounds (that are potential ligand compounds). Such libraries are then screened in one or more assays, as described herein, to identify those library members (particular chemical species or subclasses) that display a desired characteristic activity. The compounds thus identified can serve as lead compounds to further develop modulators for final products, or can themselves be used as actual modulators. A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art and no more needs to be stated here.

In the high-throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g. 96) modulators. If 1536 well plates are used, then a single plate can easily assay from about 100 to about 1500 different compounds. It is possible to assay several different plates per day; assay screens for up to about 6,000-20,000 different compounds are possible using the integrated systems of the invention.

The term "potential antagonist", preferably comprises 3β hydroxy dihydro costunolide (formula (I) in FIG. 1) or 3β hydroxy pelenolide (formula (II) in FIG. 1) and substances structurally related thereto in a non-purified, partially purified or purified state. Preferably, the term "potential antagonist" comprises any perceivable chemical substance or combination thereof having a structure according to formula (III), (IV), (V), or (VI) in a non-purified, partially purified or purified state. The potential antagonist is selected on the basis of its antagonizing behaviour. An "isolated antagonist" of hTAS2R40 bitter taste receptor activity, hTAS2R43 bitter taste receptor activity, hTAS2R44 bitter taste receptor activity, hTAS2R46 bitter taste receptor activity, or hTAS2R47 bitter taste receptor activity is a substance which reduces the activity of hTAS2R40, hTAS2R43, hTAS2R44, hTAS2R46, or hTAS2R47 stimulated by a bitter taste receptor agonist of hTAS2R40, hTAS2R43, hTAS2R44, hTAS2R46, or hTAS2R47, respectively, preferably selected from the group of agonists (bitter substances) listed in Table 1 above. Preferably this reduction is by at least 10% (e.g., at least: 10%, 15%; 20%; 30%; 40%; 50%; 60%; 70%; 80%; 90%; 95%; 98%; 99%; 99.5%; or 100%), preferably at the same molar concentration. The extent of the lowering of the hTAS2R40 bitter taste receptor activity, hTAS2R43 bitter taste receptor activity, hTAS2R44 bitter taste receptor activity, hTAS2R46 bitter taste receptor activity, or hTAS2R47 bitter taste receptor activity caused by the antagonist is determined in the presence of said agonist, e.g. one of the compounds listed in Table 1 or a structurally related compound, which may be added prior, concomitantly or after addition of the antagonist. Preferably, the identified antagonist exerts this inhibitory activity, if present in the same molar, 2-fold, 5-fold, 10-fold, 50-fold or 100-fold molar concentration as the agonist.

The term "potential agonist", preferably comprises substances other than the antagonists 3β hydroxy dihydro costunolide (formula (I) in FIG. 1) or 3β hydroxy pelenolide (formula (II) in FIG. 1) but structurally related to either one of these compounds in a non-purified, partially purified or purified state. Preferably, the term "potential agonist" comprises any perceivable chemical substance or combination thereof (other than 3β hydroxy dihydro costunolide or 3β hydroxy pelenolide) having a structure according to formula (III), (IV), (V), or (VI) in a non-purified, partially purified or purified state. The potential agonist is selected on the basis of its receptor stimulating behaviour. An "isolated agonist" of hTAS2R40 bitter taste receptor activity, hTAS2R43 bitter taste receptor activity, hTAS2R44 bitter taste receptor activity, hTAS2R46 bitter taste receptor activity, or hTAS2R47 bitter taste receptor activity is a substance which stimulates the activity of hTAS2R40, hTAS2R43, hTAS2R44, hTAS2R46, or hTAS2R47, respectively, to at least 50% (e.g. at least 60%, 70%, 80%, 90%, 95%, 100%, 110%, 120%, 130%, 140%, 150%, 200%, 250% 300%, 400%, 500%, 1000%) of the activity elicited by one of the compounds listed in Table 1 at the same molar concentration. The extent of activation of the respective bitter taste receptor caused by the agonist can be determined by assays described throughout this specification.

In a third aspect the present invention is directed to a method of isolating an antagonist of hTAS2R40 bitter taste receptor activity, hTAS2R43 bitter taste receptor activity, hTAS2R44 bitter taste receptor activity, hTAS2R46 bitter taste receptor activity, or hTAS2R47 bitter taste receptor activity, the method comprising carrying out the method according to the first or the second aspect and further comprising the step:

(3) isolating a potential antagonist that reduces the activity of hTAS2R40, hTAS2R43, hTAS2R44, hTAS2R46, or hTAS2R47 stimulated by an agonist of hTAS2R40, hTAS2R43, hTAS2R44, hTAS2R46, or hTAS2R47, respectively.

In other words, the method of the third aspect includes the method steps of the first aspect or the method steps of the second aspect.

When including the method of the first aspect, the method of the third aspect is directed to a method of isolating an antagonist of hTAS2R40 bitter taste receptor activity, hTAS2R43 bitter taste receptor activity, hTAS2R44 bitter taste receptor activity, hTAS2R46 bitter taste receptor activity, or hTAS2R47 bitter taste receptor activity, the method comprising carrying out the method according to the first aspect and further comprising the step:

(3) isolating a potential antagonist that reduces the activity of hTAS2R40, hTAS2R43, hTAS2R44, hTAS2R46, or hTAS2R47 stimulated by an agonist of hTAS2R40, hTAS2R43, hTAS2R44, hTAS2R46, or hTAS2R47, respectively.

When including the method of the second aspect, the method of the third aspect is directed to a method of isolating an antagonist of hTAS2R40 bitter taste receptor activity, hTAS2R43 bitter taste receptor activity, hTAS2R46 bitter taste receptor activity, or hTAS2R47 bitter taste receptor activity, the method comprising carrying out the method according to the second aspect and further comprising the step:

(3) isolating a potential antagonist that reduces the activity of hTAS2R40, hTAS2R43, hTAS2R46, or hTAS2R47 stimulated by an agonist of hTAS2R40, hTAS2R43, hTAS2R46, or hTAS2R47, respectively.

In a fourth aspect the present invention is directed to a method for the production of a modified antagonist of hTAS2R40, hTAS2R43, hTAS2R44, hTAS2R46, or hTAS2R47, wherein an antagonist identified in a method according to the first or the second aspect, an antagonist isolated by the method of the third aspect, 3β hydroxy dihydro costunolide (formula (I) in FIG. 1), or 3β hydroxy pelenolide (formula (II) in FIG. 1) is modified by the addition and/or exchange of at least one substituent. Preferably, the antagonist is modified by the addition and/or exchange of 1 to 6 (e.g. 1, 2, 3, 4, 5, or 6) substituents. In a preferred embodiment of the fourth aspect, a modified antagonist is selected based on that it reduces the activity of hTAS2R40, hTAS2R43, hTAS2R44, hTAS2R46, or hTAS2R47 stimulated by an agonist of hTAS2R40, hTAS2R43, hTAS2R44, hTAS2R46, or hTAS2R47, respectively, at least as good as the previously identified antagonist, 3β hydroxy dihydro costunolide, or 3β hydroxy pelenolide at the same molar concentration.

As a further step after measuring the antagonizing effect of a potential antagonist and after having measured the decrease of bitter taste for at least two different potential antagonists at least one potential antagonist can be selected, for example, on grounds of the detected decrease of intracellular release of calcium.

Thus, in accordance with the fourth aspect of the invention the selected, e.g. isolated, antagonist is chemically modified in a further step. This chemical modification can be effected by a variety of methods known in the art, which include without limitation the introduction of one or more (preferably one, two, three, four, five, or six) substituents and/or the exchange of one or more (preferably one, two, three, four, five, or six) substituents. Preferably, the substituents introduced or exchanged are in each instance independently selected from the group consisting of halogen, in particular F, Cl, Br or I; —$NO_2$; —CN; —$OR^c$; —$NR^aR^b$; —$COOR^c$; —$CONR^aR^b$; —$NR^aCOR^c$; —$NR^aCOR^b$; —$NR^aCONR^aR^a$; —$NR^aSO_2D$; —$COR^c$; —$SO_2NR^aR^b$; —$OOCR^c$; —$CR^cR^dOH$; $R^cOH$; and -D;

$R^a$ and $R^b$ is each independently selected from the group consisting of hydrogen; alkyl, in particular $C_1$-$C_6$ alkyl, e.g. $C_1$, $C_2$, $C_3$, $C_4$, $C_5$, or $C_6$ alkyl, preferably methyl, ethyl, propyl (n-propyl or iso-propyl), butyl (n-butyl, sec-butyl, iso-butyl, or tert-butyl), pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, in particular $C_2$-$C_6$ alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantyl, decahydro-naphthalenyl; heterocycloalkyl, e.g. $C_3$-$C_{14}$— heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydro-quinolinyl, decahydro-isoquinolinyl, decahydro-quinoxalinyl, decahydro-quinazolinyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; aryl, in particular phenyl, naphthalenyl, anthracenyl, or phenanthrenyl; aralkyl; preferably $C_1$-$C_6$ aralkyl, e.g. $C_1$, $C_2$, $C_3$, $C_4$, $C_5$, or $C_6$ aralkyl; heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, 1-benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and —$NR^cR^d$;

$R^c$ and $R^d$ is each independently selected from the group consisting of hydrogen, alkyl, in particular $C_1$-$C_6$ alkyl, e.g. $C_1$, $C_2$, $C_3$, $C_4$, $C_5$, or $C_6$ alkyl, preferably methyl, ethyl, propyl (n-propyl or iso-propyl), butyl (n-butyl, sec-butyl, iso-butyl, or tert-butyl), pentyl, hexyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantyl, decahydro-naphthalenyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-Spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; aryl, in particular phenyl, naphthalenyl, anthracenyl, or phenanthrenyl; heteroaryl, in particular furanyl, thienyl, oxazolyl, isoxazolyl, oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, 1-benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; and aralkyl, preferably $C_1$-$C_6$ aralkyl, e.g. $C_1$, $C_2$, $C_3$, $C_4$, $C_5$, or $C_6$ aralkyl; or together form a heteroaryl, in particular, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, indolyl, isoindolyl, 1H-indazolyl, benzimidazolyl, indoxazinyl, 2,1-benzisoxazolyl, 1,2-benzisothiazolyl, 2,1-benzisothiazolyl, benzotriazolyl, quinolinyl, isoquinolinyl; 2,3-benzodiazinyl, quinoxalinyl, quinazolinyl, 1,2,3-benzotriazinyl, or 1,2,4-benzotriazinyl; optionally substituted; and D is selected from the group consisting of alkyl, in particular $C_1$-$C_6$ alkyl, e.g. $C_1$, $C_2$, $C_3$, $C_4$, $C_5$, or $C_6$ alkyl, preferably methyl, ethyl, propyl (n-propyl or iso-propyl), butyl (n-butyl, sec-butyl, iso-butyl, or tert-butyl), pentyl, hexyl; alkenyl, in particular $C_1$-$C_6$ alkenyl, e.g. $C_1$, $C_2$, $C_3$, $C_4$, $C_5$, or $C_6$ alkenyl, preferably methenyl, ethenyl, 1-propenyl, 2-propenyl, 1-iso-propenyl, 2-iso-propenyl, 1-butenyl, 2-butenyl, 3-butenyl; alkynyl, e.g. $C_2$, $C_3$, $C_4$, $C_5$, or $C_6$ alkynyl; cycloalkyl, in particular $C_3$-$C_{14}$-cycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-cycloalkyl, in particular cyclopropyl, cyclobutyl, cyclopentyl, cyclohexyl, cycloheptyl, cyclooctyl, cyclononyl, cyclodecyl, spiro[3,3]heptyl, spiro[3,4]octyl, spiro[4,3]octyl, spiro[3,5]nonyl, spiro[5,3]nonyl, spiro[3,6]decyl, spiro[6,3]decyl, spiro[4,5]decyl, spiro[5,4]decyl, bicyclo[4.1.0]heptyl, bicyclo[3.2.0]heptyl, bicyclo[2.2.1]heptyl, bicyclo[2.2.2]octyl, bicyclo[5.1.0]octyl, bicyclo[4.2.0]octyl, octahydro-pentalenyl, octahydro-indenyl, decahydro-azulenyl, adamantyl, decahydro-naphthalenyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$-alkoxy-$C_1$-$C_6$-alkyl, e.g. methoxymethyl, ethoxymethyl, propoxymethyl, methoxyethyl, ethoxyethyl, propoxyethyl, methoxypropyl, ethoxypropyl, or propoxypropyl; heterocycloalkyl, e.g. $C_3$-$C_{14}$-heterocycloalkyl, e.g. $C_3$, $C_4$, $C_5$, $C_6$, $C_7$, $C_8$, $C_9$, $C_{10}$, $C_{11}$, $C_{12}$, $C_{13}$ or $C_{14}$-heterocycloalkyl, in particular piperidinyl, morpholinyl, 1,3-diazacyclohexane, 1,8 diaza-spiro-[4,5]decyl, 1,7 diaza-spiro-[4,5]decyl, 1,6 diaza-spiro-[4,5]decyl, 2,8 diaza-spiro[4,5]decyl, 2,7 diaza-spiro[4,5]decyl, 2,6 diaza-spiro[4,5]decyl, 1,8 diaza-spiro-[5,4]decyl, 1,7 diaza-spiro-[5,4]decyl, 2,8 diaza-spiro-[5,4]decyl, 2,7 diaza-spiro[5,4]decyl, 3,8 diaza-spiro[5,4]decyl, 3,7 diaza-spiro[5,4]decyl, 1-aza-7,11-dioxo-spiro[5,5]undecyl, 1,4-diazabicyclo[2.2.2]oct-2-yl, tetrahydrofuran-2-yl, tetrahydrofuranyl, tetrahydrothienyl, tetrahydrothienyl, piperazinyl, decahydroquinolinyl, decahydro-isoquinolinyl, decahydro-quinoxalinyl, decahydro-quinazolinyl; an alicyclic system, which may comprise one or more heteroatoms, e.g. 1, 2, 3, or 4, preferably selected from the group consisting of O, S, or N; in particular 1,2-dihydropyridinyl, 1,2,5,6-tetrahydropyridinyl, 1,2,3,4-tetrahydropyridyl, 1,2-dihydropyrazyl, 1,2,3,4-tetrahydropyrazyl, cyclopropenyl, cyclobutenyl, cyclopentenyl, cyclohexenyl, cycloheptenyl; aryl, in particular phenyl, naphthalenyl, anthracenyl, or phenanthrenyl; and heteroaryl, in particular furanyl, thienyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, 1-benzothienyl, 2-benzothienyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, 1,2,3-benzotriazinyl, or 1,2,4-benzotriazinyl; optionally substituted.

The antagonist modified in accordance with the fourth aspect is then tested with the method according to the first aspect or the second aspect of the present invention. The modified antagonist is contacted with the hTAS2R40 polypeptide, hTAS2R43 polypeptide, hTAS2R44 polypeptide, hTAS2R46 polypeptide, or hTAS2R47 polypeptide as such or with the polypeptide expressed in a host cell, which has been contacted prior, concomitantly or after step (1) with an agonist of bitter taste receptor hTAS2R40, hTAS2R43, hTAS2R44, hTAS2R46, or hTAS2R47, respectively (suitable agonists for each receptor are listed in Table 1 above), and subsequently inhibition of the bitter taste receptor activity by the modified antagonist is measured. The inhibition of activation of the hTAS2R40 protein, hTAS2R43 protein, hTAS2R44 protein, hTAS2R46 protein, or hTAS2R47 protein can be measured, e.g. by the intracellular calcium release mediated. If needed, the steps of selecting the antagonist, modifying the compound, contacting the antagonist with a polypeptide or a host cell and measuring of the inhibition of the bitter taste receptor activity can be repeated a further time or any given number of times as required. The above described method is also termed "directed evolution" of an antagonist since it involves a multitude of steps including modification and selection, whereby antagonizing compounds are selected in an "evolutionary" process optimizing their capabilities with respect to a particular property, e.g. their ability to inhibit the activity of bitter taste receptor hTAS2R40, hTAS2R43, hTAS2R44, hTAS2R46, or hTAS2R47, in particular inhibit the intracellular release of calcium. Preferably, a modified antagonist is selected that reduces the activity of hTAS2R40, hTAS2R43, hTAS2R44, hTAS2R46, or hTAS2R47, stimulated by an agonist of hTAS2R40, hTAS2R43, hTAS2R44, hTAS2R46, or hTAS2R47, respectively, at least as good as the identified antagonist used as basis for the modified antagonist at the same molar concentration. More preferably, the modified antagonist shows a stronger reduction at the same molar concentration, preferably at least a 10% stronger reduction, 20%, 30%, 40%, 50%, 60%, or 70% stronger reduction. In a preferred embodiment, 3β hydroxy dihydro costunolide or 3β hydroxy pelenolide or an antagonist that is structurally related to one of these two compounds is used in the first round of above stated directed evolution methods.

The potential antagonists, which are employed in the methods of the present invention, in particular in the methods according to the first, second, third, and fourth aspect of the invention, can be synthesized by methods and standard procedures known to those skilled in the art, i.e. as described in the literature (for example in the standard works, such as Houben-Weyl, Methoden der organischen Chemie [Methods of Organic Chemistry], Georg-Thieme-Verlag, Stuttgart), to be precise under reaction conditions which are known to those skilled in the art and suitable for the said reactions.

Antagonists (or agonists) identified by methods described herein can be administered directly to a human subject to modulate, e.g. inhibit, bitter taste. Alternatively, such compounds can be formulated with other ingredients of preparations to be taken orally, for example, foods, including animal food, and beverages, pharmaceutical or nutraceutical or homeopathic preparations.

Thus, in a fifth aspect the present invention is directed to a method for the production of food, a food precursor material or additive employed in the production of foodstuff comprising the step of admixing an antagonist identified by a method according to the first or the second aspect, an antagonist isolated by the method of the third aspect, the modified antagonist produced according to the method of the fourth aspect, 3β hydroxy dihydro costunolide, 3β hydroxy pelenolide or an antagonist structurally related thereto with foodstuff, a food precursor material or additive employed in the production of foodstuff.

Bitter taste is a particular problem when orally administering pharmaceuticals, which often have an unpleasant bitter taste. In particular in elderly persons, children and chronically ill patients this taste can lead to a lack of compliance with a treatment regimen. In addition in veterinary applications the oral administration of bitter tasting pharmaceuticals can be problematic.

Therefore, in a sixth aspect the present invention is directed to a method for the production of a nutraceutical or pharmaceutical composition comprising the step of admixing the antagonist identified by a method according to the first or the second aspect, an antagonist isolated by the method of the third aspect, the modified antagonist produced according to the method of the fourth aspect, 3β hydroxy dihydro costunolide, 3β hydroxy pelenolide or an antagonist structurally related thereto with an active agent and optionally with one or more pharmaceutically acceptable carriers and/or adjuvants. In a preferred embodiment of the sixth aspect, the method further comprises the step of formulating the pharmaceutical composition into a pharmaceutically acceptable form.

In a seventh aspect the present invention is directed to a foodstuff, any foodstuff precursor material or additive employed in the production of foodstuff, wherein said foodstuff, said foodstuff precursor material, or said additive is producible according to the method of the fifth aspect.

In an eighth aspect the present invention is directed to a nutraceutical or pharmaceutical composition producible according to the method of the sixth aspect, comprising at least one nutraceutically or pharmaceutically active agent, and optionally one or more pharmaceutically acceptable carriers and/or adjuvants. These pharmaceutical and nutraceutical compositions comprise both products for human and animal consumption.

Regarding the fifth, sixth, seventh, and eighth aspect of the invention, the amount of compound including an antagonist (or agonist) of the present invention to be taken orally must be sufficient to effect a beneficial response in the subject, preferably human subject, and will be determined by the efficacy of the particular taste modulators and the existence, nature, and extent of any adverse side-effects that accompany the administration of a particular compound.

In a ninth aspect the present invention is directed to a use of a bitter taste receptor antagonist identified by a method according to the first or the second aspect, a bitter taste receptor antagonist isolated by the method of the third aspect, a modified bitter taste receptor antagonist producible according to the method of the fourth aspect, 3β hydroxy dihydro costunolide, 3β hydroxy pelenolide or an antagonist structurally related thereto to suppress bitter taste.

In a preferred embodiment of the ninth aspect, the bitter taste is suppressed by inhibiting and/or interfering with activation of bitter taste receptor hTAS2R40, bitter taste receptor hTAS2R43, bitter taste receptor hTAS2R44, bitter taste receptor hTAS2R46, or bitter taste receptor hTAS2R47.

Bitter taste receptors hTAS2R40, hTAS2R43, hTAS2R44, hTAS2R46, and hTAS2R47 are activated by one or more of the compounds listed in Table 1 above. Therefore, a preferred embodiment of the ninth aspect refers to a use of a bitter taste receptor antagonist to suppress bitter taste, in which the bitter taste is caused by one or more of the compounds listed in Table 1.

In a further preferred embodiment of the ninth aspect, the use is in a nutraceutical or a pharmaceutical composition, in food, a food precursor material or food additive.

In a related aspect, the present invention is directed to a use of an agonist of bitter taste receptor activity structurally related to 3β hydroxy dihydro costunolide or 3β hydroxy pelenolide to enhance bitter taste. In a preferred embodiment of this aspect the enhanced bitter taste is mediated by the bitter taste receptor hTAS2R40, bitter taste receptor hTAS2R43, bitter taste receptor hTAS2R44, bitter taste receptor hTAS2R46, or bitter taste receptor hTAS2R47.

The following figures and examples are merely illustrative of the present invention and should not be construed to limit the scope of the invention as indicated by the appended claims in any way.

BRIEF DESCRIPTION OF THE FIGURES

FIG. 6A-B show an investigation of the inhibitory mechanism of 3β hydroxy dihydro costunolide on hTAS2R46.

FIG. 6 (B) $EC_{50}$ values and maximum signal amplitudes of concentration-response curves. Coapplication of 100 μM 3β hydroxy dihydro costunolide results in a significant increase ($P<0.05$; One-way ANOVA, post-hoc test: Tukey, 95% confidence interval) of the strychnine $EC_{50}$ value indicating a competitive mechanism of inhibition. Data were collected of three independent experiments carried out in duplicates.

EXAMPLES

Methods

Heterologous Expression of Human TAS2 Receptors

Figure 1:
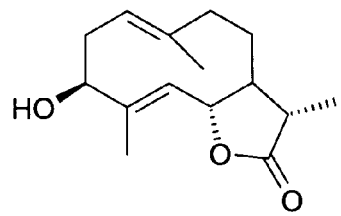
FIG. 1 shows the structural formulae of β hydroxy dihydro costunolide (formula I) and 3β hydroxy pelenolide (formula II).
Figure 1:
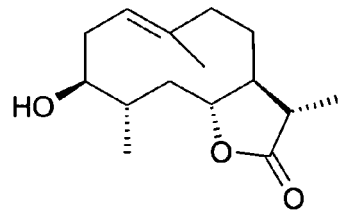

Human TAS2R cDNAs were cloned into pcDNA5/FRT (Invitrogen, San Diego, Calif.). For adequate plasma membrane targeting, receptor cDNA was fused to the aminoterminal sequence of the rat somatostatin type 3 receptor at the aminoterminus of the recombinant protein (Bufe, B., T. Hofmann, et al. (2002) Nat Genet. 32(3): 397-401). For immunological detection, the Herpes simplex Glycoprotein D epitope was supplemented at the carboxyterminus of the recombinant protein (Bufe et al., supra). Receptor constructs were transiently transfected into HEK293T cells stably expressing the chimeric G protein subunit Gα16gust44 (Ueda, T., S. Ugawa, et al. (2003) J Neurosci 23(19): 7376-80) using Lipofectamine 2000 (Invitrogen, San Diego, Calif.) in 96-well plates.

Calcium Imaging of Human TAS2 Receptors

Calcium Imaging experiments were performed 24 h after transfection using a Fluorometric Imaging Plate Reader (FLIPR, Molecular Devices, Munich, Germany) as previously described (Bufe et al., supra). Taste active compounds were ordered from Sigma (Sigma-Aldrich, Taufkirchen, Germany). Absinthin, 3β hydroxy dihydro costunolide and 3β hydroxy pelenolide were kindly provided by Giovanni Appendino (Novara, Italy). Test substances were directly dissolved in C1 buffer (130 mM NaCl, 10 mM Na-Hepes, 10 mM Glucose, 5 mM KCl, 2 mM $CaCl_2$, pH 7.4) or in DMSO, respectively. DMSO stocks were further diluted in C1 buffer not exceeding a final DMSO concentration of 1% on the cells. For the investigation of antagonistic effects, test substances were premixed. Agonists were applied at concentrations corresponding to $EC_{90}$, except where indicated otherwise (Table 2). Data were collected from 3 independent experiments performed in quadruplicates and processed with SigmaPlot (SPSS, Chicago, Ill.). Fluorescence signals after application of test substances were corrected for and normalized to background fluorescence ($\Delta F/F = (F-F_0)/F_0$), and baseline noise was subtracted. Calculation of dose-response curves was done by nonlinear regression using the function $$f(y) = ((a-d)/(1+(x/EC_{50})^{nH}) + d).$$

TABLE 2

Specific hTAS2R agonists used for the investigation of antagonistic effects of 3β hydroxy dihydro costunolide and 3β hydroxy pelenolide. Receptors hTAS2R41, -R42, -R45, -R48 and -R60 were not analyzed since there has no agonist been identified. Agonists were applied in concentrations that correspond to the $EC_{90}$ of the concerning receptor.

| receptor | agonist | agonist concentration (μM) |
|---|---|---|
| hTAS2R1 | trans-isocohumulone | 30 |
| hTAS2R3 | chloroquine | 1300 |
| hTAS2R4 | colchicine | 3000 |
| hTAS2R5 | denatonium saccharide | 3000* |
| hTAS2R7 | quinine sulfate | 10* |
| hTAS2R8 | chloramphenicol | 1000 |
| hTAS2R9 | ofloxacin | 6000 |
| hTAS2R10 | strychnine | 90 |
| hTAS2R13 | denatonium benzoate | 3000* |
| hTAS2R14 | aristolochic acids | 3 |
| hTAS2R16 | D-salicin | 3000 |
| hTAS2R38 | phenylthiocarbamide | 30 |
| hTAS2R39 | epigallocatechin gallate | 30 |
| hTAS2R40 | cohumulone | 0.3 |
| hTAS2R43 | aristolochic acids | 0.3 |
| hTAS2R44 | aristolochic acids | 3 |
| hTAS2R46 | picrotoxinin | 300 |
| hTAS2R47 | brucine | 100 |
| hTAS2R49 | cromolyn | 1000 |
| hTAS2R50 | andrographolide | 100 |

*Due to their low potency, agonists for hTAS2R5, -R7 and -R13 were used at their maximum applicable concentration that did not cause unspecific fluorescence signals in control cells.

Results

In a first series of experiments we tested the two sesquiterpene lactones 3β hydroxy dihydro costunolide (formula (I) in FIG. 1) and 3β hydroxy pelenolide (formula (II) in FIG. 1) for their ability to activate hTAS2 receptor-expressing HEK293T cells.

Figure 2:
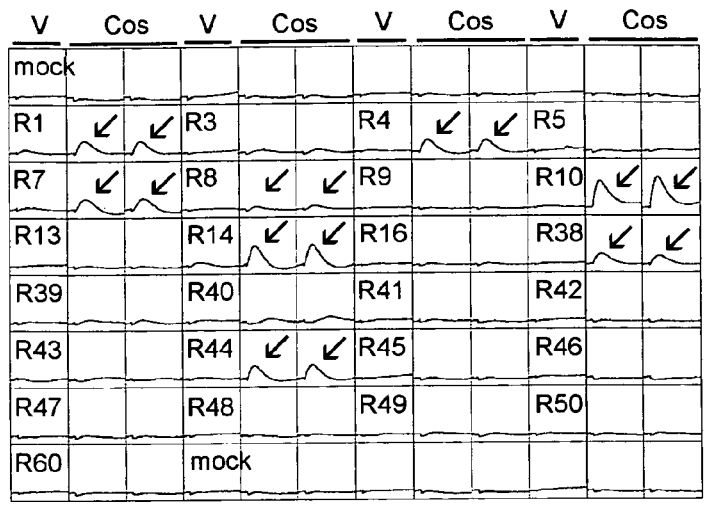
FIG. 2A-C show calcium responses of hTAS2R-transfected cells to the bath application of different Compounds. Calcium responses of hTAS2R-transfected cells to the bath application of 100 μM 3β hydroxy dihydro costunolide (FIG. 2A, Cos) and 3β hydroxy pelenolide (FIG. 2C, Pel). Arrows point to specific calcium responses to the test substances controlled by the application of vehicle (V). The response of hTAS2R38-expressing cells to 3β hydroxy dihydro costunolide is not specific as cells respond to DMSO contained in the solution (FIG. 2B). Scale: y, 15,000 counts. x, 8 min.
Figure 2:
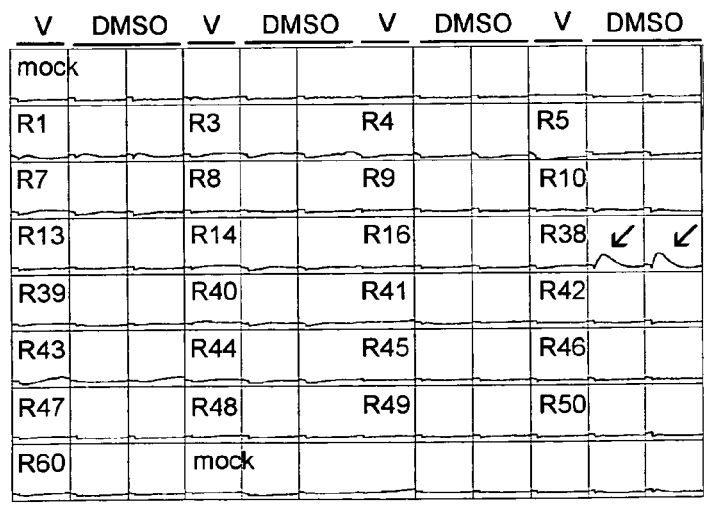
Figure 2:
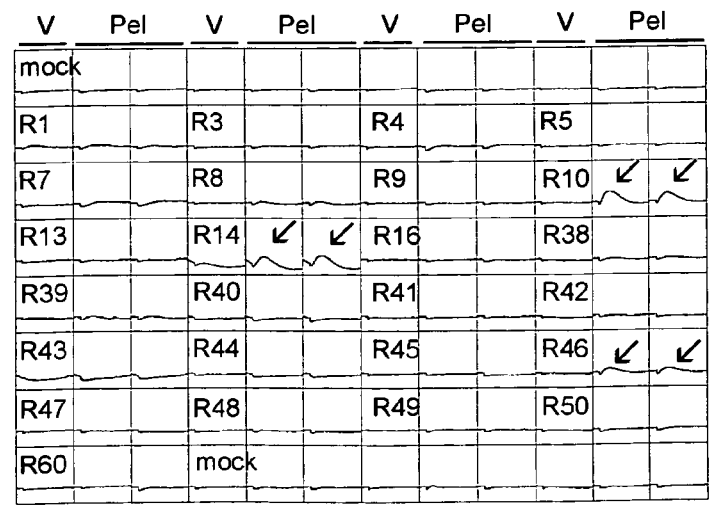

At the maximal test concentration that did not elicit unspecific signals in mock-transfected cells (100 μM), cells transfected with cDNAs for hTAS2R1, —R4, —R7, —R8, —R10, —R14, —R38, or —R44 responded to 3β hydroxy dihydro costunolide (FIG. 2A). However, control experiments revealed that the signals obtained with hTAS2R38 expressing cells were generated by DMSO used as solvent (FIG. 2B). Cells expressing any of the other TAS2R5 did not respond (FIG. 2A). Similarly, we found that cells expressing hTAS2R10, —R14, or —R46 displayed calcium signals following administration of 3β hydroxy pelenolide. Signal amplitudes were comparatively small (FIG. 2C).

Figure 3:
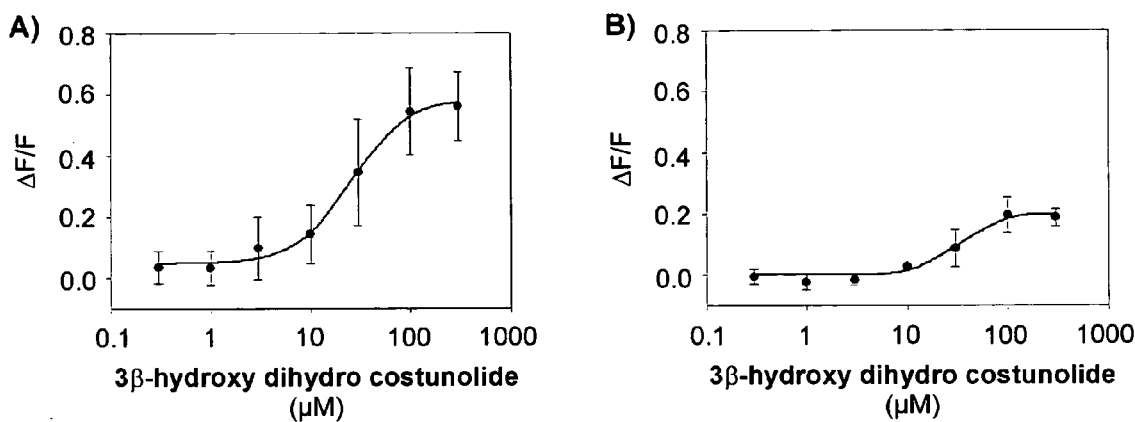
FIG. 3A-B show concentration-response relation of 3β hydroxy dihydro costunolide on the intracellular calcium levels of hTAS2R10-(FIG. 3A) and hTAS2R44-expressing cells (FIG. 3B). Data was derived from three independent experiments carried out in duplicates.

For the activation of hTAS2R10 and hTAS2R44 by 3β hydroxy dihydro costunolide concentration-response relations were determined (FIG. 3) revealing $EC_{50}$ values of 25.2±3.6 μM and 31.5±7.4 μM, respectively. For the other receptors that were stimulated by 3β hydroxy dihydro costunolide and 3β hydroxy pelenolide $EC_{50}$ values were not calculated as receptor activation did not reach saturation within concentration ranges of the substances employed.

Figure 4:
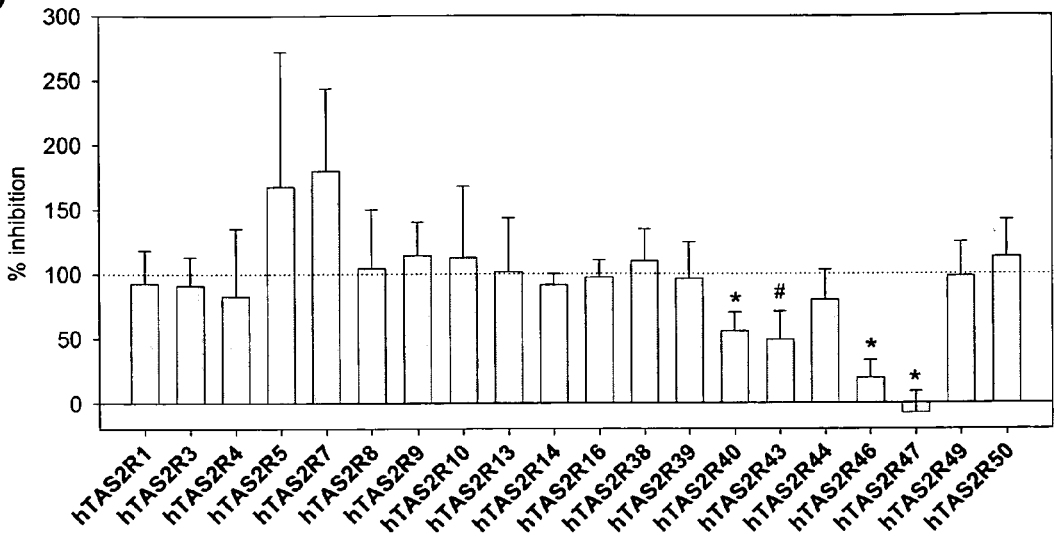
FIG. 4A-B show effect of 3β hydroxy dihydro costunolide (FIG. 4A, 100 μM) and 3β hydroxy pelenolide (FIG. 4B, 100 μM) on agonist-dependent responses of hTAS2 receptors. % Inhibition is defined as percentaged response to agonist stimulation in presence of 3β hydroxy dihydro costunolide (FIG. 4A) and 3β hydroxy pelenolide (FIG. 4B), respectively.*) $p<0.05$. #) Trend, $p<0.1$.
Figure 4:
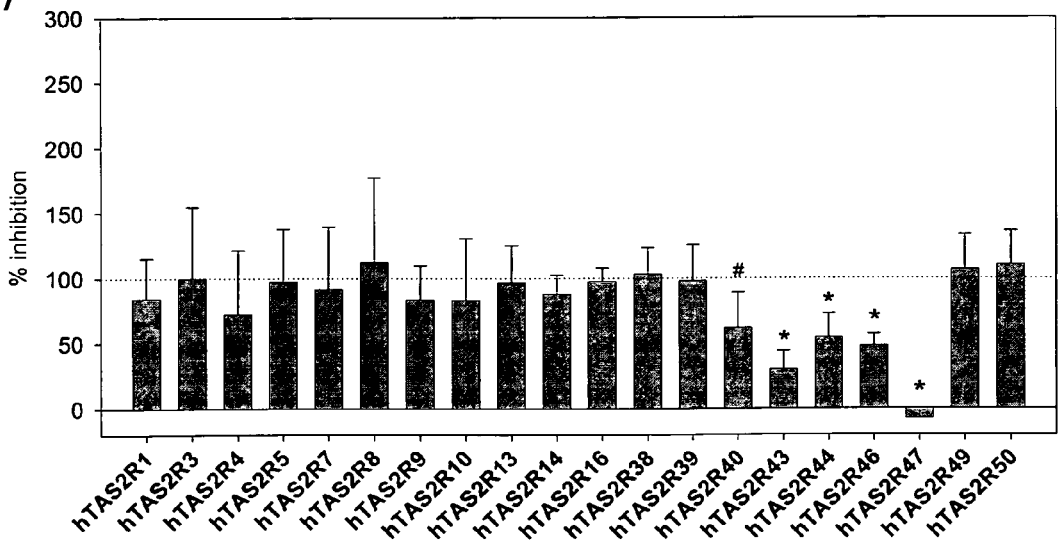

To test 3β hydroxy dihydro costunolide and 3β hydroxy pelenolide for antagonistic or enhancing effects on hTAS2R activation, transfected cells were stimulated with cognate agonist bitter substances at $EC_{90}$ concentrations (Table 2) without 3β hydroxy dihydro costunolide and 3β hydroxy pelenolide. The cellular responses after application of the agonist alone were set to 100%, responses obtained after coapplication of agonists and 100 μM 3β hydroxy dihydro costunolide or 100 μM 3β hydroxy pelenolide are shown relative to this value (FIG. 4). Receptors hTAS241, -42, -45, -48 and —R60 are orphan receptors and hence not tested for inhibitory effects.

Coapplication of specific receptor agonists and 100 μM 3β hydroxy dihydro costunolide led to increased responses of hTAS2R5- and hTAS2R7-expressing cells (FIG. 4A). In contrast to that, in hTAS2R46- and hTAS2R47-transfected cells 3β hydroxy dihydro costunolide caused a complete block of agonist-dependent receptor activation whereas the agonist-induced response of hTAS2R40- and hTAS2R43-expressing cells was only moderately reduced by 3β hydroxy dihydro costunolide. The compound did not alter agonist-activation in cells expressing any of the other hTAS2R5.

The second test substance, 3β hydroxy pelenolide, completely inhibited the activation of hTAS2R43 and hTAS2R47-transfected cells by their cognate agonists (FIG. 4B). Furthermore, it shows a moderately attenuating effect on the agonist-dependent stimulation of hTAS2R40, hTAS2R44 and hTAS2R46-expressing cells. Agonist activation of other receptors was not affected.

Figure 5:
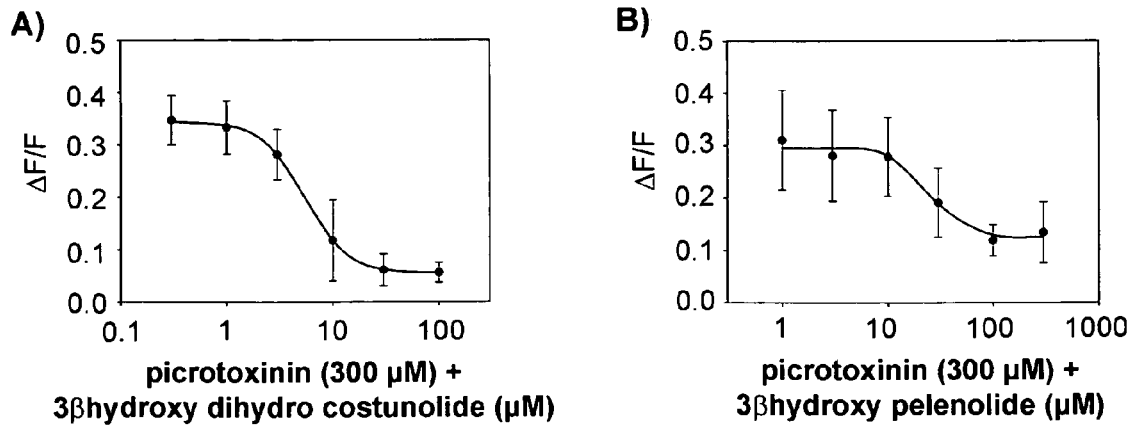
FIG. 5A-B show concentration response relations of 3β hydroxy dihydro costunolide (FIG. 5A) and 3β hydroxy pelenolide (FIG. 5B) on agonist-induced increases in intracellular calcium levels of hTAS2R46-expressing cells. Data derived from three independent experiments carried out in duplicates.

Next we determined concentrations of half-maximal inhibition of TAS2R46. FIG. 5 illustrates the concentration-inhibition curves of TAS2R46 activated by picrotoxinin in the presence of various concentrations of 3β hydroxy dihydro costunolide or 3β hydroxy pelenolide. Table 3 displays the calculated $IC_{50}$ values for these compounds and this receptor activated by some of its cognate bitter agonists. In agreement with the data described above the costunolide analog appears to be more potently inhibiting TAS2R46 than the pelenolide analog. Moreover, 3β hydroxy dihydro costunolide is more potent at TAS2R46 than all tested agonists but strychnine. 50% inhibition was observed at ~6 to 60 fold lower inhibitor concentration than the agonist concentrations. As expected 3β hydroxy pelenolide has to be employed at ~6 fold higher concentrations than 3β hydroxy dihydro costunolide to achieve 50% receptor inhibition.

TABLE 3

Half maximal inhibitory concentration ($IC_{50}$) of 3β hydroxy dihydro costunolide and 3β hydroxy pelenolide on hTAS2R46. Agonist concentrations applied correspond to the lowest substance concentration saturating the response of hTAS2R46-expressing cells (Brockhoff et al. 2007, supra). Data derived from three independent experiments carried out in duplicates.

| agonist | agonist concentration μM | 3β hydroxy dihydro costunolide $IC_{50}$ in μM | 3β hydroxy pelenolide $IC_{50}$ in μM |
|---|---|---|---|
| absinthin | 100 | 14.1 ± 1.35 | 57.8 ± 24.9 |
| andrographolide | 30 | 4.93 ± 0.54 | 44.5 ± 34.5 |
| denatonium benzoate | 300 | 6.78 ± 2.33 | 51.4 ± 28.8 |
| picrotoxinin | 300 | 4.81 ± 1.43 | 22.9 ± 3.4 |
| strychnine | 3 | 15.3 ± 5.85 | 84.9 ± 50.2 |

Figure 6:
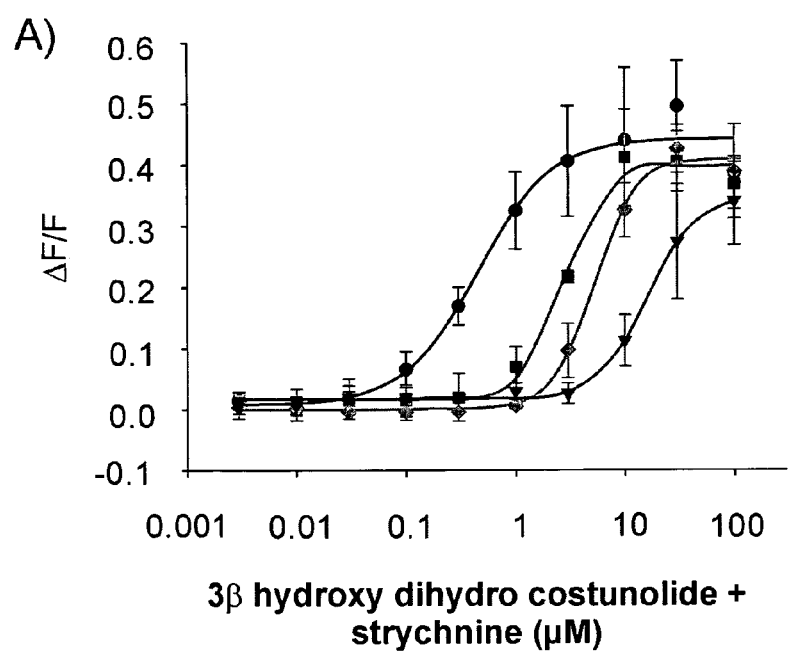
FIG. 6 (A) Receptor-expressing cells were challenged with increasing concentrations of the agonist strychnine and the inhibitor 3β hydroxy dihydro costunolide (0 μM, black curve with filled circles; 10 μM, medium grey curve with filled squares; 30 μM, light grey curve with diamonds; 100 μM, dark grey curve with triangles).

Next, we established concentration-response curves for strychnine at TAS2R46 in the presence of various concentrations of 3β hydroxy dihydro costunolide. FIG. 6 clearly indicates that increasing concentrations of 3β hydroxy dihydro costunolide right-shift the concentration-response curves and increase the $EC_{50}$-value for the toxin whereas the response amplitude remains largely unaffected. This finding strongly favors a competitive mode of action of the inhibitor and suggests that it binds to the same site of TAS2R46 as the agonists do.

Figure 7:
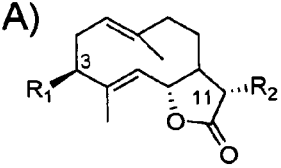
FIG. 7A-B shows impact of chemical modifications on the antagonistic properties of 3β hydroxy dihydro costunolide on hTAS2R46-expressing cells. Derivatives of 3B hydroxy dihydro costunolide with site-directed modifications at C3 and C11 (FIG. 7A) were tested for activation or inhibition of hTAS2R46-expressing cells in absence or presence of the agonist strychnine (3 μM) and half-maximum effective concentrations ($EC_{50}$) or half-maximal inhibitory concentrations were calculated (FIG. 7B).

Finally, the impact of chemical modifications on the antagonistic properties of 3β hydroxy dihydro costunolide on hTAS2R46-expressing cells was studied. Derivatives of 3β hydroxy dihydro costunolide with site-directed modifications at C3 and C11 were generated (FIG. 7A) These derivatives were tested for activation or inhibition of hTAS2R46-expressing cells in the absence or presence of the agonist strychnine (3 μM) and half-maximum effective concentrations ($EC_{50}$) or half-maximal inhibitory concentrations were calculated (FIG. 7B).

Costunolide, a natural substance related to 3β hydroxy dihydro costunolide, acts as agonist on hTAS2R46-expressing cells. Saturation of the exomethylene group at C11 has no influence on the agonistic properties of costunolide (conf. dihydro costunolide). Derivatives with polar substitutions at C3 (—OH, 3β hydroxy dihydro costunolide; ═O, 3keto dihydro costunolide) act as antagonists on hTAS2R46-expressing cells. Derivatives with non-polar substitutions at C3 (—H, costunolide; —OAc, 3β hydroxy dihydro costunolide acetate) act as agonists on hTAS2R46-expressing cells.

These results underline the importance of a polar residue at C3 for the antagonistc properties of the compounds described herein.

The invention claimed is:

1. A method for identifying an antagonist of hTAS2R46 bitter taste receptor activity, wherein the bitter taste receptor is encoded by a polynucleotide selected from the group consisting of:
   (a) polynucleotide encoding at least the mature form of the polypeptide having the amino acid sequence as shown in SEQ ID NO: 10;
   (b) polynucleotide having the coding nucleotide sequence as shown in SEQ ID NO: 9 encoding at least the mature form of the polypeptide;
   (c) polynucleotide encoding a fragment of a polypeptide encoded by a polynucleotide of any one of (a) to (b), wherein said fragment has at least 95% sequence identity to SEQ ID NO: 10 and has hTAS2R46 bitter taste receptor activity;
   (d) polynucleotide which is an ortholog of the polynucleotide sequences shown in SEQ ID NO: 9 encoding at least the mature form of the corresponding bitter taste receptor; and
   (e) polynucleotide which encodes a polypeptide having hTAS2R46 bitter taste receptor activity and where said polypeptide is at least 95% identical to a polypeptide as shown in SEQ ID NO: 10;

comprising the steps:
   (1) contacting a bitter taste receptor encoded by said polynucleotide or a host cell genetically engineered with said polynucleotide or with a vector containing said polynucleotide to express said bitter taste receptor with a potential antagonist or with a pharmaceutically acceptable salt thereof, said potential antagonist having a structure according to formula (IV):

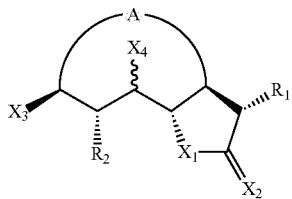

(IV)

wherein
   $X_1$ is —O—, —S—, or —NH—, preferably —O— or —S—, most preferably —O—;
   $X_2$ is =O, =S, or =NH, preferably =O or =S, most preferably =O;
   $X_3$ is —OH, —SH, —NH$_2$, —NO$_2$, —CN, —COOH, =O, =S, =NH, —O—CH$_3$, —S—CH$_3$, or —NH—CH$_3$, preferably —OH, —SH, —NH$_2$, —NO$_2$, —CN, —COOH, =O, =S, or =NH, more preferably —OH, —SH, =O, or =S, even more preferably —OH or —SH, most preferably —OH;

$X_4$ is selected from the group consisting of hydrogen, $C_1$ to $C_4$ alkyl, $C_1$ to $C_4$ alkenyl, $C_2$ to $C_4$ alkynyl, $C_1$ to $C_3$ alkoxy, $C_1$ to $C_3$ heteroalkyl, $C_1$ to $C_3$ heteroalkenyl, and $C_2$ to $C_3$ heteroalkynyl; or $X_4$ forms a single bond to A; preferably $X_4$ is hydrogen or —CH$_3$ or forms a single bond to A; more preferably $X_4$ is hydrogen;
   A is selected from the group consisting of straight or branched $C_4$ to $C_7$ alkyl, straight or branched $C_4$ to $C_7$ alkenyl, straight or branched $C_4$ to $C_7$ alkynyl, straight or branched $C_3$ to $C_6$ heteroalkyl, straight or branched $C_3$ to $C_6$ heteroalkenyl, and straight or branched $C_3$ to $C_6$ heteroalkynyl, wherein said alkyl, alkenyl, alkynyl, heteroalkyl, heteroalkenyl, and heteroalkynyl are optionally substituted 1, 2, 3, 4, or 5 times, preferably 1, 2, or 3 times, and more preferably once or twice;
   $R_1$ is selected from the group consisting of hydrogen, $C_1$ to $C_4$ alkyl, $C_1$ to $C_4$ alkenyl, $C_2$ to $C_4$ alkynyl, $C_1$ to $C_3$ alkoxy, $C_1$ to $C_3$ heteroalkyl, $C_1$ to $C_3$ heteroalkenyl, and $C_2$ to $C_3$ heteroalkynyl, wherein said alkyl, alkenyl, alkynyl, alkoxy, heteroalkyl, heteroalkenyl, and heteroalkynyl are optionally substituted once or twice; preferably $R_1$ is —CH$_3$ or =CH$_2$ or hydrogen, more preferably —CH$_3$ or =CH$_2$;
   $R_2$ is selected from the group consisting of hydrogen, $C_1$ to $C_4$ alkyl, $C_1$ to $C_4$ alkenyl, $C_2$ to $C_4$ alkynyl, $C_1$ to $C_3$ alkoxy, $C_1$ to $C_3$ heteroalkyl, $C_1$ to $C_3$ heteroalkenyl, and $C_2$ to $C_3$ heteroalkynyl, wherein said alkyl, alkenyl, alkynyl, alkoxy, heteroalkyl, heteroalkenyl, and heteroalkynyl are optionally substituted once or twice; preferably $R_2$ is —CH$_3$ or hydrogen, more preferably —CH$_3$; and (2) determining whether the potential antagonist inhibits the bitter taste receptor activity;
   wherein prior to, concomitantly with and/or after step (1) said bitter taste receptor or said host cell is contacted with an agonist of bitter bitter taste receptor hTAS2R46.

2. The method of claim 1, wherein A is selected from the group consisting of straight $C_5$ alkyl, straight $C_5$ alkenyl, straight $C_5$ alkynyl, straight $C_4$ heteroalkyl, straight $C_4$ heteroalkenyl, and straight $C_4$ heteroalkynyl; preferably straight $C_5$ alkyl and straight $C_5$ alkenyl;
   wherein said alkyl, alkenyl, alkynyl, heteroalkyl, heteroalkenyl, and heteroalkynyl are optionally substituted 1, 2, 3, 4, or 5 times, preferably 1, 2, or 3 times, and more preferably once or twice.

3. The method of claim 1, wherein the optional substituents of A are in each instance independently selected from the group consisting of halogen, —OH, —SH, —NH$_2$, —NO$_2$, —CN, —COOH, =O, =S, =NH, $C_1$ to $C_4$ alkyl, $C_1$ to $C_4$ alkenyl, $C_2$ to $C_4$ alkynyl, $C_1$ to $C_3$ alkoxy, $C_1$ to $C_3$ heteroalkyl, $C_1$ to $C_3$ heteroalkenyl, and $C_2$ to $C_3$ heteroalkynyl; preferably —OH, —O—C(O)—CH$_3$, —CH$_3$, and =CH$_2$.

4. The method of claim 1, wherein said potential antagonist has a structure according to formula (VI):

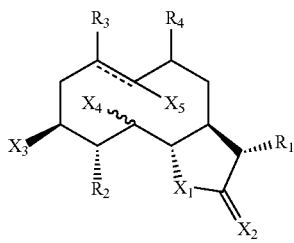

(VI)

wherein $X_1$, $X_2$, $X_3$, $R_1$ and $R_2$ are defined as in claim 1;

$X_4$ is selected from the group consisting of hydrogen, $C_1$ to $C_4$ alkyl, $C_1$ to $C_4$ alkenyl, $C_2$ to $C_4$ alkynyl, $C_1$ to $C_3$ alkoxy, $C_1$ to $C_3$ heteroalkyl, $C_1$ to $C_3$ heteroalkenyl, and $C_2$ to $C_3$ heteroalkynyl, or $X_4$ forms a single bond to the carbon atom carrying $X_5$; preferably $X_4$ is hydrogen or —$CH_3$ or forms a single bond to the carbon atom carrying $X_5$; more preferably $X_4$ is hydrogen;

$X_5$ is selected from the group consisting of hydrogen, $C_1$ to $C_4$ alkyl, $C_1$ to $C_4$ alkenyl, $C_2$ to $C_4$ alkynyl, $C_1$ to $C_3$ alkoxy, $C_1$ to $C_3$ heteroalkyl, $C_1$ to $C_3$ heteroalkenyl, and $C_2$ to $C_3$ heteroalkynyl; preferably $X_5$ is hydrogen, —$CH_3$, or $=CH_2$; more preferably $X_5$ is —$CH_3$ or $=CH_2$;

$R_3$ is selected from the group consisting of hydrogen, halogen, —OH, —SH, —$NH_2$, —$NO_2$, —CN, —COOH, $=O$, $=S$, $=NH$, $C_1$ to $C_4$ alkyl, $C_1$ to $C_4$ alkenyl, $C_2$ to $C_4$ alkynyl, $C_1$ to $C_3$ alkoxy, $C_1$ to $C_3$ heteroalkyl, $C_1$ to $C_3$ heteroalkenyl, and $C_2$ to $C_3$ heteroalkynyl; preferably —OH, —O—C(O)—$CH_3$, —$CH_3$, and $=CH_2$;

$R_4$ is selected from the group consisting of hydrogen, halogen, —OH, —SH, —$NH_2$, —$NO_2$, —CN, —COOH, $=O$, $=S$, $=NH$, $C_1$ to $C_4$ alkyl, $C_1$ to $C_4$ alkenyl, $C_2$ to $C_4$ alkynyl, $C_1$ to $C_3$ alkoxy, $C_1$ to $C_3$ heteroalkyl, $C_1$ to $C_3$ heteroalkenyl, and $C_2$ to $C_3$ heteroalkynyl; preferably —OH, —O—C(O)—$CH_3$, —$CH_3$, and $=CH_2$; and the dotted line between the carbon atom carrying $R_3$ and the carbon atom carrying $X_5$ designates an optional bond, i.e. said two carbon atoms may be linked via a single bond or a double bond.

5. A method for identifying an antagonist of hTAS2R46 bitter taste receptor activity, wherein the bitter taste receptor is encoded by a polynucleotide selected from the group consisting of:

(a) polynucleotide encoding at least the mature form of the polypeptide having the amino acid sequence as shown in SEQ ID NO: 10;

(b) polynucleotide having the coding nucleotide sequence as shown in SEQ ID NO: 9 encoding at least the mature form of the polypeptide;

(c) polynucleotide encoding a fragment of a polypeptide encoded by a polynucleotide of any one of (a) to (b), wherein in said fragment has at least 95% sequence identity to SEQ ID NO: 10 and has hTAS2R46 bitter taste receptor activity;

(d) polynucleotide which is an ortholog of the polynucleotide sequences shown in SEQ ID NO: 9 encoding at least the mature form of the corresponding bitter taste receptor; and (e) polynucleotide which encodes a polypeptide having hTAS2R46 bitter taste receptor activity and where said polypeptide is at least 95% identical to a polypeptide as shown in SEQ ID NO: 10;

comprising the steps:

(1) contacting a bitter taste receptor encoded by said polynucleotide or a host cell genetically engineered with said polynucleotide or with a vector containing said polynucleotide to express said bitter taste receptor with a potential antagonist or with a pharmaceutically acceptable salt thereof, said potential antagonist having a structure according to formula (III):

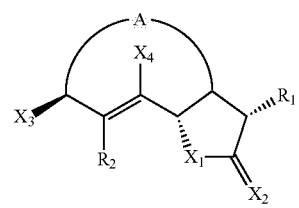

(III)

wherein $X_1$ is —O—, —S—, or —NH—, preferably —O— or —S—, most preferably —O—;

$X_2$ is $=O$, $=S$, or $=NH$, preferably $=O$ or $=S$, most preferably $=O$;

$X_3$ is —OH, —SH, —$NH_2$, —$NO_2$, —CN, —COOH, $=O$, $=S$, $=NH$, —O—$CH_3$, —S—$CH_3$, or —NH—$CH_3$, preferably —OH, —SH, —$NH_2$, —$NO_2$, —CN, —COOH, $=O$, $=S$, or $=NH$, more preferably —OH, —SH, $=O$, or $=S$, even more preferably —OH or —SH, most preferably —OH;

$X_4$ is selected from the group consisting of hydrogen, $C_1$ to $C_4$ alkyl, $C_2$ to $C_4$ alkenyl, $C_2$ to $C_4$ alkynyl, $C_1$ to $C_3$ alkoxy, $C_1$ to $C_3$ heteroalkyl, $C_2$ to $C_3$ heteroalkenyl, and $C_2$ to $C_3$ heteroalkynyl; or $X_4$ forms a single bond to A; preferably $X_4$ is hydrogen or —$CH_3$ or forms a single bond to A; more preferably $X_4$ is hydrogen;

A is selected from the group consisting of $C_4$ to $C_7$ alkyl, $C_4$ to $C_7$ alkenyl, $C_4$ to $C_7$ alkynyl, $C_3$ to $C_6$ heteroalkyl, $C_3$ to $C_6$ heteroalkenyl, and $C_3$ to $C_6$ heteroalkynyl, wherein said alkyl, alkenyl, alkynyl, heteroalkyl, heteroalkenyl, and heteroalkynyl are optionally substituted 1, 2, 3, 4, or 5 times, preferably 1, 2, or 3 times, and more preferably once or twice;

$R_1$ is selected from the group consisting of hydrogen, $C_1$ to $C_4$ alkyl, $C_1$ to $C_4$ alkenyl, $C_2$ to $C_4$ alkynyl, $C_1$ to $C_3$ alkoxy, $C_1$ to $C_3$ heteroalkyl, $C_1$ to $C_3$ heteroalkenyl, and $C_2$ to $C_3$ heteroalkynyl, wherein said alkyl, alkenyl, alkynyl, alkoxy, heteroalkyl, heteroalkenyl, and heteroalkynyl are optionally substituted once or twice; preferably $R_1$ is —$CH_3$ or $=CH_2$ or H, more preferably —$CH_3$ or $=CH_2$;

$R_2$ is selected from the group consisting of hydrogen, $C_1$ to $C_4$ alkyl, $C_2$ to $C_4$ alkenyl, $C_2$ to $C_4$ alkynyl, $C_1$ to $C_3$ alkoxy, $C_1$ to $C_3$ heteroalkyl, $C_2$ to $C_3$ heteroalkenyl, and $C_2$ to $C_3$ heteroalkynyl, wherein said alkyl, alkenyl, alkynyl, alkoxy, heteroalkyl, heteroalkenyl, and heteroalkynyl are optionally substituted once or twice; preferably $R_2$ is —$CH_3$ or hydrogen, more preferably —$CH_3$; and (2) determining whether the potential antagonist inhibits the bitter taste receptor activity;

wherein prior to, concomitantly with and/or after step (1) said bitter taste receptor or said host cell is contacted with an agonist of bitter taste receptor hTAS2R46.

6. The method of claim 5, wherein A is selected from the group consisting of straight $C_5$ alkyl, straight $C_5$ alkenyl, straight $C_5$ alkynyl, straight $C_4$ heteroalkyl, straight $C_4$ heteroalkenyl, and straight $C_4$ heteroalkynyl; preferably straight $C_5$ alkyl and straight $C_5$ alkenyl;

wherein said alkyl, alkenyl, alkynyl, heteroalkyl, heteroalkenyl, and heteroalkynyl are optionally substituted 1, 2, 3, 4, or 5 times, preferably 1, 2, or 3 times, and more preferably once or twice.

7. The method of claim 5, wherein the optional substituents of A are in each instance independently selected from the group consisting of halogen, —OH, —SH, —NH$_2$, —NO$_2$, —CN, —COOH, =O, =S, =NH, $C_1$ to $C_4$ alkyl, $C_1$ to $C_4$ alkenyl, $C_2$ to $C_4$ alkynyl, $C_1$ to $C_3$ alkoxy, $C_1$ to $C_3$ heteroalkyl, $C_1$ to $C_3$ heteroalkenyl, and $C_2$ to $C_3$ heteroalkynyl; preferably —OH, —O—C(O)—CH$_3$, —CH$_3$, and =CH$_2$.

8. The method of claim 5, wherein said potential antagonist has a structure according to formula (V):

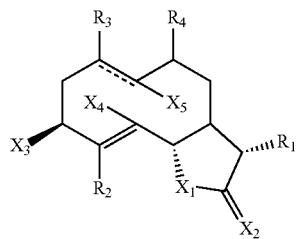

(V)

wherein $X_1$, $X_2$, $X_3$, $R_1$ and $R_2$ are defined as in claim 5;

$X_4$ is selected from the group consisting of hydrogen, $C_1$ to $C_4$ alkyl, $C_2$ to $C_4$ alkenyl, $C_2$ to $C_4$ alkynyl, $C_1$ to $C_3$ alkoxy, $C_1$ to $C_3$ heteroalkyl, $C_2$ to $C_3$ heteroalkenyl, and $C_2$ to $C_3$ heteroalkynyl, or $X_4$ forms a single bond to the carbon atom carrying $X_5$; preferably $X_4$ is hydrogen or —CH$_3$ or forms a single bond to the carbon atom carrying $X_5$; more preferably $X_4$ is hydrogen;

$X_5$ is selected from the group consisting of hydrogen, $C_1$ to $C_4$ alkyl, $C_1$ to $C_4$ alkenyl, $C_2$ to $C_4$ alkynyl, $C_1$ to $C_3$ alkoxy, $C_1$ to $C_3$ heteroalkyl, $C_1$ to $C_3$ heteroalkenyl, and $C_2$ to $C_3$ heteroalkynyl; preferably $X_5$ is hydrogen, —CH$_3$, or =CH$_2$; more preferably $X_5$ is —CH$_3$ or =CH$_2$;

$R_3$ is selected from the group consisting of hydrogen, halogen, —OH, —SH, —NH$_2$, —NO$_2$, —CN, —COOH, =O, =S, =NH, $C_1$ to $C_4$ alkyl, $C_1$ to $C_4$ alkenyl, $C_2$ to $C_4$ alkynyl, $C_1$ to $C_3$ alkoxy, $C_1$ to $C_3$ heteroalkyl, $C_1$ to $C_3$ heteroalkenyl, and $C_2$ to $C_3$ heteroalkynyl; preferably —OH, —O—C(O)—CH$_3$, —CH$_3$, and =CH$_2$;

$R_4$ is selected from the group consisting of hydrogen, halogen, —OH, —SH, —NH$_2$, —NO$_2$, —CN, —COOH, =O, =S, =NH, $C_1$ to $C_4$ alkyl, $C_1$ to $C_4$ alkenyl, $C_2$ to $C_4$ alkynyl, $C_1$ to $C_3$ alkoxy, $C_1$ to $C_3$ heteroalkyl, $C_1$ to $C_3$ heteroalkenyl, and $C_2$ to $C_3$ heteroalkynyl; preferably —OH, —O—C(O)—CH$_3$, —CH$_3$, and =CH$_2$; and the dotted line between the carbon atom carrying $R_3$ and the carbon atom carrying $X_5$ designates an optional bond, i.e. said two carbon atoms may be linked via a single bond or a double bond.

9. The method of claim 5 wherein the agonist of bitter taste receptor hTAS2R46 is selected from the group consisting of picrotoxinin, strychnine, absinthin, amarogentin, andrographolide, arborescin, arglabin, artemorin, brucine, caffeine, cascarillin, cnicin, colchicine, crispolide, grossheimin, parthenolide, quassin, quinine, tatridin B, yohimbin, azathioprine, carisoprodol, chloramphenicol, chlorpheniramine, denatonium benzoate, diphenidole, hydrocortisone, and orphenadrine.

10. The method of claim 5, wherein hTAS2R46 bitter taste receptor activity is determined by measuring a change in concentration of an intracellular messenger.

11. The method of claim 5 further comprising the step:
(3) isolating a potential antagonist that reduces the activity of hTAS2R46 stimulated by an agonist of hTAS2R46.

12. The method of claim 1, wherein the agonist of bitter taste receptor hTAS2R46 is selected from the group consisting of picrotoxinin, strychnine, absinthin, amarogentin, andrographolide, arborescin, arglabin, artemorin, brucine, caffeine, cascarillin, cnicin, colchicine, crispolide, grossheimin, parthenolide, quassin, quinine, tatridin B, yohimbin, azathioprine, carisoprodol, chloramphenicol, chlorpheniramine, denatonium benzoate, diphenidole, hydrocortisone, and orphenadrine.

13. The method of claim 1, wherein hTAS2R46 bitter taste receptor activity, is determined by measuring a change in concentration of an intracellular messenger.

14. The method of claim 1 further comprising the step:
(3) isolating a potential antagonist that reduces the activity of hTAS2R46, stimulated by an agonist of hTAS2R46.

* * * * *

UNITED STATES PATENT AND TRADEMARK OFFICE
CERTIFICATE OF CORRECTION

PATENT NO. : 8,673,578 B2  
APPLICATION NO. : 13/504750  
DATED : March 18, 2014  
INVENTOR(S) : Giovanni Appendino et al.

Page 1 of 1

It is certified that error appears in the above-identified patent and that said Letters Patent is hereby corrected as shown below:

In the Claims

Claim 1, Column 66, Line 48 should read as follows:

With an agonist of bitter taste receptor hTAS2R46 delete the word "bitter", which was inserted twice.

Signed and Sealed this  
Third Day of June, 2014

Michelle K. Lee  
*Deputy Director of the United States Patent and Trademark Office*